US008986935B2

(12) United States Patent
Paushkin et al.

(10) Patent No.: US 8,986,935 B2
(45) Date of Patent: Mar. 24, 2015

(54) METHODS FOR TREATING SPINAL MUSCULAR ATROPHY

(75) Inventors: Sergey V. Paushkin, Belle Mead, NJ (US); Nikolai A. Naryshkin, East Brunswick, NJ (US); Ellen Welch, Califon, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 430 days.

(21) Appl. No.: 13/058,653

(22) PCT Filed: Aug. 13, 2009

(86) PCT No.: PCT/US2009/004625

§ 371 (c)(1), (2), (4) Date: Feb. 11, 2011

(87) PCT Pub. No.: WO2010/019236

PCT Pub. Date: Feb. 18, 2010

(65) Prior Publication Data

US 2011/0172284 A1 Jul. 14, 2011

Related U.S. Application Data

(60) Provisional application No. 61/156,429, filed on Feb. 27, 2009, provisional application No. 61/088,649, filed on Aug. 13, 2008.

(51) Int. Cl.

*C12Q 1/68* (2006.01)
*G01N 33/567* (2006.01)
*C12Q 1/02* (2006.01)

(52) U.S. Cl.

CPC .................................... *C12Q 1/6897* (2013.01)
USPC ............................ 435/6.13; 435/7.21; 435/29

(58) Field of Classification Search

None
See application file for complete search history.

(56) References Cited

U.S. PATENT DOCUMENTS

| | | | |
|---|---|---|---|
| 2005/0054836 A1 | 3/2005 | Krainer et al. |
| 2007/0292408 A1 | 12/2007 | Singh et al. |
| 2011/0086833 A1 | 4/2011 | Paushkin et al. |
| 2011/0172284 A1 | 7/2011 | Paushkin et al. |

FOREIGN PATENT DOCUMENTS

| | | |
|---|---|---|
| WO | WO 01/66129 | 9/2001 |
| WO | WO 2004/113867 | 12/2004 |
| WO | WO 2007/002390 | 1/2007 |
| WO | WO 2007/109211 | 9/2007 |
| WO | WO 2007109211 A2 * | 9/2007 |
| WO | WO 2009/151546 | 12/2009 |
| WO | WO 2010/019236 | 2/2010 |
| WO | WO 2010/019243 | 2/2010 |

OTHER PUBLICATIONS

Andreassi et al., 2001, "Aclarubicin treatment restores SMN levels to cells derived from type I spinal muscular atrophy patients," Human Molecular Genetics; 10(24):2841-2849.

Avila et al., 2007 "Trichostatin A increases SMN expression and survival in a mouse model of spinal muscular atrophy," J Clin Invest. ;117(3):659-71.

Bertini et al., 2005, "134th ENMC International Workshop: Outcome Measures and Treatment of Spinal Muscular Atrophy, Feb. 11-13, 2005, Naarden, The Netherlands," Neuromuscul Disord. 15(11):802-16.

Boda et al., 2004, "Survival motor neuron SMN1 and SMN2 gene promoters: identical sequences and differential expression in neurons and non-neuronal cells," Eur J Hum Genet.; 12(9):729-37.

Brahe et al., 2005, "Phenylbutyrate increases SMN gene expression in spinal muscular atrophy patients," Eur J Hum Genet.; 13(2):256-9.

Carrel et al., 2006, "Survival motor neuron function in motor axons is independent of functions required for small nuclear ribonucleoprotein biogenesis", Journal of Neuroscience; 26(43):11014-11022.

Cartegni et al., 2002, "Disruption of an SF2/ASF-dependent exonic splicing enhancer in SMN2 causes spinal muscular atrophy in the absence of SMN1," Nature Genetics; 30:377-384.

Cartegni et al., 2006, "Determinants of exon 7 splicing in the spinal muscular atrophy genes, SMN1 and SMN2," American Journal of Human Genetics; 78:63-77.

Echaniz-Laguna et al., 1999, "The promoters of the survival motor neuron gene (SMN) and its copy (SMNc) share common regulatory elements," Am J Hum Genet; 64(5):1365-70.

Genbank Accession No. EF540695.1, 2007, "Expression vector proSMN2:SMN2:luc, complete sequence", Wilson et al., 2007, "An SMA project report: neural cell-based assays derived from human embryonic stem cells", Stem Cells and Development; 16:1027-1041.

Germain-Desprez et al., 2001, "The SMN genes are subject to transcriptional regulation during cellular differentiation," Gene; 279:109-117.

Gubitz et al., 2004 "The SMN complex," Exp Cell Res.; 296:51-6.

Iannaconne et al., 2002 "Outcome Measures for Pediatric Spinal Muscular Atrophy," Arch Neurol. 59:1445-1450.

Iannaconne et al., 2003, "Reliability of 4 Outcome Measures in Pediatric Spinal Muscular Atrophy," Arch Neurol; 60:1130-1136.

Jarecki et al., 2005 "Diverse small-molecule modulators of SMN expression found by high-throughput compound screening: early leads towards a therapeutic for spinal muscular atrophy," Hum Mol Genet.; 14(14):2003-18.

Kashima et al., 2003, "A negative element in SMN2 exon 7 inhibits splicing in spinal muscular atrophy," Nature Genetics; 34(4):460-463.

Kolb et al., 2006, "A novel cell immunoassay to measure survival of motor neurons protein in blood cells," BMC Neurology, 6:6.

Le et al., 2005, "SMNΔ7, the major product of the centromeric survival motor neuron (SMN2) gene, extends survival in mice with spinal muscular atrophy and associates with full-length SMN", Human Molecular Genetics; 14(6):845-857.

(Continued)

*Primary Examiner* — Jennifer Dunston
(74) *Attorney, Agent, or Firm* — Jones Day

(57) ABSTRACT

Described herein are methods for the identification or validation of compounds capable of causing ribosomal frameshifting and the use of the compounds identified by the methods described herein to produce a stabilized SMNΔEx7 protein and treat Spinal Muscular Atrophy.

9 Claims, 6 Drawing Sheets

(56) References Cited

OTHER PUBLICATIONS

Lorson et al., 1999, "A single nucleotide in the SMN gene regulates splicing and is responsible for spinal muscular atrophy," Proc Natl Acad Sci USA; 96:6307-6311.

Lorson et al., 2000, "An exonic enhancer is required for inclusion of an essential exon in the SMA-determining gene SMN," Human Molecular Genetics; 9(2):259-265.

Lunn et al., 2004, "Indoprofen upregulates the survival motor neuron protein through a cyclooxygenase-independent mechanism", Chemistry & Biology; 11:1489-1493.

Mattis et al., 2006, "Novel aminoglycosides increase SMN levels in spinal muscular atrophy fibroblasts," Human Genetics; pp. 1-13.

Mattis et al., 2008, "A SMN Δ7 read-through product confers functionality to the SMN Δ7 protein," Neuroscience Letters; 442:54-58.

Merlini et al., 2003, "Role of gabapentin in spinal muscular atrophy: results of a multicenter, randomized Italian study," J Child Neurol.; 18(8):537-41.

Monani et al., 1999, Promoter analysis of the human centromeric and telomeric survival motor neuron genes (SMNC and SMNT), Biochim Biophys Acta; 1445(3):330-6.

Paushkin et al.., 2002 "The SMN complex, an assemblyosome of ribonucleoproteins" Curr Opin Cell Biol., 14:305-12.

Rochette et al., 2001, "SMN gene duplication and the emergence of the SMN2 gene occurred in distinct hominids. SMN2 is unique to *Homo sapiens*", Human Genetics; 108(3):255-266.

Schmid et al., 2007, "Animal models of spinal muscular atrophy", Journal of Child Neurology; 22(8):1004-1012.

Singh et al., "In vivo selection reveals combinatorial controls that define a critical exon in the spinal muscular atrophy genes," RNA: 10:1291-1305.

Singh et al., 2007, "Modulating role of RNA structure in alternative splicing of a critical exon in the spinal muscular atrophy genes", Nucleic Acids Research; 35(2):371-389.

Sumner et al., 2006, "SMN mRNA and protein levels in peripheral blood: biomarkers for SMA clinical trials," Neurology, 66:1067-1073.

Sumner, 2006, "Therapeutics development for spinal muscular atrophy," NeuroRx; 3(2):235-245.

Wan, 2005, "The survival of motor neurons protein determines the capacity for snRNP assembly: biochemical deficiency in spinal muscular atrophy," Molec & Cell Biol, 25(13): 5543-5551.

Wilson et al., 2007, "An SMA project report: neural cell-based assays derived from human embryonic stem cells", Stem Cells and Development; 16:1027-1041.

Wolstencroft et al., 2005, "A non-sequence-specific requirement for SMN protein activity: the role of aminoglycosides in inducing elevated SMN protein levels," Hum Mol Genet, 14(9):1199-1210.

Yeo, 2005, "Splicing regulators: targets and drugs", Genome Biology 6(12):240.

Yong et al., 2004, "Why do cells need an assembly machine for RNA-protein complexes," Trends in Cell Biology; 15(5):226-232.

Yuo et al., 2008, "5-(N-ethyl-N-isopropyl)-amiloride enhances SMN2 exon 7 inclusion and protein expression in spinal muscular atrophy cells", Annals of Neurology; 63(1):26-34.

Zhang et al., 2001, "An in vivo reporter system for measuring increased inclusion of exon 7 in SMN2 m RNA: potential therapy of SMA", Gene Therapy; 8(20):1532-1538.

* cited by examiner tagcttcttacccgtactccaccgttggcagcacgatcgcacgtcccacgtgaaccattggtaaaccctgatgggatccata
attcccccaccacctcccatatgtccagattctcttgatgatgctgatgctttgggaagtatgttaatttcatggtacatgagtgg
ctatcatactggctattatatggtaagtaatcactcagcatcttttcctgacaattttttgtagttatgtgactttgttttgtaaatttat
aaaatactacttgcttctctctttatattactaaaaaataaaaataaaaaaatacaactgtctgaggcttaaattactcttgcattgt
ccctaagtataattttagttaattttaaaaagctttcatgctattgttagattattttgattatacacttttgaattgaaattatactttttct
aaataatgttttaatctctgatttgaaattgattgtagggaatggaaaagatgggataatttttcataaatgaaaaatgaaattcttt
ttttttttttttttttgagacggagtcttgctctgttgcccaggctggagtgcaatggcgtgatcttggctcacagcaagctctg
cctcctggattcacgccattctcctgcctcagcctcagaggtagctgggactacaggtgcctgccaccacgcctgtctaattt
tttgtattttttgtaaagacagggtttcactgtgttagccaggatggtctcaatctcctgaccccgtgatccacccgcctcggcc
ttccaagagaaatgaaattttttaatgcacaaagatctggggtaatgtgtaccacattgaaccttggggagtatggcttcaaa
cttgtcactttatacgttagtctcctacggacatgttctattgtattttagtcagaacatttaaaattattttattttattttattttttttt
tttgagacggagtctcgctctgtcacccaggctggagtacagtggcgcagtctcggctcactgcaagctccgcctcccggg
ttcacgccattctcctgcctcagcctctccgagtagctgggactacaggcgcccgccaccacgcccggctaattttttttattt
ttagtagagacggggtttcaccgtggtctcgatctcctgacctcgtgatccacccgcctcggcctcccaaagtgctgggatta
caagcgtgagccaccgcgcccggcctaaaattatttttaaaagtaagctcttgtgccctgctaaaattatgatgtgatattgtag
gcacttgtatttttagtaaattaatatagaagaaacaactgacttaaaggtgtatgtttttaaatgtatcatctgtgtgtgcccccat
taatattcttatttaaaagttaaggccagacatggtggcttacaactgtaatcccaacagtttgtgaggccgaggcaggcagat
cacttgaggtcaggagtttgagaccagcctggccaacatgatgaaaccttgtctctactaaaaataccaaaaaaaatttagcc
aggcatggtggcacatgcctgtaatccgagctacttgggaggctgtggcaggaaaattgctttaatctgggaggcagaggt
tgcagtgagttgagattgtgccactgcactccacccttggtgacagagtgagattccatctcaaaaaaagaaaaaggcctgg
cacggtggctcacacctataatcccagtactttgggaggtagaggcaggtggatcacttgaggttaggagttcaggaccag
cctggccaacatggtgactactccatttctactaaatacacaaaacttagcccagtggcgggcagttgtaatcccagctactt
gagaggttgaggcaggagaatcacttgaacctgggaggcagaggttgcagtgagccgagatcacaccgctgcactctag
cctggccaacagagtgagaatttgcggagggaaaaaaaagtcacgcttcagttgttgtagtataaccttggtatattgtatgta
tcatgaattcctcattttaatgaccaaaaagtaataaatcaacagcttgtaatttgttttgagatcagttatctgactgtaacactgt
aggcttttgtgtttttttaaattatgaaatatttgaaaaaaatacataatgtatatataaagtattggtataatttatgttctaaataactt
tcttgagaaataattcacatggtgtgcagtttacctttgaaagtatacaagttggctgggcacaatggctcacgcctgtaatcc
cagcactttgggaggccagggcaggtggatcacgaggtcaggagatcgagaccatcctggctaacatggtgaaaccccg
tctctactaaaagtacaaaaacaaattagccgggcatgttggcgggcaccttttgtcccagctgctcgggaggctgaggca
ggagagtggcgtgaacccaggaggtggagcttgcagtgagccgagattgtgccagtgcactccagcctgggcgacaga
gcgagactctgtctcaaaaaataaaataaaaaagaaagtatacaagtcagtggttttggttttcagttatgcaaccatcactac
aatttaagaacattttcatcaccccaaaaagaaaccctgttaccttcattttccccagccctaggcagtcagtacactttctgtct
ctatgaatttgtctattttagatattatatataaacggaattatacgatatgtggtcttttgtgtctggcttctttcacttagcatgctat
tttcaagattcatccatgctgtagaatgcaccagtactgcattccttcttattgctgaatattctgttgtttggttatatcacattttat
ccattcatcagttcatggacatttaggttgtttttatttttgggctataatgaataatgttgctatgaacattcgtttgtgttctttttgttt
ttttggtttttttgggttttttttgttttgtttttgtttttgagacagtcttgctctgtctcctaagctggagtgcagtggcatgatcttggc
ttactgcaagctctgcctcccgggttcacaccattctcctgcctcagcccgacaagtagctgggactacaggcgtgtgccac
catgcacggctaatttttttgtatttttagtagagatggggtttcaccgtgttagccaggatggtctcgatctcctgacctcgtgat
ctgcctgcctaggcctcccaaagtgctgggattacaggcgtgagccactgcacctggccttaagtgtttttaatacgtcattg
ccttaagctaacaattcttaacctttgttctactgaagccacgtggttgagataggctctgagtctagcttttaacctctatcttttt
gtcttagaaatctaagcagaatgcaaatgactaagaataatgttgttgaaataacataaaataggttataactttgatactcatta
gtaacaaatctttcaatacatcttacggtctgttaggtgtagattagtaatgaagtgggaagccactgcaagctagtatacatgt
agggaaagatagaaagcattgaagccagaagagagacagaggacatttgggctagatctgacaagaaaaacaaatgtttt
agtattaatttttgactttaaattttttttttatttagtgaatactggtgtttaatggtctcattttaataagtatgacacaggtagtttaa
ggtcatatattttatttgatgaaaataaggtataggccgggcacggtggctcacacctgtaatcccagcactttgggaggccg
aggcaggcggatcacctgaggtcgggagttagagactagcctcaacatggagaaaccccgtctctactaaaaaaaataca
aaattaggcgggcgtggtggtgcatgcctgtaatcccagctactcaggaggctgaggcaggagaattgcttgaacctggg

FIG. 1A aggtggaggttgcggtgagccgagatcacctcattgcactccagcctgggcaacaagagcaaaactccatctcaaaaaa
aaaaaataaggtataagcgggctcaggaacatcattggacatactgaaagaagaaaaatcagctgggcgcagtggctcac
gccggtaatcccaacactttgggaggccaaggcaggcgaatcacctgaagtcgggagttccagatcagcctgaccaacat
ggagaaaccctgtctctactaaaaatacaaaactagccgggcatggtggcgcatgcctgtaatcccagctacttgggaggc
tgaggcaggagaattgcttgaaccgagaaggcggaggttgcggtgagccaagattgcaccattgcactccagcctgggc
aacaagagcgaaactccgtctcaaaaaaaaaaggaagaaaaatattttttaaattaattagtttatttatttttttaagatggagttt
tgccctgtcacccaggctggggtgcaatggtgcaatctcggctcactgcaacctccgcctcctgggttcaagtgattctcctg
cctcagcttcccgagtagctgtgattacagccatatgccaccacgcccagccagttttgtgttttgttttgtttttgtttttttttttg
agagggtgtcttgctctgtcccccaagctggagtgcagcggcgcgatcttggctcactgcaagctctgcctcccaggttcac
accattctcttgcctcagcctcccgagtagctgggactacaggtgcccgccaccacacccggctaatttttttgtgtttttagta
gagatggggtttcactgtgttagccaggatggtctcgatctcctgaccttttgatccacccgcctcagcctccccaagtgctg
ggattataggcgtgagccactgtgcccggcctagtcttgtatttttagtagagtcgggatttctccatgttggtcaggctgttctc
caaatccgacctcaggtgatccgcccgccttggcctccaaaagtgcaaggcaaggcattacaggcatgagccactgtgac
cggcaatgtttttaaatttttttacatttaaattttatttttttagagaccaggtctcactctattgctcaggctggagtgcaagggcac
attcacagctcactgcagccttgacctccagggctcaagcagtcctctcacctcagtttcccgagtagctgggactacagtg
ataatgccactgcacctggctaattttattttatttatttattttttttttgagacagagtcttgctctgtcacccaggctggagtgca
gtggtgtaaatctcagctcactgcagcctccgcctcctgggttcaagtgattctcctgcctcaacctcccaagtagctgggatt
agaggtccccaccaccatgcctggctaatttttttgtactttcagtagaaacggggttttgccatgttggccaggctgttctcgaa
ctcctgagctcaggtgatccaactgtctcggcctcccaaagtgctgggattacaggcgtgagccactgtgcctagcctgag
ccaccacgccggcctaattttaaatttttttgtagagacagggtctcattatgttgcccagggtggtgtcaagctccaggtctca
agtgatccccctacctccgcctcccaaagttgtgggattgtaggcatgagccactgcaagaaaaccttaactgcagcctaat
aattgttttctttgggataacttttaaagtacattaaaagactatcaacttaatttctgatcatattttgttgaataaaataagtaaaat
gtcttgtgaaacaaaatgctttttaacatccatataaagctatctatatatagctatctatatctatatagctattttttttaacttccttt
attttccttacagggttttagacaaaatcaaaaagaaggaaggtgctcacattccttaaatgtaaggagtaagtctgccagcat
tatgaaagtgaatcttacttttgtaaaactttatggtttgtggaaaacaaatgtttttgaacatttaaaaagttcagatgttagaaag
ttgaaaggttaatgtaaaacaatcaatattaaagaattttgatgccaaaactattagataaaaggttaatctacatccctactaga
attctcatacttaactggttggttgtgtggaagaaacatactttcacaataaagagctttaggatatgatgccattttatatcacta
gtaggcagaccagcagacttttttttattgtgatatgggataacctaggcatactgcactgtacactctgacatatgaagtgctc
tagtcaagtttaactggtgtccacagaggacatggtttaactggaattcgtcaagcctctggttctaatttctcatttgcaggaaa
tgctggcatagagcagcacggatccgaagacgccaaaaacataaagaaaggcccggcgccattctatcctctagaggat
ggaaccgctggagagcaactgcataaggctatgaagagatacgccctggttcctggaacaattgcttttacagatgcacata
tcgaggtgaacatcacgtacgcggaatacttcgaaatgtccgttcggttggcagaagctatgaaacgatatgggctgaatac
aaatcacagaatcgtcgtatgcagtgaaaactctcttcaattctttatgccggtgttgggcgcgttatttatcggagttgcagttg
cgcccgcgaacgacatttataatgaacgtgaattgctcaacagtatgaacatttcgcagcctaccgtagtgtttgtttccaaaa
aggggttgcaaaaaattttgaacgtgcaaaaaaaattaccaataatccagaaaattattatcatggattctaaaacggattacc
agggatttcagtcgatgtacacgttcgtcacatctcatctacctcccggttttaatgaatacgattttgtaccagagtcctttgatc
gtgacaaaacaattgcactgataatgaattcctctggatctactgggttacctaagggtgtggcccttccgcatagaactgcct
gcgtcagattctcgcatgccagagatcctatttttggcaatcaaatcattccggatactgcgattttaagtgttgttccattccatc
acggttttggaatgtttactacactcggatatttgatatgtggatttcgagtcgtcttaatgtatagatttgaagaagagctgttttt
acgatcccttcaggattacaaaattcaaagtgcgttgctagtaccaaccctattttcattcttcgccaaaagcactctgattgac
aaatacgatttatctaatttacacgaaattgcttctgggggcgcacctctttcgaaagaagtcggggaagcggttgcaaaacg
cttccatcttccagggatacgacaaggatatgggctcactgagactacatcagctattctgattacacccgagggggatgat
aaaccgggcgcggtcggtaaagttgttccatttttttgaagcgaaggttgtggatctggataccgggaaaacgctgggcgtta
atcagagaggcgaattatgtgtcagaggacctatgattatgtccggttatgtaaacaatccggaagcgaccaacgccttgatt
gacaaggatggatggctacattctggagacatagcttactgggacgaagacgaacacttcttcatagttgaccgcttgaagt
ctttaattaaatacaaaggatatcaggtggcccccgctgaattggaatcgatattgttacaacaccccaacatcttcgacgcg

FIG. 1B ggcgtggcaggtcttcccgacgatgacgccggtgaacttcccgccgccgttgttgttttggagcacggaaagacgatgac
ggaaaaagagatcgtggattacgtcgccagtcaagtaacaaccgcgaaaaagttgcgcggaggagttgtgtttgtggacg
aagtaccgaaaggtcttaccggaaaactcgacgcaagaaaaatcagagagatcctcataaaggccaagaagggcggaa
agtccaaattgcgcggccgctaaatcgaaagtacaggactagccttcctagcaaccgcgggctgggagtctgagacatca
ctcaagatatatgctcggtaacgtatgctctagccatctaactattccctatgtcttataggg
(SEQ ID NO:6)

FIG. 1C

(A)
MAMSSGGSGGGVPEQEDSVLFRRGTGQSDDSDIWDDTALIKAYDKAVASFK
HALKNGDICETSGKPKTTPKRKPAKKNKSQKKNTAASLQQWKVGDKCSAIW
SEDGCIYPATIASIDFKRETCVVVYTGYGNREEQNLSDLLSPICEVANNIEQNA
QENENESQVSTDESENSRSPGNKSDNIKPKSAPWNSFLPPPPPMPGPRLGPGKP
GLKFNGPPPPPPPPPPHLLSCWLPPFPSGPPIIPPPPPICPDSLDDADALGSMLIS
WYMSGYHTGYYMEMLA (SEQ ID NO:1)

(B)
MAMSSGGSGGGVPEQEDSVLFRRGTGQSDDSDIWDDTALIKAYDKAVASFK
HALKNGDICETSGKPKTTPKRKPAKKNKSQKKNTAASLQQWKVGDKCSAIW
SEDGCIYPATIASIDFKRETCVVVYTGYGNREEQNLSDLLSPICEVANNIEQNA
QENENESQVSTDESENSRSPGNKSDNIKPKSAPWNSFLPPPPPMPGPRLGPGKP
GLKFNGPPPPPPPPPPHLLSCWLPPFPSGPPIIPPPPPICPDSLDDADALGSMLIS
WYMSGYHTGYYMEMLAEQH (SEQ ID NO:2)

(C)
MAMSSGGSGGGVPEQEDSVLFRRGTGQSDDSDIWDDTALIKAYDKAVASFK
HALKNGDICETSGKPKTTPKRKPAKKNKSQKKNTAASLQQWKVGDKCSAIW
SEDGCIYPATIASIDFKRETCVVVYTGYGNREEQNLSDLLSPICEVANNIEQNA
QENENESQVSTDESENSRSPGNKSDNIKPKSAPWNSFLPPPPPMPGPRLGPGKP
GLKFNGPPPPPPPPPPHLLSCWLPPFPSGPPIIPPPPPICPDSLDDADALGSMLIS
WYMSGYHTGYYMEMLAIEQH (SEQ ID NO:3)

(D)
MAMSSGGSGGGVPEQEDSVLFRRGTGQSDDSDIWDDTALIKAYDKAVASFK
HALKNGDICETSGKPKTTPKRKPAKKNKSQKKNTAASLQQWKVGDKCSAIW
SEDGCIYPATIASIDFKRETCVVVYTGYGNREEQNLSDLLSPICEVANNIEQNA
QENENESQVSTDESENSRSPGNKSDNIKPKSAPWNSFLPPPPPMPGPRLGPGKP
GLKFNGPPPPPPPPPPHLLSCWLPPFPSGPPIIPPPPPICPDSLDDADALGSMLIS
WYMSGYHTGYYMEMLARAALNDTTKETIRQIWNVKRYRR (SEQ ID NO:4)

(E)
MAMSSGGSGGGVPEQEDSVLFRRGTGQSDDSDIWDDTALIKAYDKAVASFK
HALKNGDICETSGKPKTTPKRKPAKKNKSQKKNTAASLQQWKVGDKCSAIW
SEDGCIYPATIASIDFKRETCVVVYTGYGNREEQNLSDLLSPICEVANNIEQNA
QENENESQVSTDESENSRSPGNKSDNIKPKSAPWNSFLPPPPPMPGPRLGPGKP
GLKFNGPPPPPPPPPPHLLSCWLPPFPSGPPIIPPPPPICPDSLDDADALGSMLIS
WYMSGYHTGYYMEMLAHRAALNDTTKETIRQIWNVKRYRR (SEQ ID NO:5)

FIG. 2

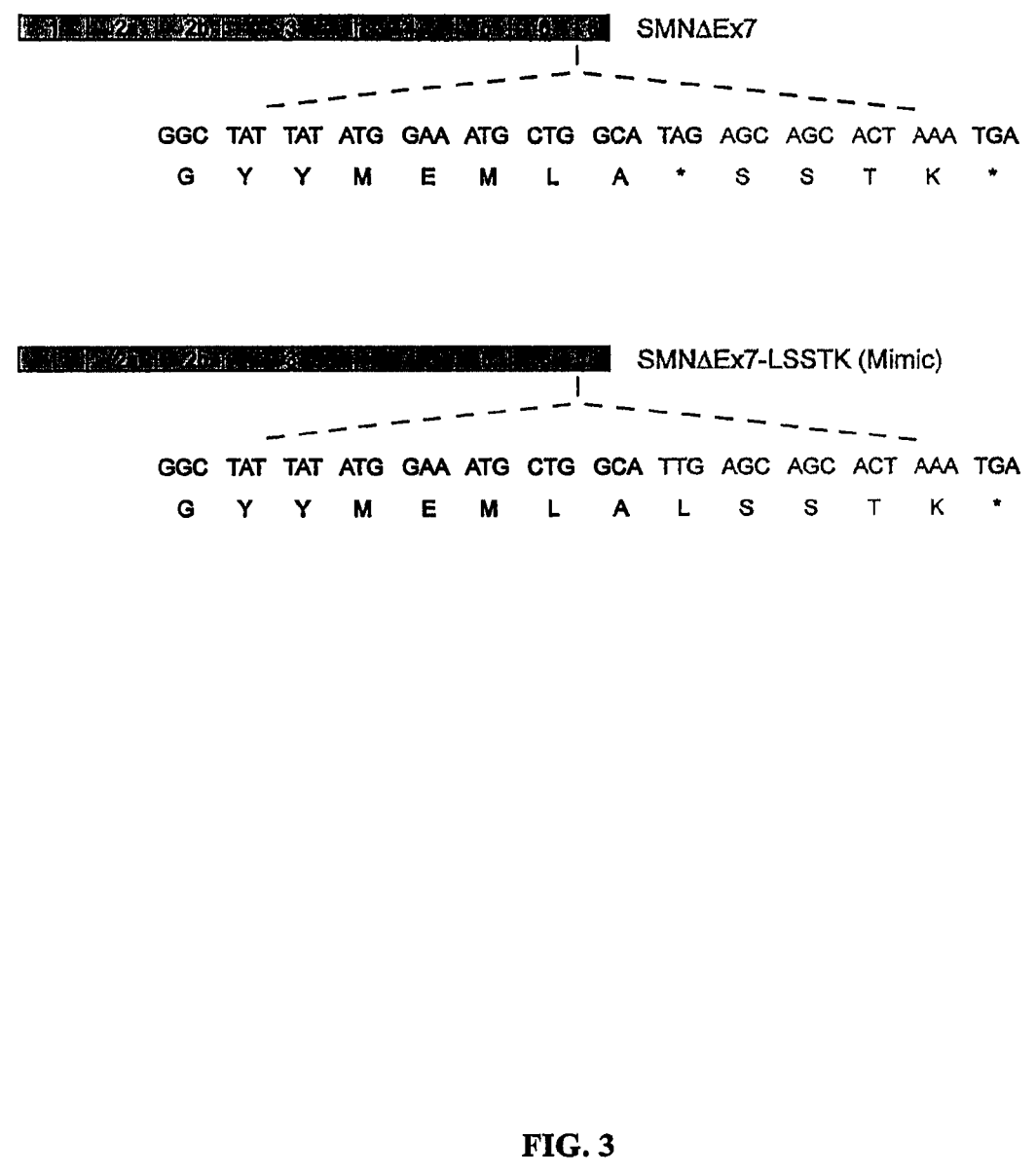

SMNΔEx7

GGC TAT TAT ATG GAA ATG CTG GCA TAG AGC AGC ACT AAA TGA
G Y Y M E M L A * S S T K *

SMNΔEx7-LSSTK (Mimic)

GGC TAT TAT ATG GAA ATG CTG GCA TTG AGC AGC ACT AAA TGA
G Y Y M E M L A L S S T K *

FIG. 3

SMNΔEx7
SMNΔEx7-LSSTK
SMN wt

SMN wt

● SMNΔEx7
■ SMNΔEx7-LSSTK

FIG. 4

METHODS FOR TREATING SPINAL MUSCULAR ATROPHY

This application is a national stage application of International Application No. PCT/US2009/004625, filed Aug. 13, 2009, which claims priority benefit of U.S. provisional application No. 61/088,649, filed Aug. 13, 2008, and U.S. provisional application No. 61/156,429, filed Feb. 27, 2009, each of which is incorporated herein by reference in its entirety.

INTRODUCTION

Described herein are nucleic acid constructs for use in identifying or validating compounds capable of producing a stabilized SMNΔEx7 protein and the use of said compounds to treat Spinal Muscular Atrophy.

BACKGROUND

Spinal Muscular Atrophy ("SMA"), in its broadest sense, describes a collection of inherited and acquired central nervous system (CNS) diseases characterized by motor neuron loss in the spinal cord and brainstem causing muscle weakness and atrophy. The most common form of SMA is caused by mutation of the Survival Motor Neuron ("SMN") gene, and manifests over a wide range of severity affecting infants through adults.

Infantile SMA is one of the most severe forms of this neurodegenerative disorder. The onset is usually sudden and dramatic. Some of the symptoms include: muscle weakness, poor muscle tone, weak cry, limpness or a tendency to flop, difficulty sucking or swallowing, accumulation of secretions in the lungs or throat, feeding difficulties and increased susceptibility to respiratory tract infections. The legs tend to be weaker than the arms and developmental milestones, such as lifting the head or sitting up, cannot be reached. In general, the earlier the symptoms appear, the shorter the lifespan. Shortly after symptoms appear, the motor neuron cells quickly deteriorate. The disease can be fatal and has no known cure. The course of SMA is directly related to the severity of weakness. Infants with a severe form of SMA frequently succumb to respiratory disease due to weakness in the muscles that support breathing. Children with milder forms of SMA live much longer, although they may need extensive medical support, especially those at the more severe end of the spectrum. Disease progression and life expectancy strongly correlate with the subject's age at onset and the level of weakness. The clinical spectrum of SMA disorders has been divided into the following five groups:

(a) In Utero SMA (Type 0 SMA; before birth): Type 0, also known as very severe SMA, is the most severe form of SMA and begins before birth. Usually, the first symptom of type 0 is reduced movement of the fetus that is first seen between 30 and 36 weeks of the pregnancy. After birth, these newborns have little movement and have difficulties with swallowing and breathing.

(b) Infantile SMA (Type 1 SMA or Werdnig-Hoffmann disease; generally 0-6 months): Type 1 SMA, also known as severe infantile SMA or Werdnig Hoffmann disease, is the very severe, and manifests at birth or within 6 months of life. Patients never achieve the ability to sit, and death usually occurs within the first 2 years without ventilatory support.

(c) Intermediate SMA (Type 2 SMA; generally 7-18 months): Patients with Type 2 SMA, or intermediate SMA, achieve the ability to sit unsupported, but never stand or walk unaided. The onset of weakness is usually recognized some time between 6 and 18 months. Prognosis in this group is largely dependent on the degree of respiratory involvement.

(d) Juvenile SMA (Type 3 or Kugelberg-Welander disease; generally >18 months): Type 3 SMA describes those who are able to walk independently at some point during their disease course, but often become wheelchair bound during youth or adulthood.

(e) Adult SMA (Type 4 SMA): Weakness usually begins in late adolescence in tongue, hands, or feet then progresses to other areas of the body. The course of adult disease is much slower and has little or no impact on life expectancy.

The SMA disease gene has been mapped by linkage analysis to a complex region of chromosome 5q. In humans, this region has a large inverted duplication; consequently, there are two copies of the SMN gene. SMA is caused by a mutation or deletion of the telomeric copy of the gene (SMN1) in both chromosomes, resulting in the loss of SMN1 gene function. However, all patients retain a centromeric copy of the gene (SMN2), and its copy number in SMA patients has been implicated as having an important modifying effect on disease severity; i.e., an increased copy number of SMN2 is observed in less severe disease. Nevertheless, SMN2 is unable to compensate completely for the loss of SMN1 function, because the SMN2 gene produces reduced amounts of full-length RNA and is less efficient at making protein, although, it does so in low amounts. More particularly, the SMN1 and SMN2 genes differ by five nucleotides; one of these differences—a translationally silent C to T substitution in an exonic splicing region—results in frequent exon 7 skipping during transcription of SMN2. As a result, the majority of transcripts produced from SMN2 lack exon 7 (SMNΔEx7), and encode a truncated protein which is rapidly degraded.

The SMN protein is thought to play a role in RNA processing and metabolism, having a well characterized function of regulating the assembly of a specific class of RNA-protein complexes called snRNPs. SMN may have other functions in motor neurons, however its role in preventing the selective degeneration of motor neurons is not known.

In most cases, a diagnosis of SMA can be made on the basis of clinical symptoms and by the SMN gene test, which determines whether there is at least one copy of the SMN1 gene by detecting its unique sequences (that distinguish it from the almost identical SMN2) in exon 7 and exon 8. However, other forms of SMA are caused by mutation of other genes, some known and others not defined. In some cases, when the SMN gene test is not possible, or does not show any abnormality, other tests such as an electromyography (EMG) or muscle biopsy may be indicated.

Medical care for SMA patients is supportive, including, respiratory, nutritional and rehabilitation care; there is no drug known to otherwise alter the course of the disease. Current treatment for SMA consists of prevention and management of the secondary effect of chronic motor unit loss. The major management issue in Type 1 SMA is the prevention and early treatment of pulmonary problems, which are the cause of death in the majority of the cases. While some infants afflicted with SMA grow to be adults, those with Type 1 SMA have a life expectancy of less than two years.

As a result of the progress made in understanding the genetic basis and pathophysiology of SMA, several strategies for treatment have been explored, but none have yet demonstrated success. For example, gene replacement (of SMN1) and cell replacement (using differentiated ES cells) strategies are being tested in animals. However, these approaches to treat SMA will require many more years of investigation before they can be applied to humans.

Drugs such as aminoglycosides enhance expression of the SMN protein from SMN2 by promoting translational read-through of a stop codon (Mattis, et al., 2006, *Hum. Genet.* 120:589-601). However, these drugs have poor central nervous system penetration. Chemotherapeutic agents, such as aclarubicin, have been shown to increase SMN protein in cell culture; however, the toxicity profile of these drugs prohibits long-term use in SMA patients. Thus, there remains a need for therapeutically effective compounds to treat SMA.

Described herein are compounds capable of producing stabilized SMNΔEx7, methods by which such compounds may be identified or validated, and methods for treating SMA using such compounds.

SUMMARY

Described herein are nucleic acid constructs for use in identifying or validating compounds capable of producing a stabilized SMNΔEx7 protein and the use of said compounds to treat SMA.

The methods and constructs described herein are based, in part, on the Applicants' discovery that a cryptic splice site is created by a single base change when a guanine nucleotide is inserted after nucleic acid residue 48 of exon 7 of SMN in a nucleic acid construct comprising, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment consists of the first 23 nucleotides from the 5' end of exon 8 of SMN; and (vi) a reporter gene coding sequence lacking a start codon, wherein the reporter gene coding sequence is fused to the fragment of the nucleic acid residues of exon 8 of SMN such that the first codon of the reporter gene coding sequence and the first codon of the fragment of the nucleic acid residues of exon 8 of SMN are out of frame with each other in the mRNA transcript transcribed from the nucleic acid construct and the first codon of each of the nucleic acid residues of exons 6, 7, and 8 are in frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, the nucleic acid construct comprises a start codon upstream (5') to the nucleic acid residues of exon 6 of SMN. In accordance with such embodiments, the first start codon and the stop codon upstream of the reporter gene coding sequence in the mRNA transcript are in the same contiguous open reading frame without any interruption by, e.g., a stop codon.

The cryptic splice site results in a deletion of the last seven nucleotides of exon 7 and creates a spliced mRNA in which (i) the open reading frame defined by the first start codon on the SMN open reading frame is frameshifted relative to the open reading frame of the reporter gene and (ii) the open reading frame defined by the first start codon in the SMN open reading frame contains an aberrant stop codon upstream from the reporter gene coding sequence. Without being limited by theory, the presence of the aberrant stop codon generated by the 5' cryptic splice site, possibly, but not necessarily, in combination with a secondary structure of the downstream RNA, may cause the ribosome to pause and result in a ribosomal frameshift.

Applicants have discovered that certain compounds identified in the assays described herein can induce ribosomal frameshifting during the translation of the SMN2 mRNA containing cryptically spliced fragment of exon 7, and thus, produce a stabilized SMNΔEx7 protein. Accordingly, the nucleic acid constructs described herein may be used to identify or validate compounds that cause ribosomal frameshifting in SMNΔEx7 RNA, thereby producing a stabilized SMNΔEx7 protein, which may be of therapeutic benefit for treating SMA.

Certain nucleic acid constructs described herein for use in methods for identifying or validating compounds that cause ribosomal frameshifting in SMN4Ex7 RNA have been disclosed in co-pending U.S. provisional patent application 61/088,649, filed Aug. 13, 2008.

In one aspect, presented herein are methods for the identification of a compound that causes ribosomal frameshifting. In one embodiment, presented herein is a method for the identification or validation of a compound that causes ribosomal frameshifting comprising: (a) contacting a compound with a host cell containing a nucleic acid construct described herein; and (b) detecting the activity or amount of a fusion protein encoded by the nucleic acid construct, wherein an increase in the activity or amount of the fusion protein expressed by the host cell in the presence of a compound when compared to (i) a previously determined reference range for a negative control, (ii) the activity or amount of the fusion protein expressed by the host cell in the absence of the compound, and/or (iii) the activity or amount of the fusion protein expressed by the host cell in the presence of a negative control indicates that the compound is capable of causing ribosomal frameshifting.

In another embodiment, presented herein is a method for the identification or validation of a compound that causes ribosomal frameshifting comprising: (a) contacting a compound with a host cell containing an RNA transcript (e.g., a mRNA transcript) transcribed from a nucleic acid construct described herein; and (b) detecting the activity or amount of a fusion protein translated from the RNA transcript, wherein an increase in the activity or amount of the fusion protein translated from the RNA transcript in the presence of a compound when compared to (i) a previously determined reference range for a negative control, (ii) the activity or amount of the fusion protein translated from the RNA transcript in the absence of the compound, and/or (iii) the activity or amount of the fusion protein translated from the RNA transcript in the presence of a negative control indicates that the compound is capable of causing ribosomal frameshifting.

In another embodiment, presented herein is a method for the identification or validation of a compound that causes ribosomal frameshifting comprising: (a) contacting a compound with a composition comprising a cell-free extract and an RNA transcript (e.g., a mRNA transcript) transcribed from a nucleic acid construct described herein; and (b) detecting the amount or activity of a fusion protein translated from the RNA transcript, wherein an increase in the activity or amount of the fusion protein translated from the RNA transcript in the presence of a compound when compared to (i) a previously determined reference range for a negative control, (ii) the activity or amount of the fusion protein translated from the RNA transcript in the absence of the compound, and/or (iii) the activity or amount of the fusion protein translated from the RNA transcript in the presence of a negative control indicates that the compound is capable of causing ribosomal frameshifting, In another aspect, presented herein are methods for the identification of a compound that is capable of producing a stabilized SMNΔEx7 protein. In one embodiment, presented herein is a method for the identification or validation of a compound that is capable of producing a stabilized SMNΔEx7 protein comprising: (a) contacting a compound with a host cell containing a nucleic acid construct described herein; and (b) detecting the activity or amount of a fusion protein encoded by the nucleic acid construct, wherein an increase in the activity or amount of the fusion protein expressed by the host cell in the presence of a compound when compared to (i) a previously determined reference range for a negative control, (ii) the activity or amount of the fusion protein expressed by the host cell in the absence of the compound, and/or (iii) the activity or amount of the fusion protein expressed by the host cell in the presence of a negative control indicates that the compound is capable of producing a stabilized SMNΔEx7 protein.

In another embodiment, presented herein is a method for the identification or validation of a compound that is capable of producing a stabilized SMNΔEx7 protein comprising: (a) contacting a compound with a host cell containing an RNA transcript (e.g., a mRNA transcript) transcribed from a nucleic acid construct described herein; and (b) detecting the activity or amount of a fusion protein translated from the RNA transcript, wherein an increase in the activity or amount of the fusion protein translated from the RNA transcript in the presence of a compound when compared to (i) a previously determined reference range for a negative control, (ii) the activity or amount of the fusion protein translated from the RNA transcript in the absence of the compound, and/or (iii) the activity or amount of the fusion protein translated from the RNA transcript in the presence of a negative control indicates that the compound is capable of producing a stabilized SMNΔEx7 protein.

In another embodiment, presented herein is a method for the identification or validation of a compound that is capable of producing a stabilized SMNΔEx7 protein comprising: (a) contacting a compound with a composition comprising a cell-free extract and an RNA transcript (e.g., a mRNA transcript) transcribed from a nucleic acid construct described herein; and (b) detecting the amount or activity of a fusion protein translated from the RNA transcript, wherein an increase in the activity or amount of the fusion protein translated from the RNA transcript in the presence of a compound when compared to (i) a previously determined reference range for a negative control, (ii) the activity or amount of the fusion protein translated from the RNA transcript in the absence of the compound, and/or (iii) the activity or amount of the fusion protein translated from the RNA transcript in the presence of a negative control indicates that the compound is capable of producing a stabilized SMNΔEx7 protein.

Nucleic acid constructs described herein comprise nucleic acid residues of an exon(s) of SMN or a fragment thereof, a reporter gene coding sequence lacking a start codon, and in some instances, nucleic acid residues of an intron(s) of SMN or fragment thereof. In specific aspects, a nucleic acid construct described herein comprises a fragment of the nucleic residues of an exon 8 of SMN fused to a reporter gene coding sequence lacking the start codon, wherein that the first codon of the reporter gene coding sequence and the first codon of the fragment are out of frame with each other in the mRNA transcript transcribed from the nucleic acid construct and the presence of a stop codon upstream of the reporter gene coding sequence in the mRNA transcript causes translation termination prior to translation of the reporter gene coding sequence (i.e., an aberrant stop codon). In such mRNA transcripts, the first start codon and the aberrant stop codon are in the same contiguous open reading frame without any interruption by, e.g., a stop codon. In the presence of certain compounds, the open reading frame may shift so that the first start codon and the aberrant stop codon are no longer in the same open reading frame, and instead the first start codon and the stop codon found at the end of the reporter gene coding sequence are in the same contiguous open reading frame without any interruptions. As a result, an increase in fusion protein with activity of the reporter gene coding sequence can be detected.

In one embodiment, a nucleic acid construct comprises, in 5' to 3' order: (i) a fragment of the nucleic acid residues of exon 8 of SMN; and (ii) a reporter gene coding sequence lacking a start codon, wherein the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and a stop codon is upstream of the reporter gene in the mRNA transcript. In certain embodiments, the fragment of the nucleic acid residues of exon 8 of SMN consists of the first 3, 5, 7, or 9 nucleotides from the 5' end of exon 8 of SMN. In other embodiments, the fragment of the nucleic acid residues of exon 8 of SMN consists of the first 11, 13, 15, 17, or 19 nucleotides from the 5' end of exon 8 of SMN. In a specific embodiment, the fragment of the nucleic acid residues of exon 8 of SMN consists of the first 21 or 23 nucleotides from the 5' end of exon 8 of SMN. In certain embodiments, the nucleic acid construct comprises a start codon upstream (5') to the fragment of the nucleic acid residues of exon 8 of SMN. In accordance with such embodiments, the first start codon and the stop codon upstream of the reporter gene coding sequence are in the same contiguous open reading frame without any interruption by, e.g., a stop codon.

In another embodiment, a nucleic acid construct comprises, in 5' to 3' order: (a) a fragment of the nucleic acid residues of exon 7 of SMN; (b) a fragment of the nucleic acid residues of exon 8 of SMN; and (c) a reporter gene coding sequence lacking a start codon, wherein: (i) in the mRNA transcript transcribed from the nucleic acid construct, the region of the mRNA transcript corresponding to the fragment of the nucleic acid residues of exon 7 of SMN does not contain a stop codon; (ii) the fragment of the nucleic acid residues of exon 7 of SMN comprises any number of nucleotides of exon 7 of SMN so long as in the mRNA transcript transcribed from the nucleic acid construct the open reading frames of the fragment of the nucleic acid residues of exon 7 of SMN and the fragment of the nucleic acid residues of exon 8 of SMN are in frame with each other; and (iii) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In another embodiment, the fragment of the nucleic acid residues of SMN consists of the first 23 nucleotides from the 5' end of exon 8 of SMN. In certain embodiments, the nucleic acid construct comprises a start codon upstream (5') to the fragment of the nucleic acid residues of exon 7 of SMN. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon, (b) a fragment of the nucleic acid residues of exon 7 of SMN; (c) a fragment of the nucleic acid residues of exon 8 of SMN; and (d) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); and (ii) the fragment of the nucleic acid residues of exon 7 of SMN comprises any number of nucleotides of exon 7 of SMN so long as in the mRNA transcript transcribed from the nucleic acid construct the first start codon and the stop codon upstream of the reporter gene coding sequence are maintained in the same contiguous open reading frame without any interruption by, e.g., stop codon.

In another embodiment, a nucleic acid construct comprises, in 5' to 3' order: (a) the nucleic acid residues of exon 6 of SMN or a fragment thereof; (b) a fragment of the nucleic acid residues of exon 7 of SMN; (c) a fragment of the nucleic acid residues of exon 8 of SMN; and (d) a reporter gene coding sequence lacking a start codon, wherein: (i) in the mRNA transcript transcribed from the nucleic acid construct, the regions of the mRNA transcripts corresponding to the fragments of the nucleic acid residues of exon 6 and exon 7 of SMN do not contain a stop codon; (ii) the fragment of the nucleic acid residues of exon 6 of SMN and the fragment of the nucleic acid residues of exon 7 of SMN each comprise any number of nucleotides of exon 6 of SMN and exon 7 of SMN, respectively, so long as in the mRNA transcript transcribed from the nucleic acid construct the open reading frame of the fragment of the nucleic acid residues of exon 6 of SMN and the open reading frame of the fragment of the nucleic acid residues of exon 8 of SMN are in frame with one another; (iii) the open reading frame of the nucleic acid residues of exon 6 of SMN, the open reading frame of the fragment of the nucleic acid residues of exon 7 of SMN, and the open reading frame of the nucleic acid residues of the nucleic acid residues of exon 8 of SMN are in frame with one another in the mRNA transcript from the nucleic acid construct; and (iv) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter coding sequence). In one embodiment, the fragment of the nucleic acid residues of exon 8 of SMN consists of the first 21 or 23 nucleotides from the 5' end of exon 8 of SMN. In certain embodiments, an internal start codon (e.g., ATG) in the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) a start codon, (b) the nucleic acid residues of exon 6 of SMN or a fragment thereof; (c) a fragment of the nucleic acid residues of exon 7 of SMN; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter coding sequence); and (ii) the fragment of the nucleic acid residues of exon 6 of SMN and the fragment of the nucleic acid residues of exon 7 of SMN each comprise any number of nucleotides of exon 6 of SMN and exon 7 of SMN, respectively, so long as in the mRNA transcript transcribed from the nucleic acid construct the first start codon and the stop codon upstream of the reporter gene coding sequence are maintained in the same contiguous open reading frame without any interruption by, e.g., a stop codon.

In another embodiment, a nucleic acid construct comprises, in 5' to 3' order: (a) a fragment of the nucleic acid residues of exon 7 of SMN; (b) the nucleic acid residues of intron 7 of SMN or a fragment thereof, wherein the fragment of the nucleic acid residues of intron 7 comprises any number of nucleotides of intron 7 of SMN required for a functional, minimum intron; (c) a fragment of the nucleic acid residues of exon 8 of SMN; and (d) a reporter gene coding sequence lacking a start codon, wherein: (i) in the mRNA transcript transcribed from the nucleic acid construct, the region of the mRNA transcript corresponding to the fragment of the nucleic acid residues of exon 7 of SMN does not contain a stop codon; (ii) the fragment of the nucleic acid residues of exon 7 of SMN comprises a minimum of the nucleotides of exon 7 of SMN required for splicing and in the mRNA transcript transcribed from the nucleic acid construct the open reading frame of the fragment of the nucleic acid residues of exon 7 of SMN and the open reading frame of the fragment of the nucleic acid residues of exon 8 of SAN are in frame with each other; and (iii) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In another specific embodiment, the fragment of the nucleic acid residues of exon 7 of SMN comprises the first two nucleotides from the 3' end of exon 7 of SMN (i.e., nucleotide residues 53 and 54 from the 5' end of exon 7 of SMN). In a specific embodiment, the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN). In certain embodiments, the nucleic acid construct comprises a start codon upstream (5') to the fragment of the nucleic acid residues of exon 7 of SMN. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) a start codon; (b) a fragment of the nucleic acid residues of exon 7 of SMN; (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); and (ii) the fragment of the nucleic acid residues of exon 7 of SMN comprises a minimum number of the nucleotides of exon 7 of SMN required for splicing and that number of nucleotides maintains the start codon and the stop codon upstream of the reporter gene coding sequence in the same contiguous open reading frame without any interruption by, e.g., stop codon.

In another embodiment, a nucleic acid construct comprises, in 5' to 3' order: (a) the nucleic acid residues of exon 6 of SAN or a fragment thereof; (b) a fragment of the nucleic acid residues of exon 7 of SMN; (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) in the mRNA transcript transcribed from the nucleic acid construct, the regions of the mRNA transcript corresponding to the fragments of the nucleic acid residues of exon 6 and exon 7 of SMN do not contain a stop codon; (ii) the fragment of the nucleic acid residues of exon 6 of SMN comprises any number of nucleotides of exon 6 of SMN so long as in the mRNA transcript transcribed from the nucleic acid construct the open reading frame of the fragment of the nucleic acid residues of exon 6 of SMN and the open reading frame of the fragment of the nucleic acid residues of exon 8 of SMN are in frame with each other; (iii) the fragment of the nucleic acid residues of exon 7 of SMN comprises a minimum of the nucleotides of exon 7 of SMN required for splicing and in the mRNA transcript transcribed from the nucleic acid construct the open reading frame of the fragment of the nucleic acid residues of exon 7 of SMN, the open reading frame of the nucleic acid residues of exon 6 of SMN or a fragment thereof, and the open reading frame of the fragment of exon 8 of SMN are in frame with each other; and (iv) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In another specific embodiment, the fragment of the nucleic acid residues of exon 7 of SMN comprises the first two nucleotides from the 3' end of exon 7 of SMN (i.e., nucleotide residues 53 and 54 from the 5' end of exon 7 of SMN). In another specific embodiment, the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN). In certain embodiments, an internal start codon (e.g., ATG) of the nucleic acid residues of exon 6 of SMN or a fragment thereof is used as a start codon for the nucleic acid construct. In some embodiments, the nucleic acid construct comprises a start codon upstream (5') to the nucleic acid residues of exon 6 of SMN or a fragment thereof. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) a start codon; (b) the nucleic acid residues of exon 6 of SMN or a fragment thereof; (c) a fragment of the nucleic acid residues of exon 7 of SMN; (d) the nucleic acid residues of intron 7 of SMN or a fragment thereof, wherein the fragment of the nucleic acid residues of intron 7 comprises any number of nucleotides of intron 7 of SMN required for a functional, minimum intron; (e) a fragment of the nucleic acid residues of exon 8 of SMN; and (f) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); (ii) the fragment of the nucleic acid residues of exon 6 of SMN comprises any number of nucleotides of exon 6 of SMN so long as in the mRNA transcript transcribed from the nucleic acid construct the first start codon and the stop codon upstream of the reporter gene coding sequence are maintained in the same contiguous open reading frame without any interruption by, e.g., stop codon; and (iii) the fragment of the nucleic acid residues of exon 7 of SMN comprises a minimum number of the nucleotides of exon 7 of SMN required for splicing and that number of nucleotides maintains the first start codon and the stop codon upstream of the reporter gene coding sequence in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of intron 6 of SMN or a fragment thereof, wherein the fragment of the nucleic acid residues of intron 6 of SMN comprises any number of nucleotides of intron 6 of SMN required for a functional, minimum intron; (c) a fragment of the nucleic acid residues of exon 7 of SMN; (d) the nucleic acid residues of intron 7 of SMN or a fragment thereof, wherein the fragment of the nucleic acid residues of intron 7 comprises any number of nucleotides of intron 7 of SMN required for a functional, minimum intron; (e) a fragment of the nucleic acid residues of exon 8 of SMN; and (f) a reporter gene coding sequence lacking a start codon, wherein: (i) in the mRNA transcript transcribed from the nucleic acid construct, the regions of the mRNA transcript corresponding to the fragments of the nucleic acid residues of exon 6 and exon 7 of SMN do not contain a stop codon; (ii) the fragment of the nucleic acid residues of exon 6 of SMN comprises a minimum of the nucleotides of exon 6 of SMN required for splicing and in the mRNA transcript transcribed from the nucleic acid construct the open reading frame of the fragment of the nucleic acid residues of exon 6 of SMN and the fragment of the nucleic acid residues of exon 8 of SMN are in frame with each other; (iii) the fragment of the nucleic acid residues of exon 7 of SMN comprises a minimum of the nucleotides of exon 7 of SMN required for splicing and in the mRNA transcript transcribed from the nucleic acid construct the open reading frame of the fragment of the nucleic acid residues of exon 7 of SMN, the open reading frame of the nucleic acid residues of exon 6 of SMN or a fragment thereof, and the open reading frame of the fragment of exon 8 of SMN are in frame with each other; and (iv) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In another specific embodiment, the fragment of the nucleic acid residues of exon 7 of SMN comprises a minimum of the first nucleotide from the 5' end of exon 7 of SMN and the first two nucleotides from the 3' end of exon 7 of SMN (i.e., nucleotide residues 53 and 54 from the 5' end of exon 7 of SMN). In another specific embodiment, the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN). In certain specific embodiments, the fragment of the nucleic acid residues of exon 6 of SMN comprises a minimum of the first two nucleotides from the 3' end of exon 6 of SMN. In other embodiments, the fragment of the nucleic acid residues of exon 6 of SMN comprises a minimum of the first three nucleotides from the 3' end of exon 6 of SMN. In certain embodiments, an internal start codon (e.g., ATG) of the nucleic acid residues of exon 6 of SMN or a fragment thereof is used as a start codon for the nucleic acid construct. In some embodiments, the nucleic acid construct comprises a start codon upstream (5') to the nucleic acid residues of exon 6 of SMN or a fragment thereof. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) a start codon; (b) the nucleic acid residues of exon 6 of SMN or a fragment thereof; (c) the nucleic acid residues of intron 6 of SMN or a fragment thereof, wherein the fragment of the nucleic acid residues of intron 6 of SMN comprises any number of nucleotides of intron 6 of SMN required for a functional, minimum intron; (d) a fragment of the nucleic acid residues of exon 7 of SMN; (e) the nucleic acid residues of intron 7 of SMN or a fragment thereof, wherein the fragment of the nucleic acid residues of intron 7 comprises any number of nucleotides of intron 7 of SMN required for a functional, minimum intron; (f) a fragment of the nucleic acid residues of exon 8 of SMN; and (g) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); and (ii) the fragment of the nucleic acid residues of exon 6 of SMN and the fragment of the nucleic acid residues of exon 7 of SMN each comprise a minimum number of the nucleotides of exon 6 of SMN and exon 7 of SMN, respectively, required for splicing and that number of nucleotides maintains the first start codon and the stop codon upstream of the reporter gene coding sequence in the same contiguous open reading frame without any interruption by, e.g., a stop codon.

In another embodiment, a nucleic acid construct comprises, in 5' to 3' order: (a) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (b) a fragment of the nucleic acid residues of exon 8 of SMN; and (c) a reporter gene coding sequence lacking a start codon, wherein: (i) in the mRNA transcript transcribed from the nucleic acid construct, the open reading frame of the nucleic acid residues of exon 7 of SMN and the open reading frame of the fragment of the nucleic acid residues of exon 8 of SMN are in frame with each other; and (ii) the reporter gene coding sequence is fused to the fragment of the nucleic acid residues of exon 8 of SMN such that the open reading frames of the reporter gene and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In another embodiment, the fragment of the nucleic acid residues of SMN consists of the first 23 nucleotides from the 5' end of exon 8 of SMN. In another specific embodiment, a single nucleotide residue is inserted after the 48th nucleotide residue from the 5' end of exon 7 of SMN (i.e., before the 6th nucleotide from the 3' end of exon 7 of SMN). In certain embodiments, the nucleic acid construct comprises a start codon upstream (5') to the nucleic acid residues of exon 7 of SMN. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon, (b) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (c) a fragment of the nucleic acid residues of exon 8 of SMN; and (d) a reporter gene coding sequence lacking a start codon, wherein: (i) the reporter gene coding sequence is fused to the fragment of the nucleic acid residues of exon 8 of SMN such that the first codon of the reporter gene and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); and (ii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (c) a fragment of the nucleic acid residues of exon 8 of SMN; and (d) a reporter gene coding sequence lacking a start codon, wherein: (i) the fragment of the nucleic acid residues of exon 6 of SMN comprises any number of nucleotides of exon 6 of SMN so long as in the mRNA transcript transcribed from the nucleic acid construct the open reading frame of the fragment of the nucleic acid residues of exon 6 of SMN and the open reading frame of the fragment of the nucleic acid residues of exon 8 of SMN are in frame with one another; (ii) the open reading frame of the nucleic acid residues of exon 6 of SMN, the open reading frame of the nucleic acid residues of exon 7 of SMN, and the open reading frame of the fragment of exon 8 of SMN are in frame with one another in the mRNA transcript transcribed from the nucleic acid construct; (iii) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN. In a specific embodiment, the fragment of the nucleic acid residues of exon 8 of SMN consists of the first 21 or 23 nucleotides from the 5' end of exon 8 of SMN. In another specific embodiment, a single nucleotide residue is inserted after the 48th nucleotide residue from the 5' end of exon 7 of SMN (i.e., before the 6th nucleotide from the 3' end of exon 7 of SMN). In certain embodiments, an internal start codon (e.g., ATG) in the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) the nucleic acid residues of exon 6 of SMN or a fragment thereof; (c) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SAM (i.e., upstream of the reporter gene coding sequence); and (ii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (b) the nucleic acid residues of intron 7 of SMN or a fragment thereof, wherein the fragment of the nucleic acid residues of intron 7 comprises any number of nucleotides of intron 7 of SMN required for a functional, minimum intron; (c) a fragment of the nucleic acid residues of exon 8 of SMN; and (d) a reporter gene coding sequence lacking a start codon, wherein: (i) the open reading frame of the nucleic acid residues of exon 7 of SMN and the open reading frame of the nucleic acid residues of exon 8 of SMN are in frame with each other in the mRNA transcript transcribed from the nucleic acid construct; and (ii) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In another specific embodiment, a single nucleotide residue is inserted after the 48th nucleotide residue from the 5' end of exon 7 of SMN (i.e., before the 6th nucleotide from the 3' end of exon 7 of SMN). In certain embodiments, the nucleic acid construct comprises a start codon upstream (5') to the nucleic acid residues of exon 7 of SMN. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); and (ii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) the fragment of exon 6 of SMN comprises any number of nucleotides of exon 6 of SMN so long as in the mRNA transcript transcribed from the nucleic acid construct the open reading frame of the fragment of the nucleic acid residues of exon 6 of SMN and the fragment of the nucleic acid residues of exon 8 of SMN are in frame with each other; (ii) the open reading frame of the nucleic acid residues of exon 6 of SMN, the open reading frame of the nucleic acid residues of exon 7 of SMN, and the open reading frame of the fragment of exon 8 of SMN are in frame with one another in the mRNA transcript transcribed from the nucleic acid construct; and (iii) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In another specific embodiment, a single nucleotide residue is inserted after the 48th nucleotide residue from the 5' end of exon 7 of SMN (i.e., before the 6th nucleotide from the 3' end of exon 7 of SMN). In certain embodiments, an internal start codon (e.g., ATG) of the nucleic acid residues of exon 6 of SMN or a fragment thereof is used as a start codon for the nucleic acid construct. In some embodiments, the nucleic acid construct comprises a start codon upstream (5') to the nucleic acid residues of exon 6 of SMN or a fragment thereof. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) the nucleic acid residues of exon 6 of SMN or a fragment thereof; (c) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (d) the nucleic acid residues of intron 7 of SMN or a fragment thereof, wherein the fragment of the nucleic acid residues of intron 7 comprises any number of nucleotides of intron 7 of SMN required for a functional, minimum intron; (e) a fragment of the nucleic acid residues of exon 8 of SMN; and (f) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); and (ii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of intron 6 of SMN or a fragment thereof, wherein the fragment of the nucleic acid residues of intron 6 of SMN comprises any number of nucleotides of intron 6 of SMN required for a functional, minimum intron; (c) the nucleic acid residues of exon 7 of SMN, wherein any number of nucleotides are inserted after the 48th nucleotide residue from the 5' end of exon 7 of SMN before the 6th nucleotide from the 3' end of exon 7 of SMN) as long as the native stop codon of exon 7 of SMN is inactivated and any additional stop codon is not generated; (d) the nucleic acid residues of intron 7 of SMN or a fragment thereof, wherein the fragment of the nucleic acid residues of intron 7 comprises any number of nucleotides of intron 7 of SMN required for a functional, minimum intron; (e) a fragment of the nucleic acid residues of exon 8 of SMN; and (1) a reporter gene coding sequence lacking a start codon, wherein: (i) the fragment of the nucleic acid residues of exon 6 of SMN comprises a minimum of the nucleotides of exon 6 of SMN required for splicing and in the mRNA transcript transcribed from the nucleic acid construct the open reading frame of the fragment of the nucleic acid residues of exon 6 of SMN and the fragment of the nucleic acid residues of exon 8 of SMN are in frame with each other; (ii) the open reading frame of the nucleic acid residues of exon 6 of SMN, the open reading frame of the nucleic acid residues of exon 7 of SMN, and the open reading frame of the fragment of the nucleic acid residues of exon 8 of SMN are in frame with one another in the mRNA transcript transcribed from the nucleic acid construct; and (iii) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In another specific embodiment, a single nucleotide residue is inserted after the 48th nucleotide residue from the 5' end of exon 7 of SMN (i.e., before the 6th nucleotide from the 3' end of exon 7 of SMN). In certain specific embodiments, the fragment of the nucleic acid residues of exon 6 of SMN comprises a minimum of the first two nucleotides from the 3' end of exon 6 of SMN. In other embodiments, the fragment of the nucleic acid residues of exon 6 of SMN comprises a minimum of the first three nucleotides from the 3' end of exon 6 of SMN. In certain embodiments, an internal start codon (e.g., ATG) of the nucleic acid residues of exon 6 of SMN or a fragment thereof is used as a start codon for the nucleic acid construct. In some embodiments, the nucleic acid construct comprises a start codon upstream (5') to the nucleic acid residues of exon 6 of SMN or a fragment thereof. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) the nucleic acid residues of exon 6 of SMN or a fragment thereof, wherein the fragment comprises a minimum number of nucleotides required for splicing; (c) the nucleic acid residues of intron 6 of SMN or a fragment thereof, wherein the fragment of the nucleic acid residues of intron 6 of SMN comprises any number of nucleotides of intron 6 of SMN required for a functional, minimum intron; (d) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (e) the nucleic acid residues of intron 7 of SMN or a fragment thereof, wherein the fragment of the nucleic acid residues of intron 7 comprises any number of nucleotides of intron 7 of SMN required for a functional, minimum intron; (f) a fragment of the nucleic acid residues of exon 8 of SMN; and (g) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); and (ii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) the nucleic acid residues of exon 7 of SMN, wherein a single guanine residue is inserted after the 48th nucleotide residue from the 5' end of exon 7 of SMN (i.e., before the 6th nucleotide from the 3' end of exon 7 of SMN); (b) the nucleic acid residues of intron 7 of SMN or a fragment thereof, wherein the fragment of the nucleic acid residues of intron 7 comprises any number of nucleotides of intron 7 of SMN required for a functional, minimum intron; (c) a fragment of the nucleic acid residues of exon 8 of SMN; and (d) a reporter gene coding sequence lacking a start codon, wherein: (i) the open reading frame of the nucleic acid residues of exon 7 of SMN and the open reading frame of the fragment of the nucleic acid residues of exon 8 of SMN are in frame with each other in the mRNA transcript transcribed from the nucleic acid construct; (ii) the reporter gene coding sequence is fused to the fragment of the nucleic acid residues of exon 8 of SMN such that the reporter gene coding sequence and the fragment are out of frame with each other in the mRNA transcript transcribed from the nucleic acid construct; and (iii) the production of the mRNA transcript generates a stop codon in the region of the mRNA transcript that corresponds to the fragment of the nucleic acid residues of exon 8 of SMN. In a specific embodiment, the fragment of the nucleic acid residues of exon 8 of SMN consists of the first 21 or 23 nucleotides from the 5' end of exon 8 of SMN. In another embodiment, the fragment of the nucleic acid residues of SMN consists of the first 23 nucleotides from the 5' end of exon 8 of SMN. In certain embodiments, the nucleic acid construct comprises a start codon upstream (5') to the nucleic acid residues of exon 7 of SMN. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) the nucleic acid residues of exon 7 of SMN, wherein a single guanine residue is inserted after the 48th nucleotide residue from the 5' end of exon 7 of SMN (i.e., before the 6th nucleotide from the 3' end of exon 7 of SMN); (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic, acid residues of exon 7 of SMN, wherein a single guanine residue is inserted after the 48th nucleotide residue from the 5' end of exon 7 of SMN (i.e., before the 6th nucleotide from the 3' end of exon 7 of SMN); (c) the nucleic acid residues of intron 7 of SMN or a fragment thereof, wherein the fragment of intron 7 of SMN comprises any number of nucleotides of intron 7 of SMN required for a functional, minimum intron; (d) a fragment of the nucleic acid residues of exon 8 of SMN; and (e) a reporter gene coding sequence lacking a start codon, wherein (i) the fragment of the nucleic acid residues of exon 6 of SMN comprises any number of nucleotides of exon 6 of SMN so long as in the mRNA transcript transcribed from the nucleic acid construct the open reading frame of the fragment of the nucleic acid residues of exon 6 of SMN and the open reading frame of the fragment of the nucleic acid residues of exon 8 of SMN are in frame with each other; (ii) the open reading frame of the nucleic acid residues of exon 6 of SMN, the open reading frame of the nucleic acid residues of exon 7 of SMN, and the open reading frame of the fragment of the nucleic acid residues of exon 8 of SMN are in frame with each other in the mRNA transcript transcribed from the nucleic acid construct; (iii) the reporter gene coding sequence is fused to the fragment of the nucleic acid residues of exon 8 of SMN such that the reporter gene coding sequence and the fragment are out of frame with each other in the mRNA transcript transcribed from the nucleic acid construct; and (iii) the production of the mRNA transcript generates a stop codon in the region of the mRNA transcript that corresponds to the fragment of the nucleic acid residues of exon 8 of SMN. In a specific embodiment, the fragment of the nucleic acid residues of exon 8 of SMN consists of the first 21 or 23 nucleotides from the 5' end of exon 8 of SMN. In certain embodiments, an internal start codon (e.g., ATG) in the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) the nucleic acid residues of exon 6 of SMN or a fragment thereof; (c) the nucleic acid residues of exon 7 of SMN, wherein a single guanine residue is inserted after the 48th nucleotide residue from the 5' end of exon 7 of SMN (i.e., before the 6th nucleotide from the 3' end of exon 7 of SMN); (d) the nucleic acid residues of intron 7 of SMN or a fragment thereof, wherein the fragment of intron 7 of SMN comprises any number of nucleotides of intron 7 of SMN required for a functional, minimum intron; (e) a fragment of the nucleic acid residues of exon 8 of SMN; and (f) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of intron 6 of SMN or a fragment thereof, wherein the fragment of the nucleic acid residues of intron 6 of SMN comprises any number of nucleotides of intron 6 required for a functional, minimum intron; (c) the nucleic acid residues of exon 7 of SMN, wherein a single guanine residue is inserted after the 48th nucleotide residue from the 5' end of exon 7 of SMN (i.e., before the 6th nucleotide from the 3' end of exon 7 of SMN); (d) the nucleic acid residues of intron 7 of SMN or a fragment thereof, wherein the fragment of intron 7 of SMN comprises any number of nucleotides of intron 7 of SMN required for a functional, minimum intron; (e) a fragment of the nucleic acid residues of exon 8 of SMN; and (1) a reporter gene coding sequence lacking a start codon, wherein (i) the fragment of the nucleic acid residues of exon 6 of SMN comprises a minimum of the nucleotides of exon 6 of SMN required for splicing and in the mRNA transcript transcribed from the nucleic acid construct the open reading frame of the fragment of the nucleic acid residues of exon 6 of SMN and the open reading frame of the fragment of the nucleic acid residues of exon 8 of SMN are in frame with each other; (ii) the open reading frame of the nucleic acid residues of exon 6 of SMN, the open reading frame of the nucleic acid residues of exon 7 of SMN, and the open reading frame of the fragment of the nucleic acid residues of exon 8 of SMN are in frame with each other in the mRNA transcript transcribed from the nucleic acid construct; (iii) the reporter gene coding sequence is fused to the fragment of the nucleic acid residues of exon 8 of SMN such that the reporter gene coding sequence and the fragment are out of frame with each other in the mRNA transcript transcribed from the nucleic acid construct; and (iv) the production of the mRNA transcript generates a stop codon in the region of the mRNA transcript that corresponds to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In certain specific embodiments, the fragment of the nucleic acid residues of exon 6 of SMN comprises a minimum of the first two nucleotides from the 3' end of exon 6 of SMN. In other embodiments, the fragment of the nucleic acid residues of exon 6 of SMN comprises a minimum of the first three nucleotides from the 3' end of exon 6 of SMN. In certain embodiments, an internal ATG in the nucleic acid residues of exon 6 of SMN or a fragment thereof is used as a start codon for the nucleic acid construct. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) the nucleic acid residues of exon 6 of SMN or a fragment thereof; (c) the nucleic acid residues of intron 6 of SMN or a fragment thereof, wherein the fragment of the nucleic acid residues of intron 6 of SMN comprises any number of nucleotides of intron 6 required for a functional, minimum intron; (d) the nucleic acid residues of exon 7 of SMN, wherein a single guanine residue is inserted after the 48th nucleotide residue from the 5' end of exon 7 of SMN (i.e., before the 6th nucleotide from the 3' end of exon 7 of SMN); (e) the nucleic acid residues of intron 7 of SMN or a fragment thereof, wherein the fragment of intron 7 of SMN comprises any number of nucleotides of intron 7 of SMN required for a functional, minimum intron; (f) a fragment of the nucleic acid residues of exon 8 of SMN; and (g) a reporter gene coding sequence lacking a start codon, wherein (i) the fragment of the nucleic acid residues of exon 6 of SMN comprises a minimum of the nucleotides of exon 6 of SMN required for splicing; (ii) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (iii) the production of the mRNA transcript generates a stop codon in the region of the mRNA transcript that corresponds to the fragment of the nucleic acid residues of exon 8 of SMN (i.e., upstream of the reporter gene coding sequence); and (iv) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) a minimum of one nucleotide; (b) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN) and wherein a single guanine residue is inserted into the fragment of the nucleic acid residues of exon 7 of SMN at the location that corresponds to the location in exon 7 of SMN that is after the 48th nucleotide from the 5' end of exon 7 of SMN; (c) the nucleic acid residues of intron 7 of SMN or a fragment thereof, wherein the fragment of the nucleic acid residues of intron 7 of SMN comprises any number of nucleotides of intron 7 required for a functional, minimum intron; (d) a fragment of the nucleic acid residues of exon 8 of SMN; and (e) a reporter gene coding sequence lacking a start codon, wherein (i) in the mRNA transcript transcribed from the nucleic acid construct, open reading of the fragment of the nucleic acid residues of exon 7 of SMN and the open reading frame of the fragment of the nucleic acid residues of exon 8 of SMN are in frame with each other; (ii) the reporter gene coding sequence is fused to the fragment of the nucleic acid residues of exon 8 of SMN such that the reporter gene coding sequence and the fragment are out of frame with each other in the mRNA transcript transcribed from the nucleic acid construct; and (iii) the production of the mRNA transcript generates a stop codon in the region of the mRNA transcript that corresponds to the fragment of the nucleic acid residues of exon 8 of SMN. In a specific embodiment, the fragment of the nucleic acid residues of exon 8 of SMN consists of the first 21 or 23 nucleotides from the 5' end of exon 8 of SMN. In certain embodiments, the nucleic acid construct comprises a start codon upstream (5') to the minimum of one nucleotide. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) a minimum of one nucleotide; (c) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN) and wherein a single guanine residue is inserted into the fragment of the nucleic acid residues of exon 7 of SMN at the location that corresponds to the location in exon 7 of SMN that is after the 48th nucleotide from the 5' end of exon 7 of SMN; (d) the nucleic acid residues of intron 7 of SMN or a fragment thereof, wherein the fragment of the nucleic acid residues of intron 7 of SMN comprises any number of nucleotides of intron 7 required for a functional, minimum intron; (e) a fragment of the nucleic acid residues of exon 8 of SMN; and (f) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN), wherein a single guanine residue is inserted into the fragment of the nucleic acid residues of exon 7 of SMN at the location that corresponds to the location in exon 7 of SMN that is after the 48th nucleotide from the 5' end of exon 7 of SMN, and wherein the fragment of the nucleic acid residues of exon 7 of SMN comprises any number of nucleotides of exon 7 required for splicing; (b) the nucleic acid residues of intron 7 of SMN or a fragment thereof, wherein the fragment of the nucleic acid residues of intron 7 of SMN comprises any number of nucleotides of intron 7 required for a functional, minimum intron; (c) a fragment of the nucleic acid residues of exon 8 of SMN; and (d) a reporter gene coding sequence lacking a start codon, wherein (i) in the mRNA transcript transcribed from the nucleic acid construct, open reading of the fragment of the nucleic acid residues of exon 7 of SMN and the open reading frame of the fragment of the nucleic acid residues of exon 8 of SMN are in frame with each other; (ii) the reporter gene coding sequence is fused to the fragment of the nucleic acid residues of exon 8 of SMN such that the reporter gene coding sequence and the fragment are out of frame with each other in the mRNA transcript transcribed from the nucleic acid construct; and (iii) the production of the mRNA transcript generates a stop codon in the region of the mRNA transcript that corresponds to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In certain embodiments, the nucleic acid construct comprises a start codon upstream (5') to the fragment of the nucleic acid residues of exon 7 of SMN. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN), wherein a single guanine residue is inserted into the fragment of the nucleic acid residues of exon 7 of SMN at the location that corresponds to the location in exon 7 of SMN that is after the 48th nucleotide from the 5' end of exon 7 of SMN, and wherein the fragment of the nucleic acid residues of exon 7 of SMN comprises any number of nucleotides of exon 7 required for splicing; (c) the nucleic acid residues of intron 7 of SMN or a fragment thereof; wherein the fragment of the nucleic acid residues of intron 7 of SMN comprises any number of nucleotides of intron 7 required for a functional, minimum intron; (d) a fragment of the nucleic acid residues of exon 8 of SMN; and (e) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon.

In a specific embodiment, a nucleic acid construct comprises, in 5' to 3' order: (a) a minimum of one nucleotide; (b) a fragment of the nucleic acid residues of exon 7 of SMN, wherein the fragment of the nucleic acid residues of exon 7 of SMN consists of the first six nucleotides from the 3' end of exon 7 of SMN (i.e., nucleotide residues 49 to 54 from the 5' end of exon 7 of SMN) and wherein a single guanine residue is inserted upstream (5') of the fragment of the nucleic acid residues of exon 7 of SMN; (c) the nucleic acid residues of intron 7 of SMN or a fragment thereof, wherein the fragment of the nucleic acid residues of intron 7 of SMN comprises any number of nucleotides of intron 7 required for a functional, minimum intron; (d) a fragment of the nucleic acid residues of exon 8 of SMN; and (e) a reporter gene coding sequence lacking a start codon, wherein (i) in the mRNA transcript transcribed from the nucleic acid construct, open reading of the fragment of the nucleic acid residues of exon 7 of SMN and the open reading frame of the fragment of the nucleic acid residues of exon 8 of SMN are in frame with each other; (ii) the reporter gene coding sequence is fused to the fragment of the nucleic acid residues of exon 8 of SMN such that the reporter gene coding sequence and the fragment are out of frame with each other in the mRNA transcript transcribed from the nucleic acid construct; and (iii) the production of the mRNA transcript generates a stop codon in the region of the mRNA transcript that corresponds to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In certain embodiments, the nucleic acid construct comprises a start codon upstream (5') to the minimum one nucleotide. In accordance with such embodiments, the first start codon and the stop codon upstream of the reporter gene coding sequence in the mRNA transcript are in the sane contiguous open reading frame without any interruption by, e.g., a stop codon.

In a specific embodiment, a nucleic acid construct comprises, in 5' to 3' order: (a) a start codon; (b) a minimum of one nucleotide; (c) a fragment of the nucleic acid residues of exon 7 of SMN, wherein the fragment of the nucleic acid residues of exon 7 of SMN consists of the first six nucleotides from the 3' end of exon 7 of SMN (i.e., nucleotide residues 49 to 54 from the 5' end of exon 7 of SMN) and wherein a single guanine residue is inserted upstream (5') of the fragment of the nucleic acid residues of exon 7 of MIN; (d) the nucleic acid residues of intron 7 of SMN or a fragment thereof, wherein the fragment of the nucleic acid residues of intron 7 of SMN comprises any number of nucleotides of intron 7 required for a functional, minimum intron; (e) a fragment of the nucleic acid residues of exon 8 of SMN; and (f) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon.

In a specific embodiment, a nucleic acid construct comprises, in 5' to 3' order: (a) a fragment of the nucleic acid residues of exon 7 of SMN, wherein the fragment of the nucleic acid residues of exon 7 of SMN consists of the first six nucleotides from the 3' end of exon 7 of SMN (i.e., nucleotide residues 49 to 54 from the 5' end of exon 7 of SMN), wherein a single guanine residue is inserted upstream (5') of the fragment of the nucleic acid residues of exon 7 of SMN, and wherein the fragment of the nucleic acid residues of exon 7 of SMN comprises any number of nucleotides of exon 7 required for splicing; (b) the nucleic acid residues of intron 7 of SMN or a fragment thereof, wherein the fragment of the nucleic acid residues of intron 7 of SMN comprises any number of nucleotides of intron 7 required for a functional, minimum intron; (c) a fragment of the nucleic acid residues of exon 8 of SMN; and (d) a reporter gene coding sequence lacking a start codon, wherein (i) in the mRNA transcript transcribed from the nucleic acid construct, open reading of the fragment of the nucleic acid residues of exon 7 of SMN and the open reading frame of the fragment of the nucleic acid residues of exon 8 of SMN are in frame with each other; (ii) the reporter gene coding sequence is fused to the fragment of the nucleic acid residues of exon 8 of SMN such that the reporter gene coding sequence and the fragment are out of frame with each other in the mRNA transcript transcribed from the nucleic acid construct; and (iii) the production of the mRNA transcript generates a stop codon in the region of the mRNA transcript that corresponds to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In certain embodiments, the nucleic acid construct comprises a start codon upstream (5') to the fragment of the nucleic acid residues of exon 7 of SMN. In accordance with such embodiments, the first start codon and the stop codon upstream of the reporter gene coding sequence in the mRNA transcript are in the same contiguous open reading frame without any interruption by, e.g., a stop codon.

In a specific embodiment, a nucleic acid construct comprises, in 5' to 3' order: (a) a start codon; (b) a fragment of the nucleic acid residues of exon 7 of SMN, wherein the fragment of the nucleic acid residues of exon 7 of SMN consists of the first six nucleotides from the 3' end of exon 7 of SMN (i.e., nucleotide residues 49 to 54 from the 5' end of exon 7 of SMN), wherein a single guanine residue is inserted upstream (5') of the fragment of the nucleic acid residues of exon 7 of SMN, and wherein the fragment of the nucleic acid residues of exon 7 of SMN comprises any number of nucleotides of exon 7 required for splicing; (c) the nucleic acid residues of intron 7 of SMN or a fragment thereof, wherein the fragment of the nucleic acid residues of intron 7 of SMN comprises any number of nucleotides of intron 7 required for a functional, minimum intron; (d) a fragment of the nucleic acid residues of exon 8 of SMN; and (e) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN) and wherein a single guanine residue is inserted into the fragment of the nucleic acid residues of exon 7 of SMN at the location that corresponds to the location in exon 7 of SMN that is after the 48th nucleotide from the 5' end of exon 7 of SMN; (c) the nucleic acid residues of intron 7 of SMN or a fragment thereof, wherein the fragment of the nucleic acid residues of intron 7 of SMN comprises any number of nucleotides of intron 7 required for a functional, minimum intron; (d) a fragment of the nucleic acid residues of exon 8 of SMN; and (e) a reporter gene coding sequence lacking a start codon, wherein (i) the fragment of the nucleic acid residues of exon 6 of SMN comprises any number of nucleotides of exon 6 of SMN so long as in the mRNA transcript transcribed from the nucleic acid construct the open reading frame of the fragment of the nucleic acid resides of exon 6 of SMN, the open reading frame of the fragment of the nucleic acid residues of exon 7 of SMN and the open reading frame of the fragment of the nucleic acid residues of exon 8 of SMN are in frame with each other; (ii) the open reading frame of the nucleic acid residues of exon 6 of SMN, the open reading frame of the fragment of the nucleic acid residues of exon 7 of SMN, and the open reading frame of the fragment of the nucleic acid residues of exon 8 of SMN are in frame with each other in the mRNA transcript transcribed from the nucleic acid construct; (iii) the reporter gene coding sequence is fused to the fragment of the nucleic acid residues of exon 8 of SMN such that the reporter gene coding sequence and the fragment are out of frame with each other in the mRNA transcript transcribed from the nucleic acid construct; and (iv) the production of the mRNA transcript generates a stop codon in the region of the mRNA transcript that corresponds to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In certain embodiments, an internal start codon (e.g., ATG) in the nucleic acid residues of exon 6 of SMN or a fragment thereof is used as a start codon for the nucleic acid construct. In some embodiments, the nucleic acid construct comprises a start codon upstream (5') to the nucleic acid residues of exon 6 of SMN or a fragment thereof. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) the nucleic acid residues of exon 6 of SMN or a fragment thereof; (c) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN) and wherein a single guanine residue is inserted into the fragment of the nucleic acid residues of exon 7 of SMN at the location that corresponds to the location in exon 7 of SMN that is after the 48th nucleotide from the 5' end of exon 7 of SMN; (d) the nucleic acid residues of intron 7 of SMN or a fragment thereof, wherein the fragment of the nucleic acid residues of intron 7 of SMN comprises any number of nucleotides of intron 7 required for a functional, minimum intron; (e) a fragment of the nucleic acid residues of exon 8 of SMN; and (f) a reporter gene coding sequence lacking a start codon, wherein (i) the reporter gene coding sequence is fused to the fragment of the nucleic acid residues of exon 8 of SMN such that the first codon of the reporter gene coding sequence and the first codon fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of intron 6 of SMN or a fragment thereof, wherein the fragment of the nucleic acid residues of SMN comprises any number of nucleotides of introit 6 of SMN for a functional, minimum intron; (c) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN) and wherein a single guanine residue is inserted into the fragment of the nucleic acid residues of exon 7 of SMN at the location that corresponds to the location in exon 7 of SMN that is after the 48th nucleotide from the 5' end of exon 7 of SMN; (d) the nucleic acid residues of intron 7 of SMN or a fragment thereof, wherein the fragment of the nucleic acid residues of intron 7 of SMN comprises any number of nucleotides of intron 7 required for a functional, minimum intron; (e) a fragment of the nucleic acid residues of exon 8 of SMN; and (f) a reporter gene coding sequence lacking a start codon, wherein (i) the fragment of the nucleic acid residues of exon 6 of SMN comprises a minimum of the nucleotides of exon 6 of SMN required for splicing and in the mRNA transcript transcribed from the nucleic acid construct the open reading frame of the fragment of the nucleic acid resides of exon 6 of SMN, the open reading frame of the fragment of the nucleic acid residues of exon 7 of SMN and the open reading frame of the fragment of the nucleic acid residues of exon 8 of SMN are in frame with each other; (ii) the open reading frame of the nucleic acid residues of exon 6 of SMN, the open reading frame of the fragment of the nucleic acid residues of exon 7 of SMN, and the open reading frame of the fragment of the nucleic acid residues of exon 8 of SMN are in frame with each other in the mRNA transcript transcribed from the nucleic acid construct; (iii) the reporter gene coding sequence is fused to the fragment of the nucleic acid residues of exon 8 of SMN such that the reporter gene coding sequence and the fragment are out of frame with each other in the mRNA transcript transcribed from the nucleic acid construct; and (iv) the production of the mRNA transcript generates a stop codon in the region of the mRNA transcript that corresponds to the fragment of the nucleic acid residues of exon 8 of SMN (i.e., upstream of the reporter gene coding sequence). In a specific embodiment, the fragment of the nucleic acid residues of exon 8 of SPIN consists of the first 21 or 23 nucleotides from the 5' end of exon 8 of SMN. In another specific embodiment, the fragment of the nucleic acid residues of exon 7 of SMN comprises a minimum of the first nucleotide from the 5' end of exon 7 of SMN and the first two nucleotides from the 3' end of exon 7 of SMN (i.e., nucleotide residues 53 and 54 from the 5' end of exon 7 of SMN). In another specific embodiment, the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN). In another specific embodiment, the fragment of exon 6 of SMN comprises a minimum of the first two nucleotides from the 3' end of exon 6 of SMN. In certain embodiments, an internal start codon (e.g., ATG) in the nucleic acid residues of exon 6 of SMN or a fragment thereof is used as a start codon for the nucleic acid construct. In some embodiments, the nucleic acid construct comprises a start codon upstream (5') to the nucleic acid residues of exon 6 of SMN or a fragment thereof. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) start codon; (b) the nucleic acid residues of exon 6 of SMN or a fragment thereof; (c) the nucleic acid residues of intron 6 of SMN or a fragment thereof, wherein the fragment of the nucleic acid residues of SMN comprises any number of nucleotides of intron 6 of SMN for a functional, minimum intron; (d) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN) and wherein a single guanine residue is inserted into the fragment of the nucleic acid residues of exon 7 of SMN at the location that corresponds to the location in exon 7 of SMN that is after the 48th nucleotide from the 5' end of exon 7 of SMN; (e) the nucleic acid residues of intron 7 of SMN or a fragment thereof, wherein the fragment of the nucleic acid residues of intron 7 of SMN comprises any number of nucleotides of intron 7 required for a functional, minimum intron; (f) a fragment of the nucleic acid residues of exon 8 of SMN; and (g) a reporter gene coding sequence lacking a start codon, wherein (i) the fragment of the nucleic acid residues of exon 6 of SMN comprises a minimum of the nucleotides of exon 6 of SMN required for splicing; (ii) the reporter gene coding sequence is fused to the fragment of the nucleic acid residues of exon 8 of SMN such that the first codon of the reporter gene coding sequence and the first codon fragment are out of frame with each other in the mRNA transcript transcribed from the nucleic acid construct; (iii) the production of the mRNA transcript generates a stop codon in the region of the mRNA transcript that corresponds to the fragment of the nucleic acid residues of exon 8 of SMN (i.e., upstream of the reporter gene coding sequence); and (iv) in the mRNA transcript transcribed from the nucleic acid construct, the first start codon and the stop codon upstream from the reporter gene coding sequence are in the same contiguous open reading frame without any interruption by, e.g., a stop codon.

In another aspect, the compounds that are identified or validated in accordance with the methods described herein may be used to produce a stabilized SMNΔEx7 protein in a human subject in need thereof, and thus may be used to treat SMA in a human subject in need thereof.

In one embodiment, presented herein is a method for producing a stabilized SMNΔEx7 protein in a human subject in need thereof, comprising administering to the human subject an effective amount of a compound or pharmaceutical composition thereof, wherein the compound in vitro or in cells increases the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment consists of the first 23 nucleotides from the 5' end of exon 8 of SMN; and (vi) a reporter gene coding sequence lacking a start codon, wherein the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and the nucleic acid residues of exons 6, 7, and 8 are in frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN. In one embodiment, the compound is a compound of Formula (I) or a form thereof. In another embodiment, the compound is a compound of Formula (II) or a form thereof. In another embodiment, the compound is a compound of Formula (Ia) or a form thereof. In another embodiment, the compound is a compound of Formula (IIa) or a form thereof. In a specific embodiment, the compound is Compound 1.

In one embodiment, the stabilized SMNΔEx7 protein comprises the amino acid sequence of SEQ ID NO:2, SEQ ID NO:3, SEQ ID NO:4, or SEQ ID NO:5. In another embodiment, the stabilized SMNΔEx7 protein comprises one, two, three or all of the amino acid sequences of SEQ ID NO:2, SEQ ID NO:3, SEQ ID NO:4, or SEQ ID NO:5. In another embodiment, the stabilized SMNΔEx7 protein comprises a combination of any one of the amino acid sequences of SEQ ID NO:2, SEQ ID NO:3, SEQ ID NO:4, or SEQ ID NO:5.

In another embodiment, described herein is a method for treating SMA in a human subject in need thereof, comprising administering to the human subject an effective amount of a compound or pharmaceutical composition thereof, wherein the compound in vitro or in cells increases the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment consists of the first 23 nucleotides from the 5' end of exon 8 of SMN; and (vi) a reporter gene coding sequence lacking a start codon, wherein the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and the nucleic acid residues of exons 6, 7, and 8 are in frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN. In one embodiment, the compound is a compound of Formula (I) or a form thereof. In another embodiment, the compound is a compound of Formula (II) or a form thereof. In another embodiment, the compound is a compound of Formula (Ia) or a form thereof. In another embodiment, the compound is a compound of Formula (IIa) or a form thereof. In a specific embodiment, the compound is Compound 1.

In another embodiment, a compound identified or validated in accordance with the methods described herein is used for the preparation of a medicament that produces a stabilized SMNΔEx7 protein, thereby treating SMA in a human subject in need thereof.

In another embodiment, described herein is the use of a compound for the preparation of a medicament for the treatment of SMA in a human subject in need thereof, wherein the compound enhances, in vitro or in cultured cells, the amount and/or activity of a fusion protein encoded by a nucleic acid construct described herein.

In one embodiment, treatment results in the ability or helps retain the ability for a human infant or a human toddler to sit up. In another embodiment, treatment results in the ability or helps retain the ability for a human infant, a human toddler, a human child or a human adult to stand up unaided. In another embodiment, treatment results in the ability or helps retain the ability for a human infant, a human toddler, a human child or a human adult to walk unaided.

In another aspect, described herein are antibodies that specifically bind to a stabilized SMNΔEx7 protein and the use of such antibodies to, e.g., detect the presence of a stabilized SMNΔEx7 protein.

Terminology

As used herein, the term "about" or "approximately," when used in conjunction with a number, refers to any number within 1, 5 or 10% of the referenced number.

As used herein, the terms "increase," "increases," and "increased," in the context of the amount or activity of a fusion protein refer, in some embodiments, to: (i) an increase of 0.5%, 1%, 1.5%, 2%, 5%, 10%, 20%, 30%, 40%, 50% or more; (ii) an increase of 1.5, 2, 3, 4, or 5 fold or more; or (iii) a statistically significant increase in the amount or activity of the fusion protein relative to a negative control.

As used herein, the term "statistically significant increase" refers to an increase that has a p value of less than 0.1, 0.05, 0.01, or 0.001.

As used herein, the term "not statistically significant increase" refers to an increase that has a p value of greater than 0.001, 0.01, 0.05, or 0.1.

As used herein, the term "naturally-occurring SMNΔEx7 protein" refers to the protein found in nature that is encoded by the SMN2 gene, which lacks amino acid residues encoded by exon 7 of SMN2 and includes amino acids encoded by exon 8 (the protein otherwise referred to as "SMNΔEx7;" SEQ ID NO:1).

As used herein, the term "stabilized SMNΔEx7 protein" refers to a protein translated from a mRNA transcribed from the SMN2 gene, wherein the protein has an increased abundance or half-life relative to naturally-occurring SMNΔEx7 protein as measured by, e.g., an immunoassay or after inhibiting translation using a protein synthesis inhibitor such as described in FIG. 3 of Mattis et al., *Neuroscience Letters,* 442(1):54-8 (which is incorporated by reference in its entirety). In one embodiment, the stabilized SMNΔEx7 protein is increased in abundance relative to the naturally-occurring SMNΔEx7 protein as measured by an assay known in the art, e.g., an immunoassay such as Western blot. In another embodiment, the stabilized SMNΔEx7 has an increased half-life relative to the naturally-occurring SMNΔEx7 protein as measured by an assay known in the art, e.g., after inhibiting translation using a protein synthesis inhibitor such as described in FIG. 3 of Mattis et al., *Neuroscience Letters,* 442(1):54-8 (which is incorporated by reference in its entirety). In another embodiment, the stabilized SMNΔEx7 protein is increased in abundance relative to the naturally-occurring SMNΔEx7 protein as measured by an assay known in the art, e.g., an immunoassay such as Western blot, and has an increased half-life relative to the naturally-occurring SMNΔEx7 protein as measured by an assay known in the art, e.g., after inhibiting translation using a protein synthesis inhibitor such as described in FIG. 3 of Mattis et al., *Neuroscience Letters,* 442(1):54-8 (which is incorporated by reference in its entirety).

In a specific embodiment, the stabilized SMNΔEx7 protein comprises one or more amino acid residues at the C-terminus that are not found in the C-terminus of the amino acid of the sequence SMNΔEx7 protein (SEQ ID NO:1). In another specific embodiment, the stabilized SMNΔEx7 protein comprises the amino acid sequence of SEQ ID NO:1 and one, two, three or more additional amino acids at the C-terminus. In another specific embodiment, the stabilized SMNΔEx7 protein comprises one, two or more, all, or a combination of any one of the amino acid sequences of SEQ ID NO:2, SEQ ID NO:3, SEQ ID NO:4, or SEQ ID NO:5.

As used herein, the term "compound," unless otherwise specified or clear from the context of the specification, refers to any agent being tested for its ability to cause ribosomal frameshifting and/or to produce a stabilized SMNΔEx7 protein, or is identified or validated as causing ribosomal frameshifting and/or producing a stabilized SMNΔEx7 protein using a nucleic acid construct described herein. In one embodiment, the term "compound" refers to a small molecule. In a specific embodiment, the term "compound" refers to a compound of Formula (I) or Formula (II) or a form thereof. In one embodiment, the term "compound" refers to a compound selected from Compound 1.

As used herein, the term "small molecule" and analogous terms include, but are not limited to, peptides, peptidomimetics, amino acids, amino acid analogs, polynucleotides, polynucleotide analogs, nucleotides, nucleotide analogs, other organic and inorganic compounds (i.e., including heteroorganic and organometallic compounds) and forms thereof having a molecular weight of less than about 10,000 grams per mole, or less than about 5,000 grams per mole, or less than about 1,000 grams per mole, or less than about 500 grams per mole, or less than about 100 grams per mole.

As used herein, the term "effective amount" in the context of a method of treating SMA in a human subject by administering a compound refers to the amount of a compound which has a therapeutic effect. Non-limiting examples of effective amounts of a compound are described below.

As used herein, the term "effective amount" in the context of a method for producing a stabilized SMNΔEx7 protein refers to the amount of a compound which is sufficient to produce an effective amount of the protein, e.g., an amount that has a therapeutic benefit.

As used herein, the term "in combination," in the context of the administration of a compound, refers to the administration of two or more compounds that produce a stabilized SMN- ΔEx7 protein, or the administration of one or more compounds that produce a stabilized SMNΔEx7 protein and one or more additional agents. The use of the term "in combination" does not restrict the order in which two or more of the instant compounds or one or more of said compounds and another agent are administered to a subject in need thereof. For example, a compound can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of another agent to a subject with SMA.

As used herein, the term "elderly human" refers to a human 65 years or older.

As used herein, the term "human adult" refers to a human that is 18 years or older.

As used herein, the term "human child" refers to a human that is 1 year to 18 years old.

As used herein, the term "human toddler" refers to a human that is 1 year to 3 years old.

As used herein, the term "human infant" refers to a newborn to 1 year old year human.

As used herein, the term "premature human infant" refers to a human infant born at less than 37 weeks of gestational age.

As used herein, the term "combination product" refers to a product comprising: (i) two or more compounds that produce a stabilized SMNΔEx7 protein; or (ii) one or more compounds that produce a stabilized SMNΔEx7 protein and one or more additional agents.

As used herein, the term "form" in the context of a compound refers to a compound isolated for use as a pharmaceutically acceptable salt, ester, hydrate, solvate, clathrate, polymorph, geometric isomer, racemate, enantiomer, diastereomer or tautomer.

As used herein, the italicized term "*SMN*," unless otherwise specified herein, refers to human SMN1 or human SMN2. Nucleic acid sequences for the human SMN1 and SMN2 are known in the art. See, e.g., GENBANK® Accession Nos. DQ894095, NM_000344, NM_022874, and BC062723 for nucleic acid sequences of human SMN1. For nucleic acid sequences of human SMN2, see, e.g., NM_022875, NM_022876, NM_022877, NM_017411, DQ894734 (Invitrogen, Carlsbad, Calif.), BC000908.2, and BC015308.1.

The SMN1 gene can be found on human chromosome 5 from approximately nucleotide 70,256,524 to approximately nucleotide 70,284,595 using Vega Gene ID: OTTHUMG00000099361 (see website for ensembl.org/Homo_sapiens/geneview?gene=OTTHUMG00000099361; db=vega) at cytogenetics location 5 of 13. See also GENBANK® Accession No. NC_000005, Build 36.3 for the sequence of human chromosome 5.

The approximate locations of exons 6, 7 and 8 and introns 6 and 7 of SMN1 on human chromosome 5 using Vega gene ID:
OTTHUMG00000099361 (see website for ensembl.org/Homo_sapiens/geneview?gene=OTTHUMG00000099361; db=vega) are as follows:

70,277,649-70,277,759 exon 6
70,277,760-70,283,523 intron 6
70,283,524-70,283,577 exon 7
70,283,578-70,284,021 intron 7
70,284,022-70,284,595 exon 8

In specific embodiments, the nucleotide sequences delineated above for exons 6, 7 and 8 and introns 6 and 7 of SMN1 are used in the nucleic acid constructs described herein. In other specific embodiments, the nucleotide sequences described in the example below for exons 6, 7 and 8 and introns 6 and 7 are used in the nucleic acid constructs described herein.

The SMN2 gene can be found on human chromosome 5 from approximately nucleotide 69,381,106 to approximately nucleotide 69,409,175 using Vega gene ID: OTTHUMG00000099389 (see website for ensembl.org/Homo_sapiens/geneview?gene=OTTHUMG00000099389; db=vega). See also, GENBANK® Accession No. NC_000005, Build 36.3 for the sequence of human chromosome 5.

The approximate locations of exons 6, 7 and 8 and introns 6 and 7 of SMN2 on human chromosome 5 using Vega gene ID: OTTHUMG00000099389 (see website for ensembl.org/Homo_sapiens/geneview?gene=OTTHUMG00000099389; db=vega) are as follows:

69,402,224-69,402,334 exon 6
69,402,335-69,408,103 intron 6
69,408,104-69,408,157 exon 7
69,408,158-69,408,601 intron 7
69,408,602-69,409,175 exon 8.

In specific embodiments, the nucleotide sequences delineated above for exons 6, 7 and 8 and introns 6 and 7 of SMN2 are used in the nucleic acid constructs described herein. In other specific embodiments, the nucleotide sequences of exons 6, 7 and 8 and introns 6 and 7 of SMN2 are used in the nucleic acid constructs described herein.

As used herein, the term "host cell" includes a particular subject cell transformed or transfected with an instant nucleic acid construct and the progeny or potential progeny of such a cell. Progeny of such a cell may not be identical to the parent cell transfected with the nucleic acid construct due to mutations or environmental influences that may occur in succeeding generations or integration of the nucleic acid construct into the host cell genome.

As used herein, the term "isolated," as it refers to a compound, means the physical state of a compound after being separated and/or purified from precursors and other substances found in a synthetic process (e.g., from a reaction mixture) or natural source or combination thereof according to a process or processes described herein or which are well known to the skilled artisan (e.g., chromatography, recrystallization and the like) in sufficient purity to be capable of characterization by standard analytical techniques described herein or well known to the skilled artisan. In a specific embodiment, the compound is at least 60% pure, at least 65% pure, at least 70% pure, at least 75% pure, at least 80% pure, at least 85% pure, at least 90% pure or at least 99% pure as assessed by techniques known to one of skill in the art.

As used herein, the term "isolated," as it refers to a nucleic acid, means the physical state of a nucleic acid after being separated and/or purified from precursors and other substances found in a synthetic process (e.g., from a reaction mixture) or natural source or combination thereof according to a process or processes described herein or which are well known to the skilled artisan in sufficient purity to be capable of characterization by standard analytical techniques described herein or well known to the skilled artisan.

In some embodiments, the term "fragment" refers to a nucleotide sequence comprising 2 or more nucleotides from a longer nucleotide sequence. In certain embodiments, the nucleotide sequences comprise 2 or more contiguous nucleotides from a longer nucleotide sequence.

In specific embodiments, a fragment of the nucleic acid residues of exon 8 of SMN permits removal of an intron via mRNA splicing and maintains the complete sequence of the mRNA fragment included (or encoded) in a nucleic acid construct. In one embodiment, a fragment of the nucleic acid residues of exon 8 comprises between 2 to 23 nucleic acid residues from the 5' terminus of exon 8 of SMN. In certain embodiments, a fragment of the nucleic acid residues of exon 8 of SMN comprises the first 2, 5, 8, 11, 14, 17, 20 or 23 nucleic acid residues of exon 8 of SMN. In a specific embodiment, the fragment of exon 8 of SMN comprises the first 23 nucleic acid residues of exon 8 of SMN. In another specific embodiment, a fragment of the nucleic acid residues of exon 8 of SMN comprises the first 21 nucleic acid residues of exon 8 of SMN. In an alternative embodiment, a fragment of the nucleic acid residues of exon 8 of SMN comprises more or fewer than the first 21 nucleic acid residues of exon 8 of SMN.

In some embodiments, the terms "nucleic acid" and "nucleotides" refer to deoxyribonucleotides, deoxyribonucleic acids, ribonucleotides, and ribonucleic acids, and polymeric forms thereof, and includes either single- or double-stranded forms. In certain embodiments, such terms include known analogues of natural nucleotides, for example, peptide nucleic acids ("PNA"s), that have similar binding properties as the reference nucleic acid. In some embodiments, nucleic acid refers to deoxyribonucleic acids (e.g., cDNA or DNA). In other embodiments, nucleic acid refers to ribonucleic acids (e.g., mRNA or pre-mRNA).

As used herein, the term "nucleic acid residues of exon 6 of SMN," unless otherwise specified herein, refers to a complete, intact, non-truncated nucleic acid sequence exon 6 of SMN1 or SMN2. In certain embodiments, a nucleic acid construct described herein comprises, in part, a complete, intact, non-truncated nucleic acid sequence of exon 6 of SMN1 or SMN2.

As used herein, the term "nucleic acid residues of intron 6 of SMN," unless otherwise specified herein, refers to a complete, intact, non-truncated nucleic acid sequence of intron 6 of SMN1 or SMN2. In certain embodiments, a nucleic acid construct described herein comprises, in part, a complete, intact, non-truncated nucleic acid sequence of intron 6 of SMN1 or SMN2.

As used herein, the term "nucleic acid residues of exon 7 of SMN," unless otherwise specified herein, refers to a complete, intact, non-truncated nucleic acid sequence of exon 7 of SMN1 or SMN2. In certain embodiments, a nucleic acid construct described herein comprises, in part, a complete, intact, non-truncated nucleic acid sequence of exon 7 of SMN1 or SMN2.

As used herein, the term "nucleic acid residues of intron 7 of SMN," unless otherwise specified herein, refers to a complete, intact, non-truncated nucleic acid sequence of intron 7 of SMN1 or SMN2. In certain embodiments, a nucleic acid construct described herein comprises, in part, a complete, intact, non-truncated nucleic acid sequence of intron 7 of SMN1 or SMN2.

As used herein, the term "nucleic acid residues of exon 8 of SMN," unless otherwise specified herein, refers to a complete, intact, non-truncated nucleic acid sequence of exon 8 of SMN1 or SMN2.

As used herein, the term "ORF" refers to a mRNA open reading frame, i.e., the region of the mRNA that can translated into protein.

Reference to the term "open reading frame" in the context of two or more open reading frames being in frame with each other refers to two nucleic acid sequences (e.g., nucleic acid residues of an exon(s) of SMN or a fragment thereof and/or a nucleotide sequence encoding an amino acid sequence), wherein each of the two or more nucleic acid sequences are in the same contiguous open reading frame which is defined by the first start codon and an aberrant stop codon, i.e., the stop codon upstream (5') of the reporter gene coding sequence.

Reference to the term "open reading frame" in the context of two or more open reading frames being out of frame with each other refers to two nucleic acid sequences (e.g., nucleic acid residues of an exon(s) of SMN or a fragment thereof and/or a reporter gene coding sequence), wherein each of the two or more nucleic acid sequences are not in the same contiguous open reading frame which is defined by the first start codon and an aberrant stop codon, i.e., the stop codon upstream (5') of the reporter gene coding sequence.

As used herein, the term "previously determined reference range" in the context of detecting the amount or activity of a protein refers to a reference range for the amount or the activity of a fusion protein encoded by a nucleic acid construct or transcribed from a mRNA transcript. Ideally, testing laboratories will establish a reference range for each cell type and each cell-free extract in the practice of such assays. In a specific embodiment, at least one positive control or at least one negative control is included for each compound analyzed. In a specific embodiment, the previously determined reference range is the amount or activity of a fusion protein detected in the presence of a negative control, such as phosphate-buffered saline ("PBS") or dimethyl sulfoxide ("DMSO").

As used herein, the terms "subject" and "patient" are used interchangeably, and refer to an animal (e.g., birds, reptiles, and mammals), such as a mammal including a non-primate (e.g., a camel, donkey, zebra, cow, pig, horse, goat, sheep, cat, dog, rat, and mouse) and a primate (e.g., a monkey, chimpanzee, and a human). In a specific embodiment, the subject is a human.

As used herein, the terms "treat," "treatment," and "treating" in the context of administration of a therapy(ies) to a subject, to treat SMA, refer to a therapeutic effect achieved following the administration of a compound or a combination of compounds. In a specific embodiment, the therapeutic effect is at least one or more of the following effects resulting from the administration of a compound or a combination of compounds: (i) the reduction or amelioration of the severity of SMA and/or a symptom associated therewith; (ii) the reduction in the duration of a symptom associated with SMA; (iii) the prevention in the recurrence of a symptom associated with SMA; (iv) the inhibition in the development or onset of a symptom of SMA; (v) the regression of SMA and/or a symptom associated therewith; (vi) the reduction in the loss of muscle strength; (vii) the increase in muscle strength; (viii) the reduction in muscle atrophy; (ix) the reduction in the loss of motor function; (x) the increase in motor neurons; (xi) the reduction in the loss of motor neurons; (xii) the protection of SMN deficient motor neurons from degeneration; (xiii) the increase in motor function; (xiv) the increase in pulmonary function; (xv) the reduction in the loss of pulmonary function; (xvi) the reduction in hospitalization of a subject; (xvii) the reduction in hospitalization length for a subject; (xviii) the increase in the survival of a subject; (xix) the inhibition of the progression of SMA and/or a symptom associated therewith; and/or (xx) the enhancement or improvement the therapeutic effect of another therapy. In some embodiments, the therapeutic effect reduces or inhibits the progression of SMA or a symptom thereof.

As used herein, the terms "antibodies that specifically bind to a stabilized SMNΔEx7 protein," "anti-SMNΔEx7 antibodies," and analogous terms refer to antibodies that specifically bind to an epitope that arises as a result of the additional C-terminal amino acids of SMNΔEx7 that result from a ribosomal frameshift during the translation of mRNA transcribed from the SMN2 gene. An antibody that specifically binds to a stabilized SMNΔEx7 protein can be identified, for example, by immunoassays, BIAcore®, or other techniques known to those of skill in the art. In a specific embodiment, an antibody binds specifically to a stabilized SMNΔEx7 protein when it binds to a stabilized SMNΔEx7 protein with a higher association rate ($K_a$) and/or a lower dissociation rate ($K_D$) than to the naturally-occurring SMNΔEx7 protein as determined using experimental techniques, such as radioimmunoassays (RIA) and enzyme-linked immunosorbent assays (ELISAs). See, e.g., Blake, et al., *Analytical Biochem.*, 1999, 272:123-134; and Paul, ed., 1989, *Fundamental Immunology Second Edition*, Raven Press, New York at pages 332-336 for a discussion regarding antibody specificity.

Antibodies include, but are not limited to, synthetic antibodies, monoclonal antibodies, recombinantly produced antibodies, multispecific antibodies (including bispecific antibodies), human antibodies, humanized antibodies, chimeric antibodies, intrabodies, single-chain Fvs (scFv) (e.g., including monospecific, bispecific, etc.), Fab fragments, F(ab') fragments, disulfide-linked Fvs (sdFv), anti-idiotypic (anti-Id) antibodies, and epitope-binding fragments of any of the above. In a specific embodiment, antibodies include immunoglobulin molecules and immunologically active portions of immunoglobulin molecules, i.e., molecules that contain an antigen-binding site that specifically binds to a stabilized SMNΔEx7 protein (e.g., one or more complementarity determining regions (CDRs) of an anti-SMNΔEx7 antibody). The antibodies can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule.

BRIEF DESCRIPTION OF THE DRAWINGS

FIG. 1: DNA sequence of the minigene from the SMN2-G minigene construct (SEQ ID NO:11). Within the sequence shown in FIG. 1, the following subsequences can be found:

1-70: 5'UTR (deg)

71-79: start codon and BamHI site (atgggatcc)

80-190: exon 6

191-5959: intron 6

5960-6014: exon 7 with G insert (position 6008)

6015-6458: intron 7

6459-6481: part of exon 8

6482-8146: BamHI site, luciferase coding sequence starting with codon 2, NotI site, TAA stop codon 8147-8266: 3'UTR (deg). (A) nucleic acids 1-4009 of the DNA sequence; (B) nucleic acids 4010-7885 of the DNA sequence; (C) nucleic acids 7886-8266 of the DNA sequence.

FIG. 2: Sequences of SMNΔEx7 protein and stabilized SMNΔEx7 proteins. Stabilizing C-terminal amino acids are underlined. (A) SMNΔEx7 (SEQ ID NO:1); (B) stabilized SMNΔEx7 produced by +2 frameshift (SEQ ID NO:2); (C) stabilized SMNΔEx7 produced by −1 frameshift (SEQ ID NO:3); (D) stabilized SMNΔEx7 produced by +1 frameshift (SEQ ID NO:4); (E) stabilized SMNΔEx7 produced by −2 frameshift (SEQ ID NO:5).

FIG. 3: Depiction of the nucleotide and amino acid sequences of constructs comprising naturally-occurring SMNΔEx7 (top panel; nucleotide sequence presented is SEQ ID NO:30; amino acid sequence presented as GYYMEMLA is SEQ ID NO:28; amino acid sequence presented as SSTK is SEQ ID NO:27) and SMNΔEx7-LSSTK (SEQ ID NO:26) comprising a stop codon to leucine codon mutation (TAG to TTG) (bottom panel; nucleotide sequence presented is SEQ ID NO:31; amino acid sequence presented is SEQ ID NO:29). Replacement of the stop codon with a leucine codon results in the addition of four additional amino acids following the leucine codon (serine, serine, threonine, lysine; SSTK; SEQ ID NO:27).

FIG. 4: Western blot analysis of naturally-occurring SMNΔEx7 and SMNΔEx7 comprising a mutated a stop codon and additional C-terminal amino acids ("SMNΔEx7-LSSTK"; SEQ ID NO:26).

DETAILED DESCRIPTION

Described herein are nucleic acid constructs and screening assays for the identification and validation of compounds that cause ribosomal frameshifting, and thus, are capable of producing a stabilized SMNΔEx7 protein. Compounds identified or validated according to the methods described herein are expected to be useful in the treatment of SMA.

In one aspect, presented herein is a method for identifying or validating a compound that produces a stabilized SMNΔEx7 protein. In another aspect, presented herein are compounds that produce a stabilized SMNΔEx7 protein, which may be used to treat SMA. In one embodiment, a compound of Formula (I) or a form thereof is used to treat SMA. In another embodiment, a compound of Formula (II) or a form thereof is used to treat SMA. In another embodiment, a compound of Formula (Ia) or a form thereof is used to treat SMA. In another embodiment, a compound of Formula (IIa) or a form thereof is used to treat SMA. In a specific embodiment, Compound I is used to treat SMA.

Compounds

The compounds described on pages 27-244 (Table 1), 254 (Table 2), and 257 (Table 3) of International Publication WO2007/109211 (which is incorporated by reference in its entirety) may be used in accordance with the methods described herein.

Embodiments disclosed herein include uses of compounds of Formula (I) or a form thereof or Formula (II) or a form thereof, wherein Formula (I) and Formula (II) have the following structures:

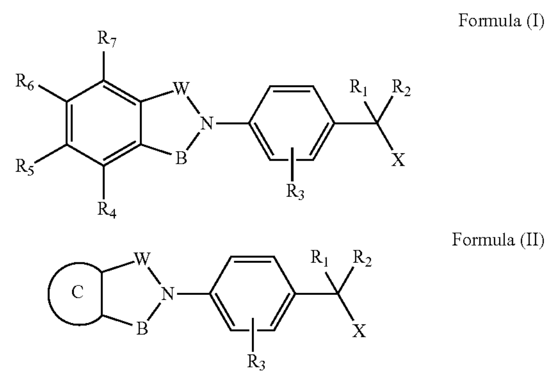

wherein,

W is selected from the group consisting of C(O), C(S), and $CH_2$;

B is $CH_2$ or $CH(C_nH_{2n+1})$, wherein n is an integer from 1 to 8;

Ring C is selected from the group consisting of a fused thienyl ring, a fused pyridinyl ring, and a fused cyclohexyl ring, any of which can be saturated or contain, one or two non-conjugated double bonds;

$R_1$ and $R_2$ are independently selected from the group consisting of H and $C_1$-$C_3$ alkyl, or $R_1$ and $R_2$ may be taken together with the carbon atom to which they are attached to form a $C_3$-$C_6$ cycloalkyl ring or a carbonyl group;

$R_3$ is selected from the group consisting of H, halogen, $C_1$-$C_4$ alkyl, $C_1$-$C_4$ alkoxy, $C_1$-$C_4$ haloalkyl, CN, $NO_2$, heteroaryl, and phenyl optionally substituted with any combination of one to five halogen, $NO_2$, CN, $C_1$-$C_4$ alkyl, $C_1$-$C_4$ haloalkyl, or $C_1$-$C_4$ alkoxy substituents;

$R_4$, $R_5$, $R_6$ and $R_7$ are independently selected from the group consisting of H, hydroxyl, halogen, CN, $NO_2$, sulfonamide, $C_1$-$C_8$ alkyl, $C_3$-$C_6$ cycloalkyl, cycloalkyloxy, $C_1$-$C_6$ alkoxy, $C_1$-$C_6$ haloalkoxy, $C_1$-$C_4$ haloalkyl, $C_2$-$C_8$ alkenyl, amino, $C_1$-$C_4$ alkylamino, $C_1$-$C_4$ dialkylamino, $C_3$-$C_6$ cycloalkylamino, morpholinyl, heteroaryl, arylamino, arylalkylamino, phenyl, C(O)R', NR'(COR"), NR'$SO_2$R" and NR'(CONR"R'"), wherein R', R" and R'" are independently H, $C_1$-$C_6$ alkyl, phenyl, or substituted phenyl, and wherein $C_1$-$C_8$ alkyl is optionally substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, and morpholinyl, and the phenyl is optionally substituted with one or more substituents selected from the group consisting of halogen, $NO_2$, CN, $C_1$-$C_4$ alkyl, $C_1$-$C_4$ haloalkyl, and $C_1$-$C_4$ alkoxy, or $R_4$ and $R_5$, $R_5$ and $R_6$, or $R_6$ and $R_7$, taken together with the carbon to which they are attached, form a ring;

X is selected from the group consisting of H; CN; C(O)$OR_8$, wherein $R_8$ is H or $C_1$-$C_8$ alkyl, and $C_1$-$C_8$ alkyl optionally is substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, phenyl, and morpholinyl; C(O)$NR_9R_{10}$ or $CH_2NR_9R_{10}$, wherein $R_9$ and $R_{10}$ are independently selected from the group consisting of H and $C_1$-$C_6$ alkyl, or $R_9$ and $R_{10}$ together with the nitrogen to which they are attached form a heterocyclyl ring; $CH_2OR_{11}$, wherein $R_{11}$ is H, $C_1$-$C_8$ alkyl, or $C_3$-$C_6$ cycloalkyl, wherein $C_1$-$C_8$ alkyl is optionally substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, and morpholinyl; $CH_2Z$, wherein Z is halogen; C(O)NHOH; C(O)NHCN; C(O)N($R_1$)$SO_2R_{13}$, wherein $R_{13}$ is $C_1$-$C_4$ alkyl, phenyl, or substituted phenyl; $C_1$-$C_8$ alkyl, optionally substituted with one or more substituents selected from the group consisting of $C_1$-$C_4$ alkoxy, $C_1$-$C_4$ haloalkyl, $C_1$-$C_6$ dialkylamino, and $C_1$-$C_6$ alkylamino; and $C_2$-$C_8$ alkenyl, optionally substituted with one or more substituents selected from the group consisting of $C_1$-$C_4$ alkoxy, $C_1$-$C_4$ haloalkyl, $C_1$-$C_6$ dialkylamino, and $C_1$-$C_6$ alkylamino.

In certain embodiments, compounds of Formula (Ia) or a form thereof or Formula (IIa) or a form thereof, wherein Formula (Ia) and Formula (IIa) have the following structures are used:

Formula (Ia)

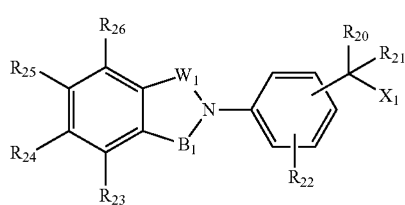

-continued

Formula (IIa)

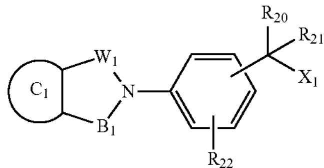

wherein, $W_1$ is selected from the group consisting of C(O), C(S), and $CH_2$;

$B_1$ is $CH_2$ or $CH(C_mH_{2m+1})$, wherein m is an integer from 1 to 8;

Ring $C_1$ is selected from the group consisting of a thienyl ring, a pyridinyl ring, a cyclohexyl ring, a benzo[d][1,3]dioxolyl ring and a 2,3-dihydrobenzo[b][1,4]dioxinyl ring, each of said rings fused to the moiety of Formula (IIa), wherein benzo[d][1,3]dioxolyl and 2,3-dihydrobenzo[b][1,4]dioxinyl, each having a benzo ring portion, are fused via said benzoportion, and wherein any of the foregoing rings may optionally be fully or partially saturated;

$R_{20}$ and $R_{21}$ are independently selected from the group consisting of H and $C_1$-$C_3$ alkyl, or $R_{20}$ and $R_{21}$ may be taken together with the carbon atom to which they are attached to form a $C_3$-$C_6$ cycloalkyl ring or a carbonyl group;

$R_{22}$ is selected from the group consisting of H, halogen, $C_1$-$C_4$ alkyl, $C_1$-$C_4$ alkoxy, $C_1$-$C_4$ haloalkyl, cyano, nitro, heteroaryl, and phenyl optionally substituted with any combination of one to five halogen, nitro, cyano, $C_1$-$C_4$ alkyl, $C_1$-$C_4$ haloalkyl or $C_1$-$C_4$ alkoxy substituents;

$R_{23}$, $R_{24}$, $R_{25}$ and $R_{26}$ are independently selected from the group consisting of H, hydroxyl, halogen, cyano, nitro, sulfonamide, $C_1$-$C_8$ alkyl, $C_1$-$C_6$ alkoxy, $C_1$-$C_6$ alkoxyalkoxy, $C_1$-$C_6$ alkoxyalkyl, $C_1$-$C_6$ haloalkoxy, $C_1$-$C_4$ haloalkyl, $C_2$-$C_6$ alkenyl, $C_2$-$C_4$ haloalkenyl, formyl, $C_1$-$C_6$ alkylcarbonyl, amino, $C_1$-$C_4$ alkylamino, $C_1$-$C_4$ dialkylamino, $C_1$-$C_4$ aminoalkyl, $C_1$-$C_4$ alkylaminoalkyl, $C_1$-$C_4$ dialkylaminoalkyl, phenyl, $C_3$-$C_6$ cycloalkyl, $C_3$-$C_6$ cycloalkylalkyl, $C_3$-$C_6$ cycloalkylalkoxy, cycloalkyloxy, heterocyclyl, heterocyclylalkyl, heteroaryl, and phenylcarbonyl, wherein amino is optionally disubstituted with one substituent selected from hydrogen, $C_1$-$C_6$ alkyl or phenyl and the other is selected from formyl, phenyl, $C_3$-$C_6$ cycloalkyl, $C_1$-$C_6$ alkylcarbonyl, aminocarbonyl, $C_1$-$C_6$ alkylaminocarbonyl, $C_1$-$C_6$ dialkylaminocarbonyl, phenylcarbonyl, phenylaminocarbonyl, N-phenyl-N—$C_1$-$C_6$ alkyl-aminocarbonyl, $C_1$-$C_6$ alkylsulfonyl, aminosulfonyl, $C_1$-$C_6$ alkylaminosulfonyl, $C_1$-$C_6$ dialkylaminosulfonyl or phenylsulfonyl, wherein each instance of $C_1$-$C_6$ alkylcarbonyl is optionally substituted on the alkyl portion with one or more substituents selected from the group consisting of halogen, $C_1$-$C_4$ alkoxy, $C_1$-$C_6$ alkylamino, $C_1$-$C_6$ dialkylamino, cycloalkylamino and heterocyclyl, wherein each instance of phenyl is optionally substituted with one or more substituents selected from the group consisting of halogen, nitro, cyano, $C_1$-$C_4$ alkyl, $C_1$-$C_4$ haloalkyl and $C_1$-$C_4$ alkoxy, and alternatively, $R_{23}$ and $R_{24}$, $R_{24}$ and $R_{25}$ or $R_{25}$ and $R_{26}$ may be taken together with the carbon to which they are attached to form a $C_3$-$C_6$ cycloalkyl ring fused to the moiety of Formula (Ia);

$X_1$ is absent or is selected from the group consisting of H, cyano, $C_1$-$C_8$ alkyl, $C_1$-$C_4$ alkoxy, amino, $C_1$-$C_4$ alkylamino, $C_1$-$C_4$ dialkylamino, carboxy, $C_1$-$C_8$ alkoxycarbonyl, aminocarbonyl, $C_1$-$C_8$ alkylaminocarbonyl, $C_1$-$C_8$ dialkylaminocarbonyl, hydroxylaminocarbonyl, cyanoaminocarbonyl, phenylaminocarbonyl, amino sulfonylaminocarbonyl, $C_1$-$C_8$ alkylaminosulfonylaminocarbonyl, $C_1$-$C_8$ dialkylaminosulfonylaminocarbonyl, $C_1$-$C_8$ alkylsulfonylaminocarbonyl, phenylsulfonylaminocarbonyl and heterocyclylcarbonyl, wherein $C_1$-$C_4$ alkoxy and the $C_1$-$C_8$ alkoxy portion of $C_1$-$C_8$ alkoxycarbonyl is optionally substituted with one or more substituents selected from the group consisting of halogen, $C_1$-$C_4$ alkoxy, $C_1$-$C_4$ haloalkyl, amino, $C_1$-$C_6$ alkylamino, $C_1$-$C_6$ dialkylamino, cycloalkylamino, phenyl and heterocyclyl, wherein $C_1$-$C_8$ alkyl is optionally substituted with one or more substituents selected from the group consisting of halogen, hydroxyl, $C_1$-$C_4$ haloalkyl, $C_2$-$C_8$ alkenyl, $C_1$-$C_6$ alkoxy, $C_1$-$C_4$ alkoxyalkoxy, $C_3$-$C_6$ cycloalkyloxy, amino, $C_1$-$C_6$ alkylamino, $C_1$-$C_6$ dialkylamino, cycloalkylamino, aminocarbonyl, $C_1$-$C_6$ alkylaminocarbonyl, $C_1$-$C_6$ dialkylaminocarbonyl, hydroxylaminocarbonyl, cyanoaminocarbonyl, $C_1$-$C_6$ alkylsulfonylaminocarbonyl, phenylsulfonylaminocarbonyl and heterocyclyl, wherein $C_1$-$C_4$ alkoxy or $C_2$-$C_8$ alkenyl are each further optionally substituted with one or more substituents selected from the group consisting of $C_1$-$C_4$ alkoxy, $C_1$-$C_4$ haloalkyl, amino, $C_1$-$C_6$ alkylamino and $C_1$-$C_6$ dialkylamino.

As used herein, unless otherwise specified, the term "alkyl" means a saturated straight chain or branched non-cyclic hydrocarbon chain radical having an indicated number of carbon atoms (e.g., $C_1$-$C_{20}$, $C_1$-$C_{10}$, $C_1$-$C_8$, $C_1$-$C_6$, $C_1$-$C_4$, $C_1$-$C_3$, etc.). Representative saturated straight chain alkyl radicals include methyl, ethyl, n-propyl, n-butyl, n-pentyl, n-hexyl, n-heptyl, n-octyl, n-nonyl and n-decyl; while representative saturated branched chain alkyl radicals include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. An alkyl radical can be unsubstituted or substituted.

As used herein, unless otherwise specified, the term "cycloalkyl" means a monocyclic or polycyclic saturated ring comprising carbon and hydrogen atoms and having no carbon-carbon multiple bonds. Examples of cycloalkyl radicals include, but are not limited to cyclopropyl, cyclobutyl, cyclopentyl, cyclohexyl, and cycloheptyl, and saturated cyclic and bicyclic terpenes. A cycloalkyl radical can include $C_3$-$C_{14}$ cycloalkyl, $C_5$-$C_8$ cycloalkyl, $C_3$-$C_8$ cycloalkyl, $C_3$-$C_6$ cycloalkyl, $C_3$-$C_6$ cycloalkyl, $C_3$-$C_5$ cycloalkyl, and the like, each of which may be unsubstituted or substituted. Preferably, the cycloalkyl radical is a monocyclic ring or bicyclic ring.

As used herein, unless otherwise specified, the term "alkenyl" means a straight chain or branched non-cyclic hydrocarbon chain radical having an indicated number of carbon atoms (e.g., $C_2$-$C_{20}$, $C_2$-$C_{10}$, $C_2$-$C_8$, $C_2$-$C_6$, $C_2$-$C_4$, etc.) and including at least one carbon-carbon double bond. Representative straight chain and branched chain alkenyl radicals include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. The double bond of an alkenyl radical can be unconjugated or conjugated to another unsaturated radical. An alkenyl radical can be unsubstituted or substituted.

As used herein, unless otherwise specified the term "alkynyl" means a straight chain or branched non-cyclic hydrocarbon chain radical having an indicated number of carbon atoms (e.g., $C_2$-$C_{20}$, $C_2$-$C_{10}$, $C_2$-$C_8$, $C_2$-$C_6$, $C_2$-$C_4$, etc.), and including at least one carbon-carbon triple bond. Representative straight chain and branched chain alkynyl radicals include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl and the like. The triple bond of an alkynyl radical can be unconjugated or conjugated to another unsaturated group. An alkynyl radical can be unsubstituted or substituted.

As used herein, unless otherwise specified, the term "halogen" or "halo" means fluorine, chlorine, bromine, or iodine. Furthermore, unless otherwise specified, the term "haloalkyl" means alkyl substituted with one or more halogens, wherein alkyl and halogen are defined as above.

As used herein, unless otherwise specified, the term "alkoxy" means —O-(alkyl), wherein alkyl is defined above.

Furthermore, as used herein, the term "haloalkoxy" means alkoxy substituted with one or more halogens, wherein alkoxy and halogen are defined as above.

As used herein, unless otherwise specified, the term "heteroaryl" means an carbocyclic aromatic ring containing from 5 to 14 ring atoms comprising at least one heteroatom, preferably 1 to 3 heteroatoms, independently selected from a nitrogen, oxygen, and sulfur atom. Heteroaryl ring structures include compounds having one or more ring structures, such as mono-, bi-, or tricyclic compounds, as well as fused heterocyclic moities. Representative heteroaryls are triazolyl, tetrazolyl, thiadiazolyl, oxadiazolyl, pyridyl, furanyl, benzofuranyl, thiophenyl (also referred to as thienyl), thiazolyl, benzothiophenyl, benzoisoxazolyl, benzoisothiazolyl, quinolinyl, isoquinolinyl, pyrrolyl, indolyl, indazolyl, isoindolyl, azaindolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, benzoquinazolinyl, acridinyl and the like. A heteroaryl ring can be substituted or unsubstituted on a carbon or nitrogen atom, wherein substitution on a nitrogen atom may optionally form a quaternary salt moiety.

As used herein, unless otherwise specified, the term "heterocyclyl" means a saturated or partially saturated monocyclic, bicyclic or polycyclic carbocyclic ring containing from 5 to 14 ring atoms comprising at least one heteroatom, preferably 1 to 3 heteroatoms, independently selected from a nitrogen, oxygen, and sulfur atom. Representative heterocyclyls are oxiranyl, oxetanyl, azetidinyl, dihydrofuranyl, tetrahydrofuranyl, dihydrothienyl, tetrahydrothienyl, pyrrolinyl, pyrrolidinyl, dihydropyrazolyl, pyrazolinyl, pyrazolidinyl, dihydroimidazolyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, dihydro-2H-pyranyl, tetrahydro-2H-pyranyl, tetrahydro-thiopyranyl, dihydro-pyridinyl, tetrahydro-pyridinyl, hexahydro-pyridinyl, dihydro-pyrimidinyl, tetrahydro-pyrimidinyl, dihydropyrazinyl, tetrahydro-pyrazinyl, dihydro-pyridazinyl, tetrahydro-pyridazinyl, piperazinyl, piperidinyl, morpholinyl, thiomorpholinyl, dihydro-triazinyl, tetrahydro-triazinyl, hexahydro-triazinyl, dihydro-indole, tetrahydro-indole, dihydro-indazolyl, tetrahydro-indazolyl, dihydro-isoindolyl, tetrahydro-isoindolyl, dihydro-benzofuranyl, tetrahydro-benzofuranyl, dihydro-benzothienyl, tetrahydro-benzothienyl, dihydro-benzimidazolyl, tetrahydro-benzimidazolyl, dihydro-benzoxazolyl, tetrahydro-benzoxazolyl, benzo[1,3]dioxolyl, benzo[1,4]dioxanyl, dihydro-purinyl, tetrahydro-purinyl, dihydro-quinolinyl, tetrahydro-quinolinyl, dihydro-isoquinolinyl, tetrahydro-isoquinolinyl, dihydro-quinazolinyl, tetrahydro-quinazolinyl, dihydro-quinoxalinyl, tetrahydro-quinoxalinyl and the like. A heterocyclyl radical can be unsubstituted or substituted on a carbon or nitrogen atom, wherein substitution on a nitrogen atom may form a quaternary salt moiety.

As used herein, unless otherwise specified, the term "CH($C_nH_{2n+1}$)," wherein n is an integer from 1 to 8, refers to an alkyl chain radical of the formula: —$(CH_2)_{1-7}$—$CH_3$ substituted on the B variable of either Formula (I) or Formula (II), wherein B is —CH—.

As used herein, unless otherwise specified, the term "CH($C_mH_{2m+1}$)," wherein m is an integer from 1 to 8, refers to an alkyl chain radical of the formula: —$(CH_2)_{1-7}$—$CH_3$ substituted on the $B_1$ variable of either Formula (Ia) or Formula (IIa), wherein $B_1$ is —CH—.

As used herein, unless otherwise specified, the term "alkanoyl" refers to a radical of the formula: —C(O)-alkyl, wherein alkyl is defined above.

As used herein, unless otherwise specified, the term "alkanoylamino" refers to a radical of the formula: —NH—C(O)-alkyl, wherein alkyl is defined above.

As used herein, unless otherwise specified, the term "alkanoyloxy" refers to a radical of the formula: —O—C(O)-alkyl, wherein alkyl is defined above.

As used herein, the term "alkoxyalkoxy" refers to a radical of the formula: —O-alkyl-O-alkyl, wherein alkyl is defined above (e.g., $C_1$-$C_6$ alkoxyalkoxy and the like).

As used herein, the term "alkoxyalkyl" refers to a radical of the formula: -alkyl-O-alkyl, wherein alkyl is defined above (e.g., $C_1$-$C_6$ alkoxyalkyl and the like).

As used herein, the term "alkoxycarbonyl" refers to a radical of the formula: —C(O)—O-alkyl, wherein alkyl is defined above.

As used herein, unless otherwise specified, the term "alkylamino" refers to a radical of the formula: —NH-alkyl, wherein alkyl is defined above.

As used herein, unless otherwise specified, the term "alkylaminoalkyl" refers to a radical of the formula: -alkyl-NH-alkyl, wherein alkyl is defined above.

As used herein, unless otherwise specified, the term "alkylaminocarbonyl" refers to a radical of the formula: —C(O)—NH-alkyl, wherein alkyl is defined above.

As used herein, unless otherwise specified, the term "alkylaminosulfonyl" refers to a radical of the formula: —$SO_2$—NH-alkyl, wherein alkyl is defined above.

As used herein, unless otherwise specified, the term "alkylaminosulfonylaminocarbonyl" refers to a radical of the formula: —C(O)—NH—$SO_2$—NH-alkyl, wherein alkyl is defined above.

As used herein, the term "alkylcarbonyl" refers to a radical of the formula: —C(O)-alkyl, wherein alkyl is defined above.

As used herein, unless otherwise specified, the term "alkylsulfonyl" refers to a radical of the formula: —$SO_2$-alkyl, wherein alkyl is defined above.

As used herein, unless otherwise specified, the term "alkylsulfonylaminocarbonyl" refers to a radical of the formula: —C(O)—NH—$SO_2$-alkyl, wherein alkyl is defined above.

As used herein, unless otherwise specified, the terms "alkylthio" and "alkylthioether" refer to a radical of the formula: —S-alkyl, wherein alkyl is defined above.

As used herein, unless otherwise specified, the term "alkylthiono" refers to a radical of the formula: —C(S)-alkyl, wherein alkyl is defined above.

As used herein, unless otherwise specified, the term "amino" refers to a radical of the formula: —$NH_2$.

As used herein, unless otherwise specified, the term "aminoalkyl" refers to a radical of the formula: -alkyl-$NH_2$, wherein alkyl is defined above.

As used herein, unless otherwise specified, the term "aminocarbonyl" refers to a radical of the formula: —C(O)—$NH_2$, wherein alkyl is defined above.

As used herein, unless otherwise specified, the terms "aminosulfonyl", "sulfonamide" and "sulfonamido" refer to a radical of the formula: —$SO_2$—$NH_2$.

As used herein, unless otherwise specified, the term "aminosulfonylaminocarbonyl" refers to a radical of the formula: —C(O)—NH—$SO_2$—$NH_2$.

As used herein, unless otherwise specified, the term "aralkanoylamino" refers to a radical of the formula: —NH—C(O)-alkyl-aryl, wherein alkyl and aryl are defined above.

As used herein, unless otherwise specified, the terms "aroyl" and "arylcarbonyl" refer to a radical of the formula: —C(O)-aryl, wherein aryl is defined above (e.g., phenylcarbonyl and the like).

As used herein, unless otherwise specified, the term "aroylamino" refers to a radical of the formula: —NH—C(O)-aryl, wherein aryl is defined above.

As used herein, unless otherwise specified, the term "arylalkoxycarbonyl" refers to a radical of the formula: —C(O)—O-alkyl-aryl, wherein alkyl and aryl are defined above (e.g., benzyloxycarbonyl, and the like).

As used herein, unless otherwise specified, the term "arylalkyl" refers to a radical of the formula: -alkyl-aryl, wherein alkyl and aryl are defined above.

As used herein, unless otherwise specified, the term "arylalkylamino" refers to a radical of the formula: —NH-alkyl-aryl, wherein alkyl and aryl are defined above.

As used herein, unless otherwise specified, the term "N-aryl-N-alkyl-aminocarbonyl" refers to a radical, wherein amino is disubstituted, of the formula: —C(O)—N(aryl-alkyl), wherein alkyl and aryl are defined above (e.g., N-phenyl-N-alkyl-aminocarbonyl and the like).

As used herein, unless otherwise specified, the term "arylalkylsulfonyl" refers to a radical of the formula: —$SO_2$-alkyl-aryl, wherein alkyl and aryl are defined above.

As used herein, unless otherwise specified, the term "arylalkylthio" refers to a radical of the formula: —S-alkyl-aryl, wherein alkyl and aryl are defined above.

As used herein, unless otherwise specified, the term "arylalkylthiono" refers to a radical of the formula: —C(S)-alkyl-aryl, wherein alkyl and aryl are defined above.

As used herein, unless otherwise specified, the term "arylamino" refers to a radical of the formula: —NH-aryl, wherein aryl is defined above.

As used herein, unless otherwise specified, the term "arylaminocarbonyl" refers to a radical of the formula: —C(O)—NH-aryl, wherein aryl is defined above (e.g., phenylaminocarbonyl and the like).

As used herein, unless otherwise specified, the term "aryloxy" refers to a radical of the formula: —O-aryl, wherein aryl is defined above.

As used herein, unless otherwise specified, the term "arylsulfonyl" refers to a radical of the formula: —$SO_2$-aryl, wherein aryl is defined above (e.g., phenylsulfonyl and the like).

As used herein, unless otherwise specified, the term "arylsulfonylaminocarbonyl" refers to a radical of the formula: —C(O)—NH—$SO_2$-aryl, wherein aryl is defined above (e.g., phenylsulfonylaminocarbonyl, and the like).

As used herein, unless otherwise specified, the term "arylthio" refers to a radical of the formula: —S-aryl, wherein aryl is defined above.

As used herein, unless otherwise specified, the term "arylthiono" refers to a radical of the formula: —C(S)-aryl, wherein aryl is defined above.

As used herein, the term "carbamyl" refers to a radical of the formula: —C(O)—$NH_2$.

As used herein, the term "carbonyl" refers to a radical of the formula: —C(O)—.

As used herein, the term "carboxy" refers to a radical of the formula: —COOH or —$CO_2H$.

As used herein, unless otherwise specified, the term "cyanoaminocarbonyl" refers to a radical of the formula: —C(O)—NH—C≡N or —C(O)—NH—CN.

As used herein, unless otherwise specified, the term "cycloalkylalkoxy" refers to a radical of the formula: —O-alkyl-cycloalkyl, wherein cycloalkyl is defined above (e.g., cyclopentyl-alkoxy, cyclobutyl-alkoxy and the like).

As used herein, unless otherwise specified, the term "cycloalkylalkyl" refers to a radical of the formula: -alkyl-cycloalkyl, wherein cycloalkyl is defined above (e.g., $C_3$-$C_6$ cycloalkylalkyl and the like).

As used herein, unless otherwise specified, the term "cycloalkylamino" refers to a radical of the formula: —NH-cycloalkyl, wherein cycloalkyl is defined above.

As used herein, unless otherwise specified, the term "cycloalkyloxy" refers to a radical of the formula: —O-cycloalkyl, wherein cycloalkyl is defined above (e.g., $C_3$-$C_6$ cycloalkyloxy and the like).

As used herein, unless otherwise specified, the term "cycloalkylthio" refers to a radical of the formula: —S-cycloalkyl, wherein cycloalkyl is defined above.

As used herein, unless otherwise specified, the term "dialkylamino" refers to a radical of the formula: —$N(alkyl)_2$, wherein alkyl is defined above.

As used herein, unless otherwise specified, the term "dialkylaminoalkyl" refers to a radical of the formula: -alkyl-$N(alkyl)_2$, wherein alkyl is defined above.

As used herein, unless otherwise specified, the term "dialkylaminocarbonyl" refers to a radical of the formula: —C(O)—$N(alkyl)_2$, wherein alkyl is defined above (e.g., $C_1$-$C_6$ dialkylaminocarbonyl and the like).

As used herein, unless otherwise specified, the term "dialkylaminosulfonyl" refers to a radical of the formula: —$SO_2$—$N(alkyl)_2$, wherein alkyl is defined above (e.g., $C_1$-$C_6$ dialkylaminosulfonyl and the like).

As used herein, unless otherwise specified, the term "dialkylaminosulfonylaminocarbonyl" refers to a radical of the formula: —C(O)—NH—$SO_2$—$N(alkyl)_2$, wherein alkyl is defined above.

As used herein, the term "formyl" refers to a radical of the formula: —C(O)H.

As used herein, the term "guanidino" refers to a radical of the formula: —NH—C(NH)—$NH_2$.

As used herein, the term "halo" or "halogen" generally refers to a halogen atom radical, such as fluoro, chloro, bromo and iodo.

As used herein, the term "haloalkenyl" refers to a radical of the formula: -alkenyl-halo, wherein alkenyl and halo are defined above and may be partially or completely substituted where allowed by available valences with one or more halogen atoms (e.g., trifluoroalkenyl, and the like).

As used herein, the term "haloalkoxy" refers to a radical of the formula: —O-alkyl-halo, wherein alkyl and halo are defined above and may be partially or completely substituted where allowed by available valences with one or more halogen atoms (e.g., trifluoroalkoxy, difluoroalkoxy, and the like).

As used herein, the term "haloalkyl" refers to a radical of the formula: -alkyl-halo, wherein alkyl and halo are defined above and may be partially or completely substituted where allowed by available valences with one or more halogen atoms (e.g., trifluoroalkyl and the like).

As used herein, unless otherwise specified, the term "heteroarylalkyl" refers to a radical of the formula: -alkyl-heteroaryl, wherein alkyl and heteroaryl are defined above.

As used herein, unless otherwise specified, the terms "heterocyclylalkyl" and "alkylheterocyclyl" refer to a radical of the formula: -alkyl-heterocyclyl, wherein alkyl and heterocyclyl are defined above (e.g., $C_1$-$C_4$ morpholinylalkyl and the like)).

As used herein, unless otherwise specified, the term "heterocyclylamino" refers to a radical of the formula: —NH-heterocyclyl, wherein heterocyclyl is defined above.

As used herein, unless otherwise specified, the term "heterocyclylcarbonyl" refers to a radical of the formula: —C(O)-heterocyclyl, wherein alkyl and aryl are defined above (e.g., morpholinylcarbonyl, piperidinylcarbonyl, and the like).

As used herein, unless otherwise specified, the term "heterocyclyloxy" refers to a radical of the formula: —O-heterocyclyl, wherein heterocyclyl is defined above.

As used herein, unless otherwise specified, the term "heterocyclylthio" refers to a radical of the formula: —S-heterocyclyl, wherein heterocyclyl is defined above.

As used herein, the term "hydroxylalkyl" refers to a radical of the formula: -alkyl-OH, wherein alkyl is defined above and may be partially or completely substituted where allowed by available valences with one or more hydroxyl substituents.

As used herein, unless otherwise specified, the term "hydroxylaminocarbonyl" refers to a radical of the formula: —C(O)—NH—OH.

As used herein, the term "thiol" refers to a radical of the formula: —SH.

As described herein, where one or more functionalities encompassing substituent variables for a compound of Formula (I) are incorporated into a compound of Formula (I), each functionality appearing at any location within the disclosed compound may be independently selected, and as appropriate, independently and/or optionally substituted.

As used herein, the term "substituent" means positional variables on the atoms of a core molecule that are known to those skilled in the art to be chemical moieties that are appropriate for substitution at a designated atom position, replacing one or more hydrogens on the designated atom with a selection from the indicated group, provided that the designated atom's normal valency under the existing circumstances is not exceeded, and that the substitution results in a stable compound. Combinations of substituents and/or variables are permissible only if such combinations result in stable compounds. It should also be noted that any carbon as well as heteroatom with unsatisfied valences as described or shown herein is assumed to have a sufficient number of hydrogen atom(s) to satisfy the valences described or shown.

As used herein, the terms "independently substituted," or "each selected from", and variations thereof, mean that, when any substituent occurs more than once in a substituent list or as a portion of a substituent in the list for Formula (I) or another structural formulae described herein, the pattern of substitution on any particular substituent at each occurrence is independent of the pattern at any other occurrence. Further, the use of a generic substituent variable on any formula or structure position for a compound described herein is understood to include the replacement of the generic substituent with species substituents that are included within the particular genus, e.g., aryl may be replaced with phenyl or naphthalenyl and the like, and that the resulting compound is to be included within the scope of the compounds described herein.

As used herein, the term "optionally substituted" means optional substitution with the specified groups, radicals or moieties.

As used herein, unless otherwise specified, the term "substituted" means a group substituted by one to four or more substituents, such as, alkyl, alkenyl, alkynyl, cycloalkyl, aroyl, halo, haloalkyl (e.g., trifluoromethyl), haloalkoxy (e.g., trifluoromethoxy), hydroxyl, alkoxy, alkylthioether, cycloalkyloxy, heterocyclyloxy, oxo, alkanoyl, aryl, arylalkyl, heteroaryl, heteroarylalkyl, heterocyclyl, aryloxy, alkanoyloxy, amino, arylamino, arylalkylamino, cycloalkylamino, heterocyclylamino, mono- and di-substituted amino (in which the one or two substituents on the amino group are selected from alkyl, aryl or arylalkyl), alkanoylamino, aroylamino, aralkanoylamino, substituted alkanoylamino, substituted arylamino, substituted aralkanoylamino, thiol, alkylthio, arylthio, arylalkylthio, cycloalkylthio, heterocyclylthio, alkylthiono, arylthiono, arylalkylthiono, alkylsulfonyl, arylsulfonyl, arylalkylsulfonyl, sulfonamido (e.g., $SO_2NH_2$), substituted sulfonamido, nitro, cyano, carboxy, carbamyl (e.g., $CONH_2$), substituted carbamyl (e.g., CONH-alkyl, CONH-aryl, CONH-arylalkyl or instances where there are two substituents on nitrogen selected from alkyl or arylalkyl), alkoxycarbonyl, aryl, substituted aryl, guanidino, substituted or unsubstituted heterocyclylalkyl, substituted or unsubstituted heteroaryl.

Whenever a range of the number of atoms in a structure is indicated (e.g., a $C_1$-$C_8$, $C_1$-$C_6$, $C_1$-$C_4$, or $C_1$-$C_3$ alkyl, $C_1$-$C_4$ haloalkyl or $C_1$-$C_4$ alkylamino, $C_2$-$C_8$ alkenyl, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), 2-8 carbon atoms (e.g., $C_2$-$C_8$) as used with respect to any chemical group (e.g., alkyl, haloalkyl, alkylamino, alkenyl, etc.) referenced herein encompasses and specifically describes 1, 2, 3, 4, 5, 6, 7, or 8 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 2-3 carbon atoms, 2-4 carbon atoms, 2-5 carbon atoms, 2-6 carbon atoms, 2-7 carbon atoms, 2-8 carbon atoms, 3-4 carbon atoms, 3-5 carbon atoms, 3-6 carbon atoms, 3-7 carbon atoms, 3-8 carbon atoms, 4-5 carbon atoms, 4-6 carbon atoms, 4-7 carbon atoms, 4-8 carbon atoms, 5-6 carbon atoms, 5-7 carbon atoms, 5-8 carbon atoms, 6-7 carbon atoms, or 6-8 carbon atoms, as appropriate).

Compound names used herein were obtained using the Autonom batch naming feature of ChemDraw Ultra Version 10.0.4, provided by CambridgeSoft. When the compound name disclosed herein conflicts with the structure depicted, the structure shown will supersede the use of the name to define the compound intended.

Encompassed herein are uses of all compounds described by Formulas (I) and (II) without limitation. However, for the purposes of further illustration, preferred aspects and elements are discussed herein.

With respect to Formulas (I) and (II), W is selected from the group consisting of C(O), C(S), and $CH_2$. According to certain aspects, W is C(O), especially with respect to compounds of Formula (I) and B is $CH_2$ or $CH(C_nH_{2n+1})$, wherein n is an integer from 1 to 8.

$R_1$ and $R_2$ can be the same or different, and are selected from the group consisting of H and $C_1$-$C_3$ alkyl, or $R_1$ and $R_2$ may be taken together with the carbon atom to which they are attached to form a $C_3$-$C_5$ or $C_3$-$C_6$ cycloalkyl ring or a carbonyl group. Preferably, $R_1$ and $R_2$ are H or $C_1$-$C_3$ alkyl. More preferably, $R_1$ is H and $R_2$ is $C_1$-$C_3$ alkyl.

$R_3$ is selected from the group consisting of H, halogen, $C_1$-$C_4$ alkyl, $C_1$-$C_4$ alkoxy, $C_1$-$C_4$ haloalkyl, CN, $NO_2$, heteroaryl, and phenyl optionally substituted with any combination of one to five halogen, $NO_2$, CN, $C_1$-$C_4$ alkyl, $C_1$-$C_4$ haloalkyl, or $C_1$-$C_4$ alkoxy substituents. However, $R_3$ preferably is H.

According to one aspect, at least one of $R_4$, $R_5$, $R_6$ and $R_7$ is not H. Thus, according to this aspect, at least one of $R_4$, $R_5$, $R_6$ and $R_7$, and in one embodiment $R_5$, $R_6$, and/or $R_7$, is selected from the group consisting of hydroxyl, halogen, CN, $NO_2$, sulfonamide, $C_1$-$C_8$ alkyl, $C_3$-$C_6$ cycloalkyl, cycloalkyloxy, $C_1$-$C_6$ alkoxy, $C_1$-$C_6$ haloalkoxy, $C_1$-$C_4$ haloalkyl, $C_2$-$C_8$ alkenyl, amino, $C_1$-$C_4$ dialkylamino, $C_1$-$C_4$ alkylamino, morpholinyl, heteroaryl, arylamino, arylalkylamino, phenyl, and C(O)R', NR'(COR"), NR'$SO_2$R" and NR'(CONR"R'"), wherein R', R" and R'" are independently H, $C_1$-$C_6$ alkyl, phenyl or substituted phenyl, and wherein $C_1$-$C_8$ alkyl is optionally substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, and morpholinyl, and the phenyl is optionally substituted with one or more substituents selected from the group consisting of halogen, $NO_2$, CN, $C_1$-$C_4$ alkyl, $C_1$-$C_4$ haloalkyl, and $C_1$-$C_4$ alkoxy, or any sub-group or sub-combination thereof.

In a further embodiment, either $R_5$ or $R_6$, or both, are not H. Thus, either $R_5$ or $R_6$, or both, are independently selected as above or from the group consisting of halogen, $C_1$-$C_8$ alkyl, $C_3$-$C_6$ cycloalkyl, cycloalkyloxy, $C_1$-$C_6$ alkoxy, $C_1$-$C_4$ haloalkyl, amino, $C_1$-$C_4$ dialkylamino, $C_1$-$C_4$ alkylamino, and morpholinyl, wherein $C_1$-$C_8$ alkyl is optionally substituted with one or more substituents selected from the group consisting of $C_1$-$C_4$ alkoxy, $C_1$-$C_4$ haloalkyl, $C_1$-$C_4$ dialkylamino, $C_1$-$C_6$ alkylamino, cycloalkylamino, and morpholinyl.

In one embodiment, $R_5$ is H and $R_6$ is selected as described above, or $R_6$ is selected from the group consisting of halogen, $C_1$-$C_3$ alkyl, $C_1$-$C_6$ alkoxy, cycloalkyloxy, $C_1$-$C_4$ dialkylamino, and $C_1$-$C_4$ haloalkyl. More specific examples of suitable $R_6$ groups include chloro, bromo, methyl, ethyl, propyl, i-propyl, methoxy, ethoxy, propoxy, i-propoxy, cyclohexyloxy, dimethylamino, and $CF_3$. When $R_6$ is not H, it is suitable that each of $R_4$, $R_5$, and $R_7$ are H.

When $R_5$ is not H, $R_5$ advantageously can be selected as described above, or from the group consisting of CN, halogen, $C_1$-$C_6$ alkyl, $C_3$-$C_6$ cycloalkyl, $C_1$-$C_6$ alkoxy, $C_1$-$C_4$ haloalkyl, amino, $C_1$-$C_4$ dialkyl amino, $C_1$-$C_4$ alkylamino and morpholinyl, wherein the $C_1$-$C_8$ alkyl is optionally substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, and morpholinyl. Specific examples of suitable $R_5$ groups include methyl, ethyl, propyl, or CN. When $R_5$ is not H, it is suitable that each of $R_4$, $R_6$, and $R_7$ are H.

When $R_7$ is not H, $R_7$ can be selected as described above, or from the group consisting of halogen, $C_1$-$C_8$ alkyl, $C_3$-$C_6$ cycloalkyl, $C_1$-$C_6$ alkoxy, $C_1$-$C_4$ haloalkyl, amino, $C_1$-$C_4$ dialkylamino, $C_1$-$C_4$ alkylamino, $C_3$-$C_6$ cycloalkylamino, and morpholinyl, wherein the $C_1$-$C_8$ alkyl is optionally substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, and morpholinyl. More specific examples of $R_7$ include $C_1$-$C_8$ alkyl, amino, or $C_1$-$C_4$ alkylamino, such as methyl, ethyl, propyl, or amino. When $R_7$ is not H, it is suitable that $R_4$, $R_5$, and $R_6$ are H.

Alternatively, or in addition, $R_4$ and $R_5$, $R_5$ and $R_6$, or $R_6$ and $R_7$, may be taken together with the carbon atoms to which they are attached to form a ring, preferably a 5 or 6 membered heterocyclyl ring, fused to the benzo portion of the compound of Formula (I). Non-limiting examples of such fused heterocyclyl rings include a fused [1,4]dioxanyl or fused [1,3]dioxolanyl ring.

Additional compounds of Formula (I) are those in which wherein at least one of $R_3$, $R_4$, $R_5$, $R_6$, or $R_7$ is hydroxyl, $C_1$-$C_6$ haloalkoxy, $C_2$-$C_6$ alkenyl, or $C_1$-$C_8$ alkyl substituted with an arylamino or arylalkylamino. In a further embodiment, at least one of $R_3$, $R_4$, $R_5$, $R_6$, or $R_7$ is a $C_1$-$C_6$ haloalkoxy. Non-limiting examples of haloalkoxy groups include —$OCHF_2$.

Alternatively, or in addition, at least one of $R_3$, $R_4$, $R_5$, $R_6$, or $R_7$ is C(O)R', NR'(COR"), NR'$SO_2$R" and NR'(CONR"R"), wherein R', R" and R" are independently H, $C_1$-$C_6$ alkyl, phenyl or substituted phenyl. Non-limiting examples of such NR'(CONR"R"') groups include urea (e.g., $NH(CO)NH_2$).

X is selected from the group consisting of H, CN, C(O)$OR_8$, wherein $R_8$ is H or $C_1$-$C_8$ alkyl, and $C_1$-$C_8$ alkyl optionally is substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, phenyl, and morpholinyl; C(O)$NR_9R_{10}$, wherein $R_9$ and $R_{10}$ are independently selected from the group consisting of H and $C_1$-$C_6$ alkyl, or $R_9$ and $R_{10}$ together with the nitrogen to which they are attached form a heterocyclyl ring such as morpholinyl; $CH_2OR_{11}$, wherein $R_{11}$ is H, $C_1$-$C_8$ alkyl, or $C_3$-$C_6$ cycloalkyl, wherein $C_1$-$C_8$ alkyl optionally is substituted with one or substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, and morpholinyl; $CH_2NR_9R_{10}$, wherein $R_9$ and $R_{10}$ are as defined above; $CH_2Z$, wherein Z is halogen; C(O)NHOH; C(O)NHCN; C(O)N($R_1$)$SO_2R_{13}$, wherein $R_{13}$ is $C_1$-$C_4$ alkyl, phenyl, or substituted phenyl; $C_1$-$C_8$ alkyl, optionally substituted with one or more substituents selected from the group consisting of $C_1$-$C_4$ alkoxy, $C_1$-$C_4$ haloalkyl, $C_1$-$C_6$ dialkylamino, and $C_1$-$C_6$ alkylamino; and $C_2$-$C_8$ alkenyl, optionally substituted with one or more substituents selected from the group consisting of $C_1$-$C_4$ alkoxy, $C_1$-$C_4$ haloalkyl, $C_1$-$C_6$ dialkylamino, and $C_1$-$C_6$ alkylamino; provided that when the compound is a compound of Formula (I), and each of $R_4$, $R_5$, $R_6$ and $R_7$ are H, then X is not C(O)OH.

While X can be chosen as described above, X can also be selected from the group consisting of CN; C(O)$OR_8$, wherein $R_8$ is $C_1$-$C_8$ alkyl, optionally substituted with phenyl; C(O)$NR_9R_{10}$, wherein $R_9$ and $R_{10}$ are independently selected from the group consisting of H and $C_1$-$C_6$ alkyl, or $R_9$ and $R_{10}$ together with the nitrogen to which they are attached form a heterocyclyl ring such as morpholinyl; $CH_2OR_{11}$, wherein $R_{11}$ is H, $C_1$-$C_8$ alkyl, or $C_3$-$C_6$ cycloalkyl, wherein $C_1$-$C_8$ alkyl optionally is substituted with one or substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, and morpholinyl; $CH_2NR_9R_{10}$, wherein $R_9$ and $R_{10}$ are as defined above; and $CH_2Z$, wherein Z is halogen; C(O)NHOH; C(O)NHCN; C(O)N($R_1$)$SO_2R_{13}$, wherein in $R_{13}$ is $C_1$-$C_4$ alkyl, phenyl, or substituted phenyl.

In another embodiment, X is selected from the group consisting of CN; C(O)$OR_8$, wherein $R_8$ is $C_1$-$C_8$ alkyl, optionally substituted with a phenyl; $CH_2OR_{11}$, wherein $R_{11}$ is H, $C_1$-$C_8$ alkyl, or $C_3$-$C_6$ cycloalkyl, wherein $C_1$-$C_8$ alkyl is optionally substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, and morpholinyl; $CH_2NR_9R_{10}$, wherein $R_9$ and $R_{10}$ are independently selected from the group consisting of H and $C_1$-$C_6$ alkyl, or $R_9$ and $R_{10}$ together with the nitrogen to which they are attached form a heterocyclyl ring such as morpholinyl; and $CH_2Z$, wherein Z is halogen. X can be selected as C(O)$OR_8$, wherein $R_8$ is $C_1$-$C_6$ alkyl, optionally substituted with a phenyl, or $CH_2Z$, wherein Z is halogen. More specific examples of suitable X groups include C(O)$OR_8$, wherein $R_8$ is methyl, ethyl, propyl, butyl, t-butyl, or benzyl.

According to another aspect, when X is selected as described above, and is not C(O)OH, each of $R_4$, $R_5$, $R_6$ and $R_7$ can be H. Also, when at least one of $R_4$, $R_5$, $R_6$ and $R_7$ is not H, and is instead selected as described above, X can be C(O)OH. This aspect is especially applicable to Formula (I) compounds.

According to another aspect, compounds of Formula (I) are selected such that W is C(S) or $CH_2$, B is $CH_2$, and $R_1$-$R_7$ are selected as described above.

In other embodiments, $W_1$ is selected from C(O) or $CH_2$. In certain embodiments, $W_1$ is selected from $CH(C_mH_{2m+1})$ and m is an integer selected from 1, 2 or 3. In certain embodiments, Ring $C_1$ is selected from the group consisting of a thienyl ring, a pyridinyl ring, a cyclohexyl ring, a cyclohexenyl ring, a cyclohexa-1,4-dienyl ring, a benzo[d][1,3]dioxolyl ring and a 2,3-dihydrobenzo[b][1,4]dioxinyl ring, each of said rings fused to the moiety of Formula (IIa), wherein benzo[d][1,3]dioxolyl and 2,3-dihydrobenzo[b][1,4]dioxinyl, each having a benzo ring portion, are fused via said benzoportion.

In other embodiments, $R_{20}$ and $R_{21}$ are each H. In certain embodiments, $R_{20}$ and $R_{21}$ are each $C_1$-$C_3$ alkyl. In certain embodiments, $R_{20}$ and $R_{21}$ are taken together with the carbon atom to which they are attached to form carbonyl. In certain embodiments, when X is absent, then $R_{20}$ and $R_{21}$ may be taken together with the carbon atom to which they are attached to form a $C_3$-$C_5$ or $C_3$-$C_6$ cycloalkyl ring selected from cyclopropyl, cyclopentyl or cyclohexyl.

In certain embodiments, $R_{22}$ is selected from the group consisting of H, halogen, $C_1$-$C_4$ alkyl, $C_1$-$C_4$ alkoxy, $C_1$-$C_4$ haloalkyl, cyano, thienyl, furanyl, pyridinyl, pyrimidinyl and phenyl, wherein phenyl is optionally substituted with one or two halogen, $C_1$-$C_4$ alkyl or $C_1$-$C_4$ alkoxy substituents.

In certain embodiments, when one, two or three of $R_{23}$, $R_{24}$, $R_{25}$ and $R_{26}$ are each H, then three, two or one of $R_{23}$, $R_{24}$, $R_{25}$ and $R_{26}$, respectively, are each selected from hydroxyl, halogen, cyano, nitro, $C_1$-$C_8$ alkyl, $C_1$-$C_6$ alkoxy, $C_1$-$C_6$ alkoxyalkoxy, $C_1$-$C_6$ alkoxyalkyl, $C_1$-$C_6$ difluoroalkoxy, $C_1$-$C_6$ trifluoroalkoxy, $C_1$-$C_4$ trifluoroalkyl, $C_2$-$C_6$ alkenyl, $C_2$-$C_4$ trifluoroalkenyl, amino, $C_1$-$C_4$ alkylamino, $C_1$-$C_4$ dialkylamino, $C_1$-$C_4$ aminoalkyl, $C_1$-$C_4$ alkylaminoalkyl or $C_1$-$C_4$ dialkylaminoalkyl.

In certain embodiments, when three of $R_{23}$, $R_{24}$, $R_{25}$ and $R_{26}$ are each H, then one of $R_{23}$, $R_{24}$, $R_{25}$ and $R_{26}$ is selected from phenyl, cyclopentyl, cyclopropyl, benzyloxy, $C_1$-$C_4$ cyclopentylalkoxy, $C_1$-$C_4$ cyclobutylalkoxy, cyclopentyloxy, pyrrolidinyl, piperidinyl, morpholinyl, $C_1$-$C_4$ morpholinylalkyl, thienyl, pyridinyl, pyrimidinyl, or amino, wherein amino is optionally disubstituted with one substituent selected from hydrogen or $C_1$-$C_6$ alkyl and the other is selected from phenyl, $C_1$-$C_4$ alkylcarbonyl, aminocarbonyl, $C_1$-$C_4$ alkylaminocarbonyl, $C_1$-$C_4$ dialkylaminocarbonyl, phenylcarbonyl, phenylaminocarbonyl, N-phenyl-N—$C_1$-$C_4$ alkyl-aminocarbonyl, $C_1$-$C_6$ alkylsulfonyl or phenylsulfonyl, and wherein each instance of phenyl is optionally substituted with one or two substituents selected from halogen, $C_1$-$C_4$ alkyl or $C_1$-$C_4$ alkoxy.

In certain embodiments, $X_1$ is absent or is selected from the group consisting of H, cyano, $C_1$-$C_4$ alkyl, $C_1$-$C_4$ alkoxy, $C_1$-$C_4$ haloalkyl, $C_1$-$C_6$ hydroxylalkyl, $C_1$-$C_6$ alkoxyalkyl, $C_1$-$C_4$ morpholinylalkyl, amino, $C_1$-$C_4$ alkylamino, $C_1$-$C_4$ dialkylamino, $C_1$-$C_4$ aminoalkyl, $C_1$-$C_4$ alkylaminoalkyl, $C_1$-$C_4$ dialkylaminoalkyl, carboxy, $C_1$-$C_6$ alkoxycarbonyl, benzyloxycarbonyl, aminocarbonyl, $C_1$-$C_8$ alkylaminocarbonyl, $C_1$-$C_8$ dialkylaminocarbonyl, hydroxylaminocarbonyl, cyanoaminocarbonyl, phenylaminocarbonyl, aminosulfonylaminocarbonyl, $C_1$-$C_8$ alkylaminosulfonylaminocarbonyl $C_1$-$C_8$ dialkylaminosulfonylaminocarbonyl, $C_1$-$C_8$ alkylsulfonylaminocarbonyl, phenylsulfonylaminocarbonyl, morpholinylcarbonyl and piperidinylcarbonyl.

In one embodiment, a compound useful for the methods provided herein is Compound 1:

Compound 1

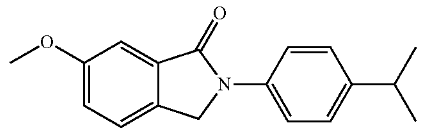

In other embodiments, Compound 1 is also referred to as 2-(4-isopropylphenyl)-6-methoxyisoindolin-1-one.

As those of ordinary skill in the art will appreciate, many of the molecules described herein may contain one or more chiral centers, wherein more than one stereoisomer (e.g., diastereomer or enantiomer) of the molecule may exist. If the stereochemistry of a structure or a portion of a structure is not indicated, for example, with bold or dashed lines, the structure or portion of the structure is to be interpreted as encompassing all stereoisomers of it. Any individual stereoisomers (e.g., diastereomers or enantiomers) of the compounds described herein, as well as mixtures thereof (e.g., racemic mixtures), are specifically contemplated herein.

The compounds described herein can be prepared by any of several techniques known by those skilled in the art. By way of a non-limiting example, the compounds can be prepared as described on pages 11-14 and 245-261 of International Publication No. WO2007/109211, pub. Sep. 27, 2007, which is incorporated by reference herein in its entirety. In a specific embodiment, the compounds for use in the methods described herein include those described in International Publication No. WO 2007/109211, pub. Sep. 27, 2007, which is incorporated by reference herein in its entirety.

Nucleic Acid Constructs

In one aspect, presented herein are nucleic acid constructs for use in cell-based and cell-free screening assays for the identification or validation of compounds that cause ribosomal frameshifting. In another aspect, presented herein are nucleic acid constructs for cell-based and cell-free screening assays for the identification or validation of compounds that produce a stabilized SMNΔEx7 protein.

Presented herein are nucleic acid constructs comprising nucleic acid residues of an exon(s) of SMN or a fragment thereof, a reporter gene coding sequence lacking a start codon, and in some instances, nucleic acid residues of an intron(s) of SMN. In specific aspects, a nucleic acid construct described herein comprises a fragment of the nucleic residues of an exon 8 of SMN fused to a reporter gene coding sequence lacking the start codon, wherein that the first codon of the reporter gene coding sequence and the first codon of the fragment are out of frame with each other in the mRNA transcript transcribed from the nucleic acid construct and the presence of a stop codon in the mRNA transcript causes translation termination prior to translation of the reporter gene coding sequence (i.e., an aberrant stop codon). In such mRNA transcripts, the first start codon and the aberrant stop codon are in the same contiguous open reading frame without any interruption by, e.g., a stop codon. In the presence of certain compounds, the open reading frame may shift so that the start codon and the aberrant stop codon are no longer in the same open reading frame, and instead the first start codon and the stop codon found at the end of the reporter gene coding sequence are in the same contiguous open reading frame without any interruptions. As a result, an increase in fusion protein with activity of the reporter gene coding sequence can be detected.

In one aspect, the nucleic acid constructs described herein comprise deoxyribonucleic acid (DNA) residues or analogs thereof. In one embodiment, a nucleic acid construct comprises, in 5' to 3' order: (i) a fragment of the nucleic acid residues of exon 8 of SMN; and (ii) a reporter gene coding sequence lacking a start codon, wherein the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and a stop codon is upstream of the reporter gene in the mRNA transcript. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In certain embodiments, the fragment of the nucleic acid residues of exon 8 of SMN consists of the first 3, 5, 7, or 9 nucleotides from the 5' end of exon 8 of SMN. In other embodiments, the fragment of the nucleic acid residues of exon 8 of SMN consists of the first 11, 13, 15, 17, or 19 nucleotides from the 5' end of exon 8 of SMN. In a specific embodiment, the fragment of the nucleic acid residues of exon 8 SMN consists of the first 21 nucleotides from the 5' end of exon 8 of SMN. In another specific embodiment, the fragment of the nucleic acid residues of exon 8 of SMN consists of the first 23 nucleotides from the 5' end of exon 8 of SMN. In certain embodiments, the nucleic acid construct comprises a start codon upstream (5') to the fragment of the nucleic acid residues of exon 8 of SMN. In some embodiments, the nucleic acid construct comprises one or more nucleotide sequences encoding one or more amino acid sequence (e.g., peptides or polypeptides), wherein said one or more nucleotide sequences are upstream (5') of the fragment of the nucleic acid residues of exon 8 of SMN, and wherein the first codon of each of the one or more nucleotide sequences and the first codon of the fragment are in frame with the each other in the mRNA transcript transcribed from the nucleic acid construct. In a specific embodiment, the one or more nucleotide sequences encoding one or more amino acid sequence (e.g., peptides or polypeptides) upstream (5') of the fragment of the nucleic acid residues of exon 8 of SMN contains a start codon. In accordance with such embodiments, the first start codon and the stop codon upstream of the reporter gene coding sequence are in the same contiguous open reading frame.

In another embodiment, a nucleic acid construct comprises, in 5' to 3' order: (a) a start codon; (b) a fragment of the nucleic acid residues of exon 8 of SMN; and (c) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and a stop codon is upstream of the reporter gene coding sequence in the mRNA transcript; and (ii) the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon, (b) a fragment of the nucleic acid residues of exon 7 of SMN; (c) a fragment of the nucleic acid residues of exon 8 of SMN; and (d) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); (ii) in the mRNA transcript transcribed from the nucleic acid construct, the first start codon and the stop codon upstream of the reporter gene coding sequence are in the same contiguous open reading frame without any interruption by, e.g., a stop codon; and (iii) the fragment of the nucleic acid residues of exon 7 of SMN comprises any number of nucleotides of exon 7 of SMN so long as in the mRNA transcript transcribed from the nucleic acid construct the first start codon and the stop codon upstream of the reporter gene coding sequence are maintained in the same contiguous open reading frame without any interruption by, e.g., stop codon. In certain embodiments, the first codon of the fragment of the nucleic acid residues of exon 7 of SMN and the first codon of the fragment of the nucleic acid residues of exon 8 of SMN are in frame with each other in the mRNA transcript transcribed from the nucleic acid construct. In certain embodiments, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In some embodiments, the nucleic acid construct comprises one or more nucleotide sequences encoding one or more amino acid sequences (e.g., peptides or polypeptides), wherein said one or more nucleotide sequences are upstream (5') of the fragment of the nucleic acid residues of exon 7 of SMN and downstream (3') to the start codon. In certain embodiments, the first codon of each of the one or more nucleotide sequences encoding the one or more amino acid sequences, the first codon of the fragment of the nucleic acid residues of exon 7 of SMN, and the first codon of the fragment of the nucleic acid residues of exon 8 of SMN are in frame with one another in the mRNA transcript transcribed from the nucleic acid construct. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) a fragment of the nucleic acid residues of exon 7 of SMN; (c) a fragment of the nucleic acid residues of exon 8 of SMN; and (d) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter coding sequence); (ii) in the mRNA transcript transcribed from the nucleic acid construct, the first start codon and the stop codon upstream of the reporter gene coding sequence are in the same contiguous open reading frame without any interruption by, e.g., a stop codon; and (iii) the fragment of the nucleic acid residues of exon 7 of SMN comprises any number of nucleotides of exon 7 of SMN so long as in the mRNA transcript transcribed from the nucleic acid construct the first start codon and the stop codon upstream of the reporter gene coding sequence are maintained in the same contiguous open reading frame without any interruption by, e.g., stop codon. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In certain embodiments, an internal start codon (e.g., ATG) in the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof. In some embodiments, the first codon of the nucleic acid residues of exon 6 of SMN or a fragment thereof, the first codon of the fragment of the nucleic acid residues of exon 7 of SMN, and the first codon of the fragment of exon 8 of SMN are in frame with each other in the mRNA transcript transcribed from the nucleic acid construct. In some embodiments, the nucleic acid construct comprises one or more nucleotide sequences encoding one or more amino acid sequences (e.g., peptides or polypeptides), wherein said one or more nucleotide sequences are upstream (5') of the nucleic acid residues of exon 6 of SMN or a fragment thereof, and wherein the first codon of each of the one or more nucleotide sequences, the first codon of the nucleic acid residues of exon 6 of SMN or a fragment thereof, and the first codon of the fragment of the nucleic acid residues of exon 8 of SMN are in frame with one another in the mRNA transcript transcribed from the nucleic acid construct. In certain embodiments, the one or more nucleotide sequences encoding amino acid sequences (e.g., peptides or polypeptides) upstream of the nucleic acid residues of exon 6 of SMN or a fragment thereof contains a start codon. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) a start codon; (b) a fragment of the nucleic acid residues of exon 7 of SMN; (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); (ii) in the mRNA transcript transcribed from the nucleic acid construct, the first start codon and the stop codon upstream of the reporter gene coding sequence are in the same contiguous open reading frame without any interruption by, e.g., a stop codon; and (iii) the fragment of the nucleic acid residues of exon 7 of SMN comprises any number of nucleotides of exon 7 of SMN required for splicing and so long as in the mRNA transcript transcribed from the nucleic acid construct the start codon and the stop codon upstream of the reporter gene coding sequence are maintained in the same contiguous open reading frame without any interruption by, e.g., stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In a specific embodiment, the fragment of the nucleic acid residues of exon 7 of SMN comprises the first two nucleotides from the 3' end of exon 7 of SMN (i.e., nucleotide residues 53 and 54 from the 5' end of exon 7 of SMN). In another specific embodiment, the fragment of the nucleic acid residues of exon 7 of SMN comprises a minimum of the first two or six nucleotides from the 3' end of exon 7 of SMN (i.e., nucleotide residues 49 to 54 from the 5' end of exon 7 of SMN). In some embodiments, the nucleic acid construct comprises one or more nucleotide sequences encoding one or more amino acid sequences (e.g., peptides or polypeptides), wherein said one or more nucleotide sequences are upstream (5') of the fragment of the nucleic acid residues of exon 7 of SMN and downstream (3') to the start codon. In certain embodiments, the first codon of each of the one or more nucleotide sequences encoding the one or more amino acid sequences, the first codon of the fragment of the nucleic acid residues of exon 7 of SMN, and the first codon of the fragment of the nucleic acid residues of exon 8 of SMN are in frame with one another in the mRNA transcript transcribed from the nucleic acid construct. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) a fragment of the nucleic acid residues of exon 7 of SMN; (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); (ii) the fragment of the nucleic acid residues of exon 6 of SMN comprises any number of nucleotides of exon 6 of SMN so long as in the mRNA transcript transcribed from the nucleic acid construct the first codon of the fragment of the nucleic acid residues of exon 6 of SMN and the first codon of the fragment of the nucleic acid residues of exon 8 of SMN are in frame with each other; and (iii) the fragment of the nucleic acid residues of exon 7 of SMN comprises a minimum of the nucleotides of exon 7 of SMN required for splicing and in the mRNA transcript transcribed from the nucleic acid construct the first start codon and the stop codon upstream of the reporter gene coding sequence are in the same contiguous open reading frame without any interruption by, e.g., a stop codon. In some embodiments, in the mRNA transcript transcribed from the nucleic acid construct, the regions of the mRNA transcript corresponding to the fragments of the nucleic acid residues of exon 6 and exon 7 of SMN do not contain a stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In a specific embodiment, the fragment of the nucleic acid residues of exon 7 of SMN comprises a minimum of the first nucleotide from the 5' end of exon 7 of SMN and the first two nucleotides from the 3' end of exon 7 of SMN (i.e., nucleotide residues 53 and 54 from the 5' end of exon 7 of SMN). In another specific embodiment, the fragment of the nucleic acid residues of exon 7 of SMN comprises a minimum of the first two or six nucleotides from the 3' end of exon 7 of SMN (i.e., nucleotide residues 49 to 54 from the 5' end of exon 7 of SMN). In certain embodiments, an internal start codon (e.g., ATG) in the nucleic acid residues of exon 6 of SMN or a fragment thereof is used as a start codon for the nucleic acid construct. In some embodiments, the nucleic acid construct comprises a start codon upstream (5') to the nucleic acid residues of exon 6 of SMN or a fragment thereof. In some embodiments, the nucleic acid construct comprises one or more nucleotide sequences encoding one or more amino acid sequences (e.g., peptides or polypeptides), wherein said one or more nucleotide sequences are upstream (5') of the nucleic acid residues of exon 6 of SMN or a fragment thereof, and wherein the first codon of each of the one or more nucleotide sequences. In some embodiments, the first codon of the nucleic acid residues of exon 6 of SMN or a fragment thereof, and the first codon of the fragment of the nucleic acid residues of exon 8 of SMN are in frame with one another in the mRNA transcript transcribed from the nucleic acid construct. In certain embodiments, the one or more nucleotide sequences encoding amino acid sequences (e.g., peptides or polypeptides) upstream of the nucleic acid residues of exon 6 of SMN or a fragment thereof contains a start codon. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of intron 6 of SMN or a fragment thereof, wherein the fragment of the nucleic acid residues of intron 6 of SMN comprises any number of nucleotides of intron 6 of SMN required for a functional, minimum intron; (c) a fragment of the nucleic acid residues of exon 7 of SMN; (d) the nucleic acid residues of intron 7 of SMN or a fragment thereof, wherein the fragment of the nucleic acid residues of intron 7 comprises any number of nucleotides of intron 7 of SMN required for a functional, minimum intron; (e) a fragment of the nucleic acid residues of exon 8 of SMN; and (f) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); (ii) the fragment of the nucleic acid residues of exon 6 of SMN comprises a minimum of the nucleotides of exon 6 of SMN required for splicing so long as in the mRNA transcript transcribed from the nucleic acid construct the first start codon and the stop codon upstream of the reporter gene coding sequence are in the same contiguous open reading frame without any interruption by, e.g., a stop codon; and (iii) the fragment of the nucleic acid residues of exon 7 of SMN comprises a minimum of the nucleotides of exon 7 of SMN required for splicing so long as in the mRNA transcript transcribed from the nucleic acid construct the first start codon and the stop codon upstream of the reporter gene coding sequence are in the same contiguous open reading frame without any interruption by, e.g., a stop codon. In certain embodiments, the first codon of the nucleic acid residues of exon 6 of SMN or fragment thereof, the first codon of the fragment of the nucleic acid residues of exon 7 of SMN and the first codon of the fragment of the nucleic acid residues of exon 8 of SMN are in frame with each other. In some embodiments, in the mRNA transcript transcribed from the nucleic acid construct, the regions of the mRNA transcript corresponding to the fragments of the nucleic acid residues of exon 6 and exon 7 of SMN do not contain a stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In a specific embodiment, the fragment of the nucleic acid residues of exon 7 of SMN comprises a minimum of the first nucleotide from the 5' end of exon 7 of SMN and the first two nucleotides from the 3' end of exon 7 of SMN (i.e., nucleotide residues 53 and 54 from the 5' end of exon 7 of SMN). In another specific embodiment, the fragment of the nucleic acid residues of exon 7 of SMN comprises a minimum of the first two or six nucleotides from the 3' end of exon 7 of SMN (i.e., nucleotide residues 49 to 54 from the 5' end of exon 7 of SMN). In certain embodiments, the fragment of the nucleic acid residues of exon 6 of SMN comprises a minimum of the first two nucleotides from the 3' end of exon 6 of SMN. In other embodiments, the fragment of exon 6 of SMN comprises a minimum of the first three nucleotides from the 3' end of exon 6 of SMN. In certain embodiments, an internal start codon (e.g., an ATG) of the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof. In some embodiments, the nucleic acid construct comprises one or more nucleotide sequences encoding one or more amino acid sequences (e.g., peptides or polypeptides), wherein said one or more nucleotide sequences are upstream (5') of the nucleic acid residues of exon 6 of SMN or a fragment thereof, and wherein the first codon of each of the one or more nucleotide sequences, the first codon of the nucleic acid residues of exon 6 of SMN or a fragment thereof, and the first codon of the fragment of the nucleic acid residues of exon 8 of SMN are in frame with one another in the mRNA transcript transcribed from the nucleic acid construct. In some embodiments, the first codon of the nucleic acid residues of exon 6 of SMN or a fragment thereof, the first codon of the fragment of the nucleic acid residues of exon 7 of SMN, and the first codon of the fragment of exon 8 of SMN are in frame with each other in the mRNA transcript transcribed from the nucleic acid construct. In certain embodiments, the one or more nucleotide sequences encoding amino acid sequences (e.g., peptides or polypeptides) upstream of the nucleic acid residues of exon 6 of SMN or a fragment thereof contains a start codon. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) a start codon; (b) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (c) a fragment of the nucleic acid residues of exon 8 of SMN; and (d) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); (ii) in the mRNA transcript transcribed from the nucleic acid construct, the first start codon and the stop codon upstream of the reporter gene coding sequence are in the same contiguous open reading frame without any interruption by, e.g., a stop codon. In some embodiments the first codon of the nucleic acid residues of exon 7 of SMN, and the first codon of the fragment of exon 8 of SMN are in frame with each other in the mRNA transcript transcribed from the nucleic acid construct. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In a specific embodiment, a single nucleotide residue is inserted after the 48th nucleotide residue from the 5' end of exon 7 of SMN (i.e., before the 6th nucleotide from the 3' end of exon 7 of SMN). In some embodiments, the nucleic acid construct comprises one or more nucleotide sequences encoding one or more amino acid sequence (e.g., peptides or polypeptides), wherein said one or more nucleotide sequences are upstream (5') of the nucleic acid residues of exon 7 of SMN, and wherein the first codon of each of the one or more nucleotide sequences, the first codon of the nucleic acid residues of exon 7 of SMN, and the first codon of the fragment of the nucleic acid residues of exon 8 of SMN are in frame with one another in the mRNA transcript transcribed from the nucleic acid construct. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (c) a fragment of the nucleic acid residues of exon 8 of SMN; and (d) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); (ii) in the mRNA transcript transcribed from the nucleic acid construct the first start codon and the stop codon upstream of the reporter gene coding sequence are in the same contiguous open reading frame without any interruption by, e.g., a stop codon; and (iii) the fragment of the nucleic acid residues of exon 6 of SMN comprises any number of nucleotides of exon 6 of SMN so long as in the mRNA transcript transcribed from the nucleic acid construct in the mRNA transcript transcribed from the nucleic acid construct the first start codon and the stop codon upstream of the reporter gene coding sequence are in the same contiguous open reading frame without any interruption by, e.g., a stop codon. In some embodiments, in the mRNA transcript transcribed from the nucleic acid construct, the regions of the mRNA transcript corresponding to the fragment of the nucleic acid residues of exon 6 of SMN and the nucleic acid residues of exon 7 of SMN do not contain a stop codon. In some embodiments, the first codon of the nucleic acid residues of exon 6 of SMN or a fragment thereof, the first codon of the nucleic acid residues of exon 7 of SMN, and the first codon of the fragment of exon 8 of SMN are in frame with each other in the mRNA transcript transcribed from the nucleic acid construct. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In a specific embodiment, a single nucleotide residue is inserted after the 48th nucleotide residue from the 5' end of exon 7 of SMN (i.e., before the 6th nucleotide from the 3' end of exon 7 of SMN). In certain embodiments, an internal start codon (e.g., an ATG) in the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof. In some embodiments, the nucleic acid construct comprises one or more nucleotide sequences encoding one or more amino acid sequence (e.g., peptides or polypeptides), wherein said one or more nucleotide sequences are upstream (5') of the nucleic acid residues of exon 6 of SMN or a fragment thereof, and wherein the first codon of each of the one or more nucleotide sequences, the first codon of the nucleic acid residues of exon 6 of SMN or a fragment thereof, and the first codon of the fragment of the nucleic acid residues of exon 8 of SMN are in frame with one another in the mRNA transcript transcribed from the nucleic acid construct. In certain embodiments, the one or more nucleotide sequences encoding amino acid sequences (e.g., peptides or polypeptides) upstream of the nucleic acid residues of exon 6 of SMN or a fragment thereof contains a start codon. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) a start codon; (b) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); (ii) in the mRNA transcript transcribed from the nucleic acid construct, the first start codon and the stop codon upstream of the reporter gene coding sequence are in the same contiguous open reading frame without any interruption by, e.g., a stop codon. In some embodiments, the first codon of the nucleic acid residues of exon 7 of SMN and the first codon of the fragment of exon 8 of SMN are in frame with each other in the mRNA transcript transcribed from the nucleic acid construct. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In a specific embodiment, a single nucleotide residue is inserted after the 48th nucleotide residue from the 5' end of exon 7 of SMN (i.e., before the 6th nucleotide from the 3' end of exon 7 of SMN). In some embodiments, the nucleic acid construct comprises one or more nucleotide sequences encoding one or more amino acid sequence (e.g., peptides or polypeptides), wherein said one or more nucleotide sequences are upstream (5') of the nucleic acid residues of exon 7 of SMN, and wherein the first codon of each of the one or more nucleotide sequences, the first codon of the nucleic acid residues of exon 7 of SMN, and the first codon of the fragment of the nucleic acid residues of exon 8 of SMN are in frame with one another in the mRNA transcript transcribed from the nucleic acid construct. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); and (ii) in the mRNA transcript transcribed from the nucleic acid construct, the first start codon and the stop codon upstream from the reporter gene coding sequence are in the same contiguous open reading frame without any interruption by, e.g., a stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In a specific embodiment, a single nucleotide residue is inserted after the 48th nucleotide residue from the 5' end of exon 7 of SMN (i.e., before the 6th nucleotide from the 3' end of exon 7 of SMN). In certain embodiments, an internal start codon (e.g., an ATG) of the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof. In some embodiments, the nucleic acid construct comprises one or more nucleotide sequences encoding one or more amino acid sequence (e.g., peptides or polypeptides), wherein said one or more nucleotide sequences are upstream (5') of the nucleic acid residues of exon 6 of SMN or a fragment thereof, and wherein the first codon of each of the one or more nucleotide sequences, the first codon of the nucleic acid residues of exon 6 of SMN or a fragment thereof, and the first codon of the fragment of the nucleic acid residues of exon 8 of SMN are in frame with one another in the mRNA transcript transcribed from the nucleic acid construct. In certain embodiments, the one or more nucleotide sequences encoding amino acid sequences (e.g., peptides or polypeptides) upstream of the nucleic acid residues of exon 6 of SMN or a fragment thereof contains a start codon. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) the nucleic acid residues of exon 6 of SMN or a fragment thereof; (b) the nucleic, acid residues of intron 6 of SMN or a fragment thereof, wherein the fragment of the nucleic acid residues of intron 6 of SMN comprises any number of nucleotides of intron 6 of SMN required for a functional, minimum intron; (c) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (d) the nucleic acid residues of intron 7 of SMN or a fragment thereof, wherein the fragment of the nucleic acid residues of intron 7 comprises any number of nucleotides of intron 7 of SMN required for a functional, minimum intron; (e) a fragment of the nucleic acid residues of exon 8 of SMN; and (f) a reporter gene coding sequence lacking a start codon, wherein: (i) the fragment of the nucleic acid residues of exon 6 of SMN comprises a minimum of the nucleotides of exon 6 of SMN required for splicing; (ii) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); and (iii) in the mRNA transcript transcribed from the nucleic acid construct the first start codon and the stop codon upstream of the reporter gene coding sequence are in the same contiguous open reading frame without any interruption by, e.g., a stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In a specific embodiment, a single nucleotide residue is inserted after the 48th nucleotide residue from the 5' end of exon 7 of SMN (i.e., before the 6th nucleotide from the 3' end of exon 7 of SMN). In certain embodiments, the fragment of the nucleic acid residues of exon 6 of SMN comprises a minimum of the first three nucleotides from the 3' end of exon 6 of SMN. In other embodiments, the fragment of exon 6 of SMN comprises a minimum of the first three nucleotides from the 3' end of exon 6 of SMN. In certain embodiments, an internal start codon (e.g., an ATG) of the nucleic acid residues of exon 6 of SMN or a fragment thereof is used as a start codon for the nucleic acid construct. In some embodiments, the nucleic acid construct comprises one or more nucleotide sequences encoding one or more amino acid sequence (e.g., peptides or polypeptides), wherein said one or more nucleotide sequences are upstream (5') of the nucleic acid residues of exon 6 of SMN or a fragment thereof, and wherein the first codon of each of the one or more nucleotide sequences, the first codon of the nucleic acid residues of exon 6 of SMN or a fragment thereof, the first codon of the nucleic acid residues of exon 7 of SMN, and the first codon of the fragment of the nucleic acid residues of exon 8 of SMN are in frame with one another in the mRNA transcript transcribed from the nucleic acid construct. In certain embodiments, the one or more nucleotide sequences encoding amino acid sequences (e.g., peptides or polypeptides) upstream of the nucleic acid residues of exon 6 of SMN or a fragment thereof contains a start codon. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) a start codon; (b) the nucleic acid residues of exon 7 of SMN, wherein a single guanine residue is inserted after the 48th nucleotide residue from the 5' end of exon 7 of SMN (i.e., before the 6th nucleotide from the 3' end of exon 7 of SMN); (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); (ii) in the mRNA transcript transcribed from the nucleic acid construct, the first start codon and the stop codon upstream of the reporter gene coding sequence are in the same contiguous open reading frame without any interruption by, e.g., a stop codon. In some embodiments, the first codon of the nucleic acid residues of exon 7 of SMN and the first codon of the fragment of exon 8 of SMN are in frame with each other in the mRNA transcript transcribed from the nucleic acid construct. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In some embodiments, the nucleic acid construct comprises one or more nucleotide sequences encoding one or more amino acid sequence (e.g., peptides or polypeptides), wherein said one or more nucleotide sequences are upstream (5') of the nucleic acid residues of exon 7 of SMN, and wherein the first codon of each of the one or more nucleotide sequences, the first codon of the nucleic acid residues of exon 7 of SMN, and the first codon of the fragment of the nucleic acid residues of exon 8 of SMN are in frame with one another in the mRNA transcript transcribed from the nucleic acid construct. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of exon 7 of SMN, wherein a single guanine residue is inserted after the 48th nucleotide residue from the 5' end of exon 7 of SMN (i.e., before the 6th nucleotide from the 3' end of exon 7 of SMN); (c) the nucleic acid residues of intron 7 of SMN or a fragment thereof, wherein the fragment of intron 7 of SMN comprises any number of nucleotides of intron 7 of SMN required for a functional, minimum intron; (d) a fragment of the nucleic acid residues of exon 8 of SMN; and (e) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon. In some embodiments, the first codon of the nucleic acid residues of exon 6 of SMN or a fragment thereof, the first codon of the nucleic acid residues of exon 7 of SMN, and the first codon of the fragment of exon 8 of SMN are in frame with each other in the mRNA transcript transcribed from the nucleic acid construct. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In certain embodiments, an internal start codon (e.g., an ATG) in the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof. In some embodiments, the nucleic acid construct comprises one or more nucleotide sequences encoding one or more amino acid sequence (e.g., peptides or polypeptides), wherein said one or more nucleotide sequences are upstream (5') of the nucleic acid residues of exon 6 of SMN or a fragment thereof, and wherein the first codon of each of the one or more nucleotide sequences, the first codon of the nucleic acid residues of exon 6 of SMN or a fragment thereof, the first codon of the nucleic acid residues of exon 7 of SMN, and the first codon of the fragment of the nucleic acid residues of exon 8 of SMN are in frame with one another in the mRNA transcript transcribed from the nucleic acid construct. In certain embodiments, the one or more nucleotide sequences encoding amino acid sequences (e.g., peptides or polypeptides) upstream of the nucleic acid residues of exon 6 of SMN or a fragment thereof contains a start codon. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) the nucleic acid residues of exon 6 of SMN or a fragment thereof; (b) the nucleic acid residues of intron 6 of SMN or a fragment thereof, wherein the fragment of the nucleic acid residues of intron 6 of SMN comprises any number of nucleotides of intron 6 required for a functional, minimum intron; (c) the nucleic acid residues of exon 7 of SMN, wherein a single guanine residue is inserted after the 48th nucleotide residue from the 5' end of exon 7 of SMN (i.e., before the 6th nucleotide from the 3' end of exon 7 of SAM); (d) the nucleic acid residues of intron 7 of SMN or a fragment thereof, wherein the fragment of intron 7 of SMN comprises any number of nucleotides of intron 7 of SMN required for a functional, minimum intron; (e) a fragment of the nucleic acid residues of exon 8 of SMN; and (f) a reporter gene coding sequence lacking a start codon, wherein (i) the fragment of the nucleic acid residues of exon 6 of SMN comprises a minimum of the nucleotides of exon 6 of SMN required for splicing; (ii) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (iii) the production of the mRNA transcript generates a stop codon in the region of the mRNA transcript that corresponds to the fragment of the nucleic acid residues of exon 8 of SMN (i.e., upstream of the reporter gene coding sequence); and (iv) in the mRNA transcript transcribed from the nucleic acid construct, the first start codon and the stop codon upstream from the reporter gene coding sequence are in the same contiguous open reading frame without any interruption by, e.g., a stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In certain embodiments, the fragment of the nucleic acid residues of exon 6 of SMN comprises a minimum of the first two nucleotides from the 3' end of exon 6 of SMN. In other embodiments, the fragment of exon 6 of SMN comprises a minimum of the first three nucleotides from the 3' end of exon 6 of SMN. In certain embodiments, an internal start codon (e.g., an ATG) in the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof. In some embodiments, the nucleic acid construct comprises one or more nucleotide sequences encoding one or more amino acid sequence (e.g., peptides or polypeptides), wherein said one or more nucleotide sequences are upstream (5') of the nucleic acid residues of exon 6 of SMN or a fragment thereof, and wherein the first codon of each of the one or more nucleotide sequences, the first codon of the nucleic acid residues of exon 6 of SMN or a fragment thereof, the first codon of the nucleic acid residues of exon 7 of SMN, and the first codon of the fragment of the nucleic acid residues of exon 8 of SMN are in frame with one another in the mRNA transcript transcribed from the nucleic acid construct. In certain embodiments, the one or more nucleotide sequences encoding amino acid sequences (e.g., peptides or polypeptides) upstream of the nucleic acid residues of exon 6 of SMN or a fragment thereof contains a start codon. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) a start codon; (b) a minimum of one nucleotide; (c) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN) and wherein a single guanine residue is inserted into the fragment of the nucleic acid residues of exon 7 of SMN at the location that corresponds to the location in exon 7 of SMN that is after the 48th nucleotide from the 5' end of exon 7 of SMN; (d) the nucleic acid residues of intron 7 of SMN or a fragment thereof, wherein the fragment of the nucleic acid residues of intron 7 of SMN comprises any number of nucleotides of intron 7 required for a functional, minimum intron; (e) a fragment of the nucleic acid residues of exon 8 of SMN; and (f) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon. In some embodiments, the first codon of the fragment of the nucleic acid residues of exon 7 of SMN and the first codon of the fragment of exon 8 of SMN are in frame with each other in the mRNA transcript transcribed from the nucleic acid construct. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In certain embodiments, the nucleic acid construct comprises a start codon upstream (5') to the minimum of one nucleotide.

In another embodiment, a nucleic acid construct comprises, in 5' to 3' order: (a) a start codon; (b) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN), wherein a single guanine residue is inserted into the fragment of the nucleic acid residues of exon 7 of SMN at the location that corresponds to the location in exon 7 of SMN that is after the 48th nucleotide from the 5' end of exon 7 of SMN, and wherein the fragment of the nucleic acid residues of exon 7 of SMN comprises any number of nucleotides of exon 7 required for splicing; (c) the nucleic acid residues of intron 7 of SMN or a fragment thereof, wherein the fragment of the nucleic acid residues of intron 7 of SMN comprises any number of nucleotides of intron 7 required for a functional, minimum intron; (d) a fragment of the nucleic acid residues of exon 8 of SMN; and (e) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In certain embodiments, the nucleic acid construct comprises a start codon upstream (5') to the fragment of the nucleic acid residues of exon 7 of SMN.

In a specific embodiment, a nucleic acid construct comprises, in 5' to 3' order: (a) a start codon; (b) a minimum of one nucleotide; (c) a fragment of the nucleic acid residues of exon 7 of SMN, wherein the fragment of the nucleic acid residues of exon 7 of SMN consists of the first six nucleotides from the 3' end of exon 7 of SMN (i.e., nucleotide residues 49 to 54 from the 5' end of exon 7 of SMN) and wherein a single guanine residue is inserted upstream (5') of the fragment of the nucleic acid residues of exon 7 of SMN; (d) the nucleic acid residues of intron 7 of SMN or a fragment thereof, wherein the fragment of the nucleic acid residues of intron 7 of SMN comprises any number of nucleotides of intron 7 required for a functional, minimum intron; (e) a fragment of the nucleic acid residues of exon 8 of SMN; and (f) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In certain embodiments, the nucleic acid construct comprises a start codon upstream (5') to the minimum of one nucleotide.

In a specific embodiment, a nucleic acid construct comprises, in 5' to 3' order: (a) a start codon; (b) a fragment of the nucleic acid residues of exon 7 of SMN, wherein the fragment of the nucleic acid residues of exon 7 of SMN consists of the first six nucleotides from the 3' end of exon 7 of SMN (i.e., nucleotide residues 49 to 54 from the 5' end of exon 7 of SMN), wherein a single guanine residue is inserted upstream (5') of the fragment of the nucleic acid residues of exon 7 of SMN, and wherein the fragment of the nucleic acid residues of exon 7 of SMN comprises any number of nucleotides of exon 7 required for splicing; (c) the nucleic acid residues of intron 7 of SMN or a fragment thereof, wherein the fragment of the nucleic acid residues of intron 7 of SMN comprises any number of nucleotides of intron 7 required for a functional, minimum intron; (d) a fragment of the nucleic acid residues of exon 8 of SMN; and (e) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon. In some embodiments, the first codon of the fragment of the nucleic acid residues of exon 7 of SMN and the first codon of the fragment of exon 8 of SMN are in frame with each other in the mRNA transcript transcribed from the nucleic acid construct. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In certain embodiments, the nucleic acid construct comprises a start codon upstream (5') to the fragment of the nucleic acid residues of exon 7 of SMN.

In another embodiment, a nucleic acid construct comprises, in 5' to 3' order: (a) the nucleic acid residues of exon 6 of SMN or a fragment thereof; (b) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN) and wherein a single guanine residue is inserted into the fragment of the nucleic acid residues of exon 7 of SMN at the location that corresponds to the location in exon 7 of SMN that is after the 48th nucleotide from the 5' end of exon 7 of SMN; (c) the nucleic acid residues of intron 7 of SMN or a fragment thereof, wherein the fragment of the nucleic acid residues of intron 7 of SMN comprises any number of nucleotides of intron 7 required for a functional, minimum intron; (d) a fragment of the nucleic acid residues of exon 8 of SMN; and (e) a reporter gene coding sequence lacking a start codon, wherein (i) the reporter gene coding sequence is fused to the fragment of the nucleic acid residues of exon 8 of SMN such that the first codon of the reporter gene coding sequence and the first codon fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In certain embodiments, an internal start codon (e.g., an ATG) in the nucleic acid residues of exon 6 of SMN or a fragment thereof is used as a start codon for the nucleic acid construct. In some embodiments, the nucleic acid construct comprises a start codon upstream (5') of the nucleic acid residues of exon 6 of SMN or a fragment thereof.

In another embodiment, a nucleic acid construct comprises, in 5' to 3' order: (a) the nucleic acid residues of exon 6 of SMN or a fragment thereof; (b) the nucleic acid residues of intron 6 of SMN or a fragment thereof, wherein the fragment of the nucleic acid residues of SMN comprises any number of nucleotides of intron 6 of SMN for a functional, minimum intron; (c) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN) and wherein a single guanine residue is inserted into the fragment of the nucleic acid residues of exon 7 of SMN at the location that corresponds to the location in exon 7 of SMN that is after the 48th nucleotide from the 5' end of exon 7 of SMN; (d) the nucleic acid residues of intron 7 of SMN or a fragment thereof, wherein the fragment of the nucleic acid residues of intron 7 of SMN comprises any number of nucleotides of intron 7 required for a functional, minimum intron; (e) a fragment of the nucleic acid residues of exon 8 of SMN; and (f) a reporter gene coding sequence lacking a start codon, wherein (i) the fragment of the nucleic acid residues of exon 6 of SMN comprises a minimum of the nucleotides of exon 6 of SMN required for splicing; (ii) the reporter gene coding sequence is fused to the fragment of the nucleic acid residues of exon 8 of SMN such that the first codon of the reporter gene coding sequence and the first codon fragment are out of frame with each other in the mRNA transcript transcribed from the nucleic acid construct; (iii) the production of the mRNA transcript generates a stop codon in the region of the mRNA transcript that corresponds to the fragment of the nucleic acid residues of exon 8 of SMN (i.e., upstream of the reporter gene coding sequence); and (iv) in the mRNA transcript transcribed from the nucleic acid construct, the first start codon and the stop codon upstream from the reporter gene coding sequence are in the same contiguous open reading frame without any interruption by, e.g., a stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In a specific embodiment, the fragment of the nucleic acid residues of exon 7 of SMN comprises a minimum of the first nucleotide from the 5' end of exon 7 of SMN and the first two nucleotides from the 3' end of exon 7 of SMN (i.e., nucleotide residues 53 and 54 from the 5' end of exon 7 of SMN). In another specific embodiment, the fragment of the nucleic acid residues of exon 7 of SMN comprises a minimum of the first two or six nucleotides from the 3' end of exon 7 of SMN (i.e., nucleotide residues 49 to 54 from the 5' end of exon 7 of SMN). In another specific embodiment, the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN). In certain embodiments, the fragment of exon 6 of SMN comprises a minimum of the first two nucleotides from the 3' end of exon 6 of SMN. In other embodiments, the fragment of exon 6 of SMN comprises a minimum of the first three nucleotides from the 3' end of exon 6 of SMN. In certain embodiments, an internal start codon (e.g., an ATG) in the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof.

In certain embodiments, the term "a functional, minimum intron" in the context of a fragment of the nucleic acid residues of intron 6 of SMN or a fragment of the nucleic acid residues of intron 7 of SMN refers to a fragment that comprises at least six nucleotides of the 5' splice site of intron 6 or intron 7 of SMN and three nucleotides plus the polypyrimidine tract and the branch-point sequence of the 3' splice site of intron 6 or intron 7 of SMN. In one embodiment, the fragment comprises the minimal number of nucleic acids required for an intron to permit the retention of the nucleotides of the exons flanking the intron after splicing. In one embodiment, the 3' splice site plus the polypyrimidine tract and the branch-point sequence of the 3' splice comprises about 40 nucleic acid residues of the 3' splice site of intron 6 or intron 7 of SMN. In another embodiment, the 3' splice site plus the polypyrimidine tract and the branch-point sequence of the 3' splice comprises 20 nucleic acid residues of the 3' splice site of intron 6 or intron 7 of SMN.

In certain embodiments, the term "minimum of the nucleotides of exon 6 of SMN required for splicing" refers to a fragment of exon 6 of SMN that permits removal of an intron via mRNA splicing and maintains the complete sequence of the mRNA fragment included (or encoded) in a nucleic acid construct. In a specific embodiment, the fragment includes the intact 3' end of exon 6 of SMN. In another embodiment, the fragment of exon 6 of SMN is at least 3, at least 6, at least 9, or at least 12 nucleic acids long. In a specific embodiment, the intact 3' end of the fragment of exon 6 of SMN at least 6, at least 9, or at least 12 nucleic acids long.

In certain embodiments, the term "minimum of the nucleotides of exon 7 of SMN required for splicing" refers to a fragment of exon 7 of SMN that permits removal of an intron via mRNA splicing and maintains the complete sequence of the mRNA fragment included (or encoded) in a nucleic acid construct.

In certain aspects, an RNA transcript transcribed from a nucleic acid construct described above is utilized in the cell-based and cell-free screening assays to identify or validate compounds that produce a stabilized SMNΔEx7 protein. Techniques for the production of an RNA transcript (e.g., a pre-mRNA transcript or a mRNA transcript) from a nucleic acid construct are known to one of skill in the art. For example, a mRNA transcript can be produced in a run-off transcription of a linearized form of a nucleic acid construct described herein. In a specific embodiment, the nucleic acid constructs described herein comprise bacteriophage promoters (e.g., a T3, SP6 or T7 bacteriophage promoter) or any other suitable promoter that may be used together with the respective RNA polymerase derived from the corresponding bacteriophage. Techniques for performing run-off transcription are well-known in the art. In a specific embodiment, a mRNA transcript transcribed from a nucleic acid construct described above is utilized in the cell-based and cell-free screening assays to identify or validate compounds that cause ribosomal frameshifting.

In certain embodiments, a nucleic acid construct described herein is isolated. In some embodiments, an RNA transcript (e.g., a pre-mRNA or mRNA transcript) described herein is isolated.

Screening Assays

Cell-Based Assays

In one aspect, presented herein are methods for the identification of compounds that cause ribosomal frameshifting and, as such, may be used to produce a stabilized SMNΔEx7 protein. The stabilized SMNΔEx7 protein produced may be of therapeutic benefit in patients with SMA, thus the compounds identified in the assays described herein may have utility in the treatment of SMA.

In one aspect, presented herein is a method for the identification or validation of a compound that causes ribosomal frameshifting comprising: (a) contacting a compound with a host cell expressing a nucleic acid construct described herein; and (b) detecting the activity of a fusion protein expressed from the nucleic acid construct. A compound that causes ribosomal frameshifting will result in an increase in the activity of the fusion protein expressed by the host cell compared with (i) the activity of the fusion protein expressed by the host cell in the absence of the compound, (ii) the activity of the fusion protein expressed by the host cell in the presence of a negative control, and/or (iii) against a previously determined reference range for a negative control. In a specific embodiment, the increase in the activity of the fusion protein is a statistically significant increase. In contrast, a compound that does not cause ribosomal frameshifting will not increase or not statistically significantly increase the level of activity of the fusion protein expressed by the host cell compared to (i) the level of activity of the fusion protein expressed by the host cell in the absence of the compound, (ii) the level of activity of fusion protein expressed by the host cell in the presence of a negative control, and/or (iii) a previously determined reference range for a negative control.

In some embodiments, in addition to, or as an alternative to, detecting the activity of the fusion protein expressed from the nucleic acid construct, the amount of the fusion protein can be detected. In accordance with such embodiments, an increase in the amount of the fusion protein expressed by the host cell in the presence of the compound when compared to (i) a previously determined reference range for a negative control, (ii) the amount of the fusion protein expressed by the host cell in the absence of the compound in such an assay, and/or (iii) the amount of the fusion protein expressed by the host cell in the presence of a negative control in such an assay indicates that a particular compound that causes ribosomal frameshifting. In a specific embodiment, the increase in the amount of the fusion protein is a statistically significant increase. In contrast, a compound that does not cause ribosomal frameshifting will not increase or not statistically significantly increase the amount of the fusion protein expressed by the host cell compared to (i) the amount of the fusion protein expressed by the host cell in the absence of the compound, (ii) the amount of fusion protein expressed by the host cell in the presence of a negative control, and/or (iii) a previously determined reference range for a negative control.

In one embodiment, a method for identifying or validating a compound that causes ribosomal frameshifting comprises: (a) expressing in a host cell a nucleic acid construct described herein; (b) contacting said host cell with a compound; and (c) detecting the activity or amount of a fusion protein encoded by the nucleic acid construct, wherein a compound that causes ribosomal frameshifting is identified or validated if the activity or amount of the fusion protein expressed by the host cell in the presence of a compound is increased relative to a previously determined reference range for a negative control, or relative to the activity or amount of the fusion protein expressed by the host cell in the absence of said compound or the presence of a negative control (e.g., PBS or DMSO). In a specific embodiment, an increase in the activity or amount of the fusion protein is a statistically significant increase.

In certain embodiments, a nucleic acid construct described in Zhang, et al., 2001, *Gene Therapy,* 8:1532-1538 (e.g., the nucleic acid construct in FIG. 1 of Zhang, et al., 2001, *Gene Therapy* 8: 1532-1538) is used in accordance with a method for identifying or validating a compound that causes ribosomal frameshifting which is described herein. In other embodiments, a nucleic acid construct described in Zhang, et al., 2001, *Gene Therapy,* 8:1532-1538 is not used in accordance with a method for identifying or validating a compound that causes ribosomal frameshifting which is described herein.

In another aspect, presented herein is a method for identifying or validating a compound that causes ribosomal frameshifting comprising: (a) contacting a compound with a host cell engineered to contain a RNA transcript (e.g., a pre-mRNA or mRNA transcript) transcribed from a nucleic acid construct described herein; and (b) detecting the activity or amount of a fusion protein translated from the pre-mRNA or mRNA transcript, wherein a compound that causes ribosomal frameshifting is identified or validated if the activity or amount of the fusion protein expressed by the host cell in the presence of a compound is increased relative to a previously determined reference range for a negative control, or relative to the activity or amount of the fusion protein expressed by the host cell in the absence of said compound or the presence of a negative control (e.g., PBS or DMSO). In a specific embodiment, an increase in the activity or amount of the fusion protein is a statistically significant increase.

In one embodiment, a method for identifying or validating a compound that causes ribosomal frameshifting comprises: (a) transfecting into a cell a RNA transcript (e.g., pre-mRNA or mRNA transcript) transcribed from a nucleic acid construct described herein; (b) contacting said host cell with a compound; and (c) detecting the activity or amount of a fusion protein translated from the RNA transcript, wherein a compound that causes ribosomal frameshifting is identified or validated if the activity or amount of the fusion protein expressed by the host cell in the presence of a compound is increased relative to a previously determined reference range for a negative control, or relative to the activity or amount of the fusion protein expressed by the host cell in the absence of said compound or the presence of a negative control (e.g., PBS or DMSO). In a specific embodiment, an increase in the activity or amount of the fusion protein is a statistically significant increase.

In certain embodiments, a RNA transcript (e.g., pre-mRNA or mRNA transcript) transcribed from a nucleic acid construct described in Zhang, et al., 2001, *Gene Therapy,* 8:1532-1538 (e.g., the nucleic acid construct in FIG. 1 of Zhang, et al., 2001, *Gene Therapy* 8: 1532-1538) is used in accordance with a method for identifying or validating a compound that causes ribosomal frameshifting which is described herein. In other embodiments, a RNA transcript transcribed from a nucleic acid construct described in Zhang, et al., 2001, *Gene Therapy,* 8:1532-1538 is not used in accordance with a method for identifying or validating a compound that causes ribosomal frameshifting which is described herein.

In another aspect, presented herein is a method for the identification or validation of a compound that produces a stabilized SMNΔEx7 protein using a nucleic acid construct described herein.

In one embodiment, a method for identifying or validating a compound that produces a stabilized SMNΔEx7 protein comprises: (a) contacting a host cell expressing a nucleic acid construct described herein; and (b) detecting the activity or amount of a fusion protein encoded by the nucleic acid construct, wherein a compound that produces a stabilized SMN-ΔEx7 protein is identified or validated if the activity or amount of the fusion protein expressed by the host cell in the presence of a compound is increased relative to a previously determined reference range for a negative control, or relative to the activity or amount of the fusion protein expressed by the host cell in the absence of said compound or the presence of a negative control (e.g., PBS or DMSO). In a specific embodiment, an increase in the activity or amount of the fusion protein is a statistically significant increase.

In another embodiment, a method for identifying or validating a compound that produces a stabilized SMNΔEx7 protein comprises: (a) expressing in a host cell a nucleic acid construct described herein; (b) contacting said host cell with a compound; and (c) detecting the activity or amount of a fusion protein encoded by the nucleic acid construct, wherein a compound that produces a stabilized SMNΔEx7 protein is identified or validated if the activity or amount of the fusion protein expressed by the host cell in the presence of a compound is increased relative to a previously determined reference range for a negative control, or relative to the activity or amount of the fusion protein expressed by the host cell in the absence of said compound or the presence of a negative control (e.g., PBS or DMSO). In a specific embodiment, an increase in the activity or amount of the fusion protein is a statistically significant increase.

In certain embodiments, a nucleic acid construct described in Zhang, et al., 2001, *Gene Therapy,* 8:1532-1538 (e.g., the nucleic acid construct in FIG. 1 of Zhang, et al., 2001, *Gene Therapy* 8: 1532-1538) is used in accordance with a method for identifying or validating a compound that produces a stabilized SMNΔEx7 protein which is described herein. In other embodiments, a nucleic acid construct described in Zhang, et al., 2001, *Gene Therapy,* 8:1532-1538 (e.g., the nucleic acid construct in FIG. 1 of Zhang, et al., 2001, *Gene Therapy* 8: 1532-1538) is not used in accordance with a method for identifying or validating a compound that produces a stabilized SMNΔEx7 protein which is described herein.

In another aspect, presented herein is a method for identifying or validating a compound that produces a stabilized SMNΔEx7 protein comprising: (a) contacting a compound with a host cell engineered to contain a RNA transcript (e.g., a pre-mRNA or mRNA transcript) transcribed from a nucleic acid construct described herein; and (b) detecting the activity or amount of a fusion protein translated from the pre-mRNA or mRNA transcript, wherein a compound that produces a stabilized SMNΔEx7 protein is identified or validated if the activity or amount of the fusion protein expressed by the host cell in the presence of a compound is increased relative to a previously determined reference range for a negative control, or relative to the activity or amount of the fusion protein expressed by the host cell in the absence of said compound or the presence of a negative control (e.g., PBS or DMSO). In a specific embodiment, an increase in the activity or amount of the fusion protein is a statistically significant increase.

In another aspect, presented herein is a method for identifying or validating a compound that produces a stabilized SMNΔEx7 protein comprising: (a) transfecting a host cell with a RNA transcript (e.g., a mRNA or pre-mRNA transcript) transcribed from a nucleic acid construct described herein; and (b) detecting the activity or amount of a fusion protein translated from the pre-mRNA or mRNA transcript, wherein a compound that produces a stabilized SMNΔEx7 protein is identified or validated if the activity or amount of the fusion protein expressed by the host cell in the presence of a compound is increased relative to a previously determined reference range for a negative control, or relative to the activity or amount of the fusion protein expressed by the host cell in the absence of said compound or the presence of a negative control (e.g., PBS or DMSO). In a specific embodiment, an increase in the activity or amount of the fusion protein is a statistically significant increase.

In certain embodiments, a RNA transcript (e.g., pre-mRNA or mRNA transcript) transcribed from a nucleic acid construct described in Zhang, et al., 2001, *Gene Therapy,* 8:1532-1538 (e.g., the nucleic acid construct in FIG. 1 of Zhang, et al., 2001, *Gene Therapy* 8: 1532-1538) is used in accordance with a method for identifying or validating a compound that produces a stabilized SMNΔEx7 protein, which is described herein. In other embodiments, a RNA transcript (e.g., pre-mRNA or mRNA transcript) transcribed from a nucleic acid construct described in Zhang, et al., 2001, *Gene Therapy,* 8:1532-1538 (e.g., the nucleic acid construct in FIG. 1 of Zhang, et al., 2001, *Gene Therapy* 8: 1532-1538) is not used in accordance with a method for identifying or validating a compound that produces a stabilized SMNΔEx7 protein, which is described herein.

The step of contacting a compound with a host cell containing the nucleic acid construct or RNA transcript may be conducted under conditions approximating or mimicking physiologic conditions. In a specific embodiment, a compound is added to the cells in the presence of an appropriate growth medium for said cells. In another embodiment, a compound is added to the cells in the presence of an aqueous solution. In accordance with this embodiment, the aqueous solution may comprise a buffer and a combination of salts, preferably approximating or mimicking physiologic conditions. Alternatively, the aqueous solution may comprise a buffer, a combination of salts, and a detergent or a surfactant. Examples of salts which may be used in the aqueous solution include, but are not limited to, KCl, NaCl, and/or $MgCl_2$. The optimal concentration of each salt used in the aqueous solution is dependent on the host cells and compounds used and can be determined using routine experimentation.

In a specific embodiment, a compound is contacted with a host cell containing the nucleic acid construct or RNA transcript for a specific period of time. For example, the compound may be contacted with the host cell containing the nucleic acid construct or RNA transcript for a time period of about 1 minute, 2 minutes, 3 minutes, 4, minutes, 5, minutes, 10 minutes, 15 minutes, 20 minutes, 30 minutes, 1 hour, 2 hours, 3 hours, 4 hours, 5 hours, 10 hours, 15 hours, 20 hours, 1 day, 2 days, 3 days, 4 days, 5 days, or 1 week. In a specific embodiment, contact is over a time period of about 12 hours to 15 hours, i.e., overnight.

In specific embodiments, a negative control (e.g., DMSO at 0.005-1.0%, or PBS, or another agent that is known to have no effect on the expression of the fusion protein) and a positive control (e.g., an agent that compound that causes ribosomal frameshifting, and thus, produces a stabilized SMNΔEx7 protein) are included in the cell-based assays described herein.

The amount or activity of a fusion protein described herein may be detected by any technique well-known to one of skill in the art. For example, techniques well-known to one of skill in the art for detecting reporter proteins can be used to detect either or both the amount or activity of fusion proteins. Methods for detecting the amount or activity of a reporter protein will vary with the reporter gene used. Assays for the various reporter genes are well-known to one of skill in the art.

Cell-Free Assays

In one aspect, presented herein are methods for the identification of compounds that cause ribosomal frameshifting and, as such, may be used to produce a stabilized SMNΔEx7 protein. The stabilized SMNΔEx7 protein produced may be of therapeutic benefit in patients with SMA, thus the compounds identified in the assays described herein may have utility in the treatment of SMA.

In one aspect, presented herein is a method for identifying or validating a compound that causes ribosomal frameshifting comprising: (a) contacting a compound with a composition comprising a cell-free extract and a RNA transcript (e.g., mRNA or pre-mRNA) which is transcribed from a nucleic acid construct described herein; and (b) detecting the amount or activity of a fusion protein translated from the RNA, wherein a compound that causes ribosomal frameshifting is identified or validated if the amount or activity of the fusion protein detected in the presence of the compound is increased relative to the amount or activity of the fusion protein detected in the absence of the compound or presence of a negative control (e.g., DMSO, PBS and the like), or relative to a previously determined reference range that is the amount or activity of the fusion protein obtained for a negative control. In a specific embodiment, the increase in the activity or amount of the fusion protein is a statistically significant increase. Typically, the RNA transcript (e.g., mRNA or pre-mRNA) used in the cell-free assay is one that has been produced using, e.g., in vitro run-off transcription. For example, a RNA can be made in run-off transcription of a linearized form of a nucleic acid construct described herein. Bacteriophage promoters from a T3, SP6 or T7 bacteriophage or any other suitable promoter may be used together with the respective RNA polymerase derived from the corresponding bacteriophage.

In certain embodiments, the RNA transcript used in accordance with a method for identifying or validating a compound that causes ribosomal frameshifting is transcribed from a nucleic acid construct described in Zhang, et al., 2001, *Gene Therapy,* 8:1532-1538 (e.g., the nucleic acid construct in FIG. 1 of Zhang, et al., 2001, *Gene Therapy,* 8:1532-1538). In other embodiments, the RNA transcript used in accordance with a method for identifying or validating a compound that causes ribosomal frameshifting is not transcribed from a nucleic acid construct described in Zhang, et al., 2001, *Gene Therapy,* 8:1532-1538 (e.g., the nucleic acid construct in FIG. 1 of Zhang, et al., 2001, *Gene Therapy,* 8:1532-1538).

In another embodiment, presented herein is a method for identifying or validating a compound that causes ribosomal frameshifting comprising: (a) contacting a compound with a composition comprising a cell-free extract and a nucleic acid construct described herein; and (b) detecting the amount or activity of a fusion protein expressed from the nucleic acid construct, wherein a compound that causes ribosomal frameshifting is identified or validated if the amount or activity of the fusion protein detected in the presence of the compound is increased relative to the amount or activity of the fusion protein detected in the absence of the compound or presence of a negative control (e.g., DMSO, PBS and the like), or relative to a previously determined reference range that is the amount or activity of the fusion protein obtained for a negative control. In accordance with this embodiment, the cell-free extract used comprises components necessary for in vitro transcription, splicing, and translation. In a specific embodiment, the increase in the activity or amount of the fusion protein is a statistically significant increase.

In certain embodiments, a nucleic acid construct described in Zhang, et al., 2001, *Gene Therapy,* 8:1532-1538 (e.g., the nucleic acid construct in FIG. 1 of Zhang, et al., 2001, *Gene Therapy,* 8:1532-1538) is used in accordance with a method for identifying or validating a compound that causes ribosomal frameshifting. In other embodiments, a nucleic acid construct described in Zhang, et al., 2001, *Gene Therapy,* 8:1532-1538 (e.g., the nucleic acid construct in FIG. 1 of Zhang, et al., 2001, *Gene Therapy,* 8:1532-1538) is not used in accordance with a method for identifying or validating a compound that causes ribosomal frameshifting.

In another aspect, presented herein are methods for the identification or validation of a compound that produces a stabilized SMNΔEx7 protein using a nucleic acid construct described herein.

In one aspect, presented herein is a method for identifying or validating a compound that produces a stabilized SMNΔEx7 protein comprising: (a) contacting a compound with a composition comprising a cell-free extract and a RNA transcript (e.g., mRNA or pre-mRNA) which is transcribed from a nucleic acid construct described herein; and (b) detecting the amount or activity of a fusion protein translated from the RNA, wherein a compound that produces a stabilized SMNΔEx7 protein is identified or validated if the amount or activity of the fusion protein detected in the presence of the compound is increased relative to the amount or activity of the fusion protein detected in the absence of the compound or presence of a negative control (e.g., DMSO, PBS and the like), or relative to a previously determined reference range that is the amount or activity of the fusion protein obtained for a negative control. In a specific embodiment, the increase in the activity or amount of the fusion protein is a statistically significant increase. Typically, the RNA transcript (e.g., mRNA or pre-mRNA) used in the cell-free assay is one that has been produced using, e.g., in vitro run-off transcription. For example, a RNA can be made in run-off transcription of a linearized form of a nucleic acid construct described herein. Bacteriophage promoters from a T3, SP6 or T7 bacteriophage or any other suitable promoter may be used together with the respective RNA polymerase derived from the corresponding bacteriophage.

In certain embodiments, a RNA transcript (e.g., a pre-mRNA or mRNA transcript) which is transcribed from a nucleic acid construct described in Zhang, et al., 2001, *Gene Therapy,* 8:1532-1538 (e.g., the nucleic acid construct in FIG. 1 of Zhang, et al., 2001, *Gene Therapy,* 8:1532-1538) is used in accordance with a method for identifying or validating a compound that produces a stabilized SMNΔEx7 protein. In other embodiments, a nucleic acid construct described in Zhang, et al., 2001, *Gene Therapy,* 8:1532-1538 (e.g., the nucleic acid construct in FIG. 1 of Zhang, et al., 2001, *Gene Therapy,* 8:1532-1538) is not used in accordance with a method for identifying or validating a compound that produces a stabilized SMNΔEx7 protein.

In another embodiment, presented herein is a method for identifying or validating a compound that produces a stabilized SMNΔEx7 protein comprising: (a) contacting a compound with a composition comprising a cell-free extract and a nucleic acid construct described herein; and (b) detecting the amount or activity of the fusion protein expressed from the nucleic acid construct, wherein a compound that produces a stabilized SMNΔEx7 protein is identified or validated if the amount or activity of the fusion protein detected in the presence of the compound is increased relative to the amount or activity of the fusion protein detected in the absence of the compound or presence of a negative control (e.g., DMSO, PBS and the like), or relative to a previously determined reference range that is the amount or activity of the fusion protein obtained for a negative control. In accordance with this aspect, the cell-free extract used comprises components necessary for in vitro transcription, splicing, and translation. In a specific embodiment, the increase in the activity or amount of the fusion protein is a statistically significant increase.

In certain embodiments, a nucleic acid construct described in Zhang, et al., 2001, *Gene Therapy,* 8:1532-1538 (e.g., the nucleic acid construct in FIG. 1 of Zhang, et al., 2001, *Gene Therapy,* 8:1532-1538) is used in accordance with a method for identifying or validating a compound that produces a stabilized SMNΔEx7 protein.

In other embodiments, a nucleic acid construct described in Zhang, et al., 2001, *Gene Therapy,* 8:1532-1538 (e.g., the nucleic acid construct in FIG. 1 of Zhang, et al., 2001, *Gene Therapy,* 8:1532-1538) is not used in accordance with a method for identifying or validating a compound that produces a stabilized SMNΔEx7 protein.

The step of contacting a compound with a cell-free extract and a composition comprising a RNA transcript or a nucleic acid construct as described herein may be conducted under conditions approximating or mimicking physiologic conditions. In a specific embodiment, a compound is added to a composition comprising the cell-free extract and nucleic acid construct or RNA transcript in the presence of an aqueous solution. In accordance with this embodiment, the aqueous solution may comprise a buffer and a combination of salts, preferably approximating or mimicking physiologic conditions. Alternatively, the aqueous solution may comprise a buffer, a combination of salts, and a detergent or a surfactant. Examples of salts which may be used in the aqueous solution include, but not limited to, KCl, NaCl, and/or $MgCl_2$. The optimal concentration of each salt used in the aqueous solution is dependent on the cell-free extract and compounds used and can be determined using routine experimentation.

In a specific embodiment, a compound may be contacted with a composition comprising a cell-free extract and a RNA transcript or a nucleic acid construct for a specific period of time. For example, a compound may be contacted with a composition comprising a cell-free extract and a RNA transcript or a nucleic acid construct for a time period of about 2 minutes, 5 minutes, 10 minutes, 15 minutes, 20 minutes, 30 minutes, 45 minutes, 1 hour, 2 hours, 3 hours, 4 hours, 8 hours, 10 hours, 12 hours, 14 hours, 16 hours, 18 hours or 24 hours. In some embodiments, the compound is contacted with a composition comprising a cell-free containing a RNA transcript or a nucleic acid construct for a time period in a range of from about 1 minute to about 2 hours, from about 1 minute to about 1 hour, from about 1 minute to about 45 minutes, from about 1 minute to about 30 minutes, or from about 1 minute to about 15 minutes In specific embodiments, a negative control (e.g., DMSO at 0.005-1.0%, or PBS, or another agent that is known to have no effect on the expression of the fusion protein) and a positive control (e.g., an agent that compound that causes ribosomal frameshifting, and thus, produces a stabilized SMNΔEx7 protein) are included in the cell-free assays described herein.

Host Cells, Cell-Free Extracts, and Reporter Genes

Techniques for the production or use of the nucleic acid constructs, the production or use of RNA, and production of host cells and cell-free extracts will employ, unless otherwise indicated, routine conventional techniques of molecular biology, microbiology, and recombinant DNA manipulation and production.

In some embodiments, the nucleic acid constructs utilized in the assays above may comprise one or more regulatory elements. Any transcriptional regulatory element(s) known to those skilled in the art are intended to be included herein for use in controlling transcription of a nucleic acid construct. Non-limiting examples of the types of transcriptional regulatory element(s) include a constitutive promoter, a tissue-specific promoter or an inducible promoter. In a specific embodiment, the transcription of a nucleic acid construct is controlled, at least in part, by one or more mammalian (in some embodiments, human) transcriptional regulatory element(s). In a specific embodiment, the transcription of a nucleic acid construct is controlled, at least in part, by a strong promoter, such as CMV. The transcriptional regulatory elements may be operably linked to a nucleic acid construct.

The nucleic acid constructs described herein may be part of a vector. Such a vector may provide post-transcriptional regulatory elements. The vector chosen will depend upon a variety of factors, including, without limitation, the strength of the transcriptional regulatory elements and the host cell to be used to express a nucleic acid construct.

In a specific embodiment, the nucleic acid construct is a part of CMV vector, such as pcDNA™3.1/Hygro (Invitrogen Corp., Carlsbad, Calif.). In other embodiments, the nucleic acid construct is part of a T7 vector, a lac vector, a pCEP4 vector or a 5.0/FRT vector.

Any reporter gene well-known to one of skill in the art may be used in the nucleic acid constructs described herein to identify or validate whether a compound causes ribosomal frameshifting. Reporter genes refer to a nucleotide sequence encoding or coding for a protein that is readily detectable either by its presence or activity. In certain embodiments, the nucleotide sequence of the reporter gene includes exons and introns. In other embodiments, the nucleotide sequence of the reporter gene excludes introns. In specific embodiments, the reporter gene coding sequence is used. Reporter genes may be obtained and the nucleotide sequence of the reporter gene determined by any method well-known to one of skill in the art.

Examples of reporter genes include, but are not limited to, nucleotide sequences encoding or coding for luciferase (e.g., firefly luciferase, renilla luciferase, and click beetle luciferase), fluorescent protein (e.g., green fluorescent protein ("GFP"), yellow fluorescent protein, red fluorescent protein, cyan fluorescent protein, and blue fluorescent protein), beta-galactosidase ("β-gal"), beta-glucoronidase, beta-lactamase, chloramphenicol acetyltransferase ("CAT"), and alkaline phosphatase ("AP").

In a specific embodiment, a gene product of a reporter gene utilized in the nucleic acid constructs is easily detected and the activity of the gene product detected is not normally found in the cell or organism of interest. In a specific embodiment, a reporter gene utilized in the nucleic acid constructs is not, per se, SMN1 or SMN2.

Host cells containing a nucleic acid construct or RNA transcript (e.g., a pre-mRNA or RNA transcript) may be produced utilizing any technique known to one of skill in the art. For example, cells may be transformed or transfected with a nucleic acid construct described herein or a RNA transcript transcribed from a nucleic acid construct described herein. In one embodiment, the host cell is transiently transfected with the nucleic acid construct. In an alternative embodiment, the host cell is stably transfected with a nucleic acid construct. In certain embodiments, more than one nucleic acid construct may be transfected into a host cell.

In one specific embodiment, the host cell is a mammalian cell. In another specific embodiment, the host cell is a human cell. In another embodiment, the host cells are primary cells isolated from a tissue or other biological sample of interest. Host cells that can be used in the methods described herein include, but are not limited to, hybridomas, pre-B cells, HEK293 cells, HEK293T cells, HEK293H cells, HeLa cells, HepG2 cells, K562 cells, 3T3 cells, MCF7 cells, SkBr3 cells, COS cells, BT474 cells, the human type I SMA fibroblast cell line GMO3813 or neuroblastoma cells lines such as MC-IXC, SK-N-MC, SK-N-MC, SK-N-DZ, SH-SY5Y, and BE(2)-C. In one embodiment, the host cells are immortalized cell lines derived from a source, e.g., a tissue. In one embodiment, the host cells are stem cells.

Transformation may be by any known method for introducing polynucleotides into a host cell. The transformation procedure used depends upon the host to be transformed. Such methods are well-known to one of skill in the art.

Stable cell lines may be generated by introducing a nucleic acid construct further comprising a selectable marker, allowing the cells to grow for 1-2 days in an enriched medium, and then growing the cells on a selective medium. The selectable marker in the recombinant plasmid confers resistance to the selection and allows cells to stably integrate the plasmid into their chromosomes and grow to form foci which in turn can be cloned and expanded into cell lines.

Encompassed herein is the translation of a RNA transcript from a nucleic acid construct in a cell-free system. In a specific embodiment, a cell-free extract provides the components necessary for translation of a RNA transcript in vitro. Any technique well-known to one of skill in the art may be used to generate cell-free extracts for translation in vitro. For example, the cell-free extracts for in vitro translation reactions can be generated by centrifuging cells and clarifying the supernatant.

In some embodiments, a cell-free extract provides the components necessary for in vitro transcription of nucleic acid constructs and translation. In a specific embodiment, the cell-free extract utilized is the in vitro transcription and translation (TNT)-coupled reticulocyte lysate available from Promega. In certain embodiments, a cell-free extract provides the components necessary for in vitro transcription of nucleic acid constructs, splicing, and translation.

The cell-free extract may be isolated from cells of any species origin. For example, the cell-free extract may be isolated from human cells (e.g., HeLa cells, RD cells, A204 cells), HEK293 cells, Vero cells, yeast, mouse cells (e.g., cultured mouse cells), rat cells (e.g., cultured rat cells), Chinese hamster ovary (CHO) cells, *Xenopus* oocytes, rabbit reticulocytes, primary cells, cancer cells (e.g., undifferentiated cancer cells), cell lines, wheat germ, rye embryo, or bacterial cell extract. In a specific embodiment, the cells from which the cell-free extract is obtained do not endogenously express SMN or SMNΔEx7. In another embodiment, the cell-free extract is an extract isolated from human cells. In a further embodiment, the human cells that can be used in the methods described herein, include, but are not limited to HeLa cells, HEK293 cells, HEK293T cells, HEK293H cells, HeLa cells, HepG2 cells, K562 cells, 3T3 cells, MCF7 cells, SkBr3 cells, BT474 cells, MC-IXC cells, SK-N-MC cells, SK-N-MC cells, SK-N-DZ cells, SH-SY5Y cells, or BE(2)C.

Methods for Characterizing Compounds that Produce a Stabilized SMNΔEx7 Protein Biological Activity in Cell-Based Assays Compounds identified or validated in the assays described herein that produce a stabilized SMNΔEx7 protein may be further tested in in vitro assays well-known to one of skill in the art or described herein for the ability of said compounds to produce a stabilized SMNΔEx7 protein. In one example, a cell-based assay may be used, wherein a compound is contacted with a host cell that endogenously expresses the SMN2 gene and the activity or amount of SMN, naturally-occurring SMNΔEx7 protein, and/or a stabilized SMNΔEx7 protein produced is measured. The amount of SMN, naturally-occurring SMNΔEx7 protein, and/or a stabilized SMNΔEx7 protein can be measured by immunological methods, e.g., immunoprecipitation, Western blot analysis, ELISA, and flow cytometry. An increased level of stabilized SMNΔEx7 protein compared to naturally-occurring SMNΔEx7 protein in a host cell contacted with a compound indicates that the compound may be effective for use in treating SMA. Specific examples of cell culture models from patients with SMA include, but are not limited to, fibroblast, amniocyte, and chorionic villous sampling (CVS) cell cultures (see, e.g., Patrizi et al., 1999. *Eur J Hum Genet* 7:301-309).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., western blot analysis. One skilled in the art would be knowledgeable as to the parameters that can be modified to increase the binding of the antibody to an antigen and decrease the background (e.g., pre-clearing the cell lysate with sepharose beads).

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), incubating the membrane with primary antibody (the antibody of interest) diluted in blocking buffer, washing the membrane in washing buffer, incubating the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise.

ELISAs comprise preparing a solution of the antigen (for example, a cell lysate containing the antigen of interest or a buffered solution of a purified antigen of interest), coating the wells of a 96 well microtiter plate with the antigen, washing the wells with an inert buffer solution, adding an antigen-recognizing antibody conjugated to a reporter compound such as an enzymatic reporter (e.g., horseradish peroxidase or alkaline phosphatase) to the wells, incubating for a period of time, removing the excess conjugated antibody, washing the wells extensively with an inert buffer solution, and measuring the amount or the activity of retained reporter. In ELISAs, the antibody of interest does not have to be conjugated to a reporter compound; instead, a second antibody (which specifically binds the antigen-recognizing antibody) conjugated to a reporter compound may be added to the wells. Further, instead of coating the wells with the antigen, the antibody may be coated to the wells first. In this case, a second antibody conjugated to a reporter compound may be added following the addition of the antigen of interest to the coated wells. The antibody of interest does not have to be conjugated to a reporter compound; instead, a second antibody (which specifically binds the antigen-recognizing antibody) conjugated to a reporter compound may be added to the wells. One skilled in the art would be knowledgeable as to the experimental variables that can be modified to increase the signal detected as well as other variations of ELISAs known in the art.

The amount of SMN, naturally-occurring SMNΔEx7 protein, and/or a stabilized SMNΔEx7 protein also can be measured using an HTRF assay. HTRF assays comprise preparing a solution of the antigen (for example, a cell lysate containing the antigen of interest or a buffered solution of a purified antigen of interest) and adding two antigen-recognizing antibodies: a FRET donor antibody conjugated to a rare earth metal ion complexed in a cryptate complex and an acceptor antibody labeled with a FRET acceptor dye to the well, incubating for a period of time, and measuring the amount of fluorescence energy transfer. One skilled in the art would be knowledgeable as to the experimental variables that can be modified to increase the signal detected as well as other variations of HTRF assays known in the art.

Another antibody-based separation that can be used to detect naturally-occurring SMNΔEx7 protein and stabilized SMNΔEx7 protein encoded by the SMN2 gene is the use of flow cytometry such as by a florescence activated cell sorter ("FACS"). Cells are fixed, permeabilized and blocked with excess protein in FACS buffer. The suspended mixture of cells are centrifuged and resuspended in FACS buffer. Antibodies which are conjugated to fluorochrome are added to allow the binding of the antibodies to specific proteins. In some embodiments, secondary antibodies that are conjugated to fluorochromes can be used to detect primary antibodies specific to the protein of interest. The cell mixture is then washed by one or more centrifugation and resuspension steps. The mixture is run through a FACS which separates the cells based on different fluorescence characteristics. FACS systems are available in varying levels of performance and ability, including multi-color analysis. The intact cells can be identified by a characteristic profile of forward and side scatter which is influenced by size and granularity, as well as by levels of expression of proteins directly or indirectly bound by the fluorochrome-conjugated antibody.

The effect of a compound on the half-life of a protein can be measured by an assay known in the art, e.g., after inhibiting translation using a protein synthesis inhibitor such as described in FIG. 3 of Mattis et al., *Neuroscience Letters,* 442(1):54-8 (which is incorporated by reference in its entirety).

The effect of a compound can also be assayed by performing indirect immunofluorescence analysis of nuclear gem levels to determine the compound's ability to elevate stabilized SMNΔEx7 protein levels in a cell line such as SMA patient fibroblasts (see Wolstencroft et al., 2005 *Human Molecular Genetics* 14(9):1199-1210). In addition, a cell-based assay that measures neurite outgrowth, such as the Neurite Outgrowth Assay described by Mattis et al. (2008, *Neuroscience Letters* 442:54-58), may be used to assess the effect of a compound on the activity of SMN. Further, the ability of a compound to affect the activity of SMN can be determined by assays that determine snRNP assembly efficiency, since it has been demonstrated that SMN is required for snRNP assembly (see Yong et al., 2004. *Trends Cell Biol* 14:226-232). snRNP assembly can be assayed by any method known to one skilled in the art.

Animal Model-Based Screens

Compounds identified in the assays described herein can be tested for biological activity using animal models for SMA. Non-limiting examples include animals engineered to contain SMN coupled to a functional readout system, such as a transgenic mouse. Such animal model systems include, but are not limited to, rats, mice, chicken, cows, monkeys, pigs, dogs, rabbits, etc. In a specific embodiment, a compound is tested in a mouse model system.

The anti-SMA activity of a compound can be determined by administering the compound to an animal model and verifying that the compound is effective in reducing the severity of SMA in said animal model. Examples of animal models for SMA include, but are not limited to, SMA animal models described by Monani et al. (2000, *Human Molecular Genetics* 9(16)2451-2457) and Charlotte J. Sumner (2006, *NeuroRx* 3(2):235-245). In a specific embodiment, a mouse model expresses a human SMN1 and/or SMN2 gene.

Cytotoxicity Assays

Compounds that cause ribosomal frameshifting, and thus, produce a stabilized SMNΔEx7 protein may be tested for cytotoxicity in mammalian, preferably human, cell lines. In certain embodiments, cytotoxicity is assessed in one or more of the following cell lines: U937, a human monocyte cell line;

primary peripheral blood mononuclear cells (PBMC); Huh7, a human hepatoblastoma cell line; HEK293T and HEK293H, human embryonic kidney cell lines; and THP-1, monocytic cells; a HeLa cell line; fibroblasts or other cell types isolated from SMA patients; SMA patient-derived cell lines, e.g., the GM03813 cell line; and neuroblastoma cells lines, such as MC-IXC, SK-N-MC, SK-N-MC, SK-N-DZ, SH-SY5Y and BE(2)-C. In general, many assays known to one skilled in the art can be used to assess viability of cells or cell lines following exposure to a compound and, thus, determine the cytotoxicity of the compound.

The toxicity and/or efficacy of a compound that causes ribosomal frameshifting can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A compound identified or validated in accordance with the methods described herein that exhibits large therapeutic indices is preferred. While a compound identified or validated in accordance with the methods described herein that exhibits toxic side effects may be used, care should be taken to design a delivery system that targets such agents to the site of affected tissue in order to minimize potential damage to uninfected cells and, thereby, reduces side effects.

The data obtained from the cell culture assays and animal studies can be used in formulating a range of dosage of a compound identified or validated in accordance with the methods described herein for use in humans. The dosage of such agents lies preferably within a range of circulating concentrations that include the $ED_{50}$ with little or no toxicity. The dosage may vary within this range depending upon the dosage form employed and the route of administration utilized. For any agent used in the methods described herein, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography.

Physiological Assays in SMA Patients

The ability of a compound or composition comprising a compound to treat SMA can be assayed by assessing muscle strength, motor function, and pulmonary function in patients diagnosed with SMA. Muscle strength can be assessed by using any method known to those skilled in the art, including, but not limited to, use of a hand held dynamometer. Muscle testing can be performed to assess right and left hand grip, right and left knee extension, right and left knee flexion, and right and left elbow flexion. Motor function can be assessed by a patient's ability to lie down, roll, sit, crawl, kneel, stand, walk, run and jump. Pulmonary function tests can be performed on patients according to American Thoracic Society standards, and include, but are not limited to maximum inspiratory pressure, maximum expiratory pressure, cough pressure, forced vital capacity, forced expiratory volume in the first second, and measurement of lung volume.

Compositions

Any compound described herein may optionally be in the form of a composition comprising the compound and an optional carrier, excipient or diluent. Other embodiments provided herein include pharmaceutical compositions comprising an effective amount of a compound and a pharmaceutically acceptable carrier, excipient, or diluent. The pharmaceutical compositions are suitable for veterinary and/or human administration. The pharmaceutical compositions provided herein can be in any form that allows for the composition to be administered to a subject, and these pharmaceutical compositions may be formulated for the route of administration.

In a specific embodiment and in this context, the term "pharmaceutically acceptable carrier, excipient or diluent" means a carrier, excipient or diluent approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a specific carrier when the pharmaceutical composition is administered intravenously. Saline solutions and aqueous dextrose and glycerol solutions can also be employed as liquid carriers, particularly for injectable solutions.

Typical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents. Further provided herein are anhydrous pharmaceutical compositions and dosage forms comprising one or more compounds described herein. The compositions and single unit dosage forms can take the form of solutions, suspensions, emulsion, tablets, pills, capsules, powders, sustained-release formulations and the like.

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art.

Because of their ease of administration, tablets and capsules represent the most advantageous oral dosage unit forms, in which case solid excipients are employed. In general, pharmaceutical compositions and dosage forms are prepared by uniformly and intimately admixing the active ingredients with liquid carriers, finely divided solid carriers, or both, and then shaping the product into the desired presentation if necessary.

Examples of excipients that can be used in oral dosage forms provided herein include, but are not limited to, binders, fillers, disintegrants, and lubricants.

Therapeutic Methods

In one aspect, a compound identified or validated using an assay described herein may be used to produce a stabilized SMNΔEx7 protein. In one embodiment, a method for producing a stabilized SMNΔEx7 protein in a subject comprises administering to a subject in need thereof an effective amount of a compound identified or validated in accordance with the methods described herein or a pharmaceutical composition thereof.

In a specific embodiment, presented herein is a method for producing a stabilized SMNΔEx7 protein in a subject, comprising administering to a subject in need thereof an effective amount of a compound or pharmaceutical composition thereof, wherein the compound in vitro or in cells increases the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment consists of the first 23 nucleotides from the 5' end of exon 8 of SMN; and (vi) a reporter gene coding sequence lacking a start codon, wherein the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and the nucleic acid residues of exons 6, 7, and 8 are in frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN. In one embodiment, the stabilized SMNΔEx7 protein comprises the amino acid sequence of SEQ ID NO:2. In one embodiment, the stabilized SMNΔEx7 protein comprises the amino acid sequence of SEQ ID NO:3. In one embodiment, the stabilized SMNΔEx7 protein comprises the amino acid sequence of SEQ ID NO:4. In one embodiment, the stabilized SMNΔEx7 protein comprises the amino acid sequence of SEQ ID NO:5. In certain embodiments, the stabilized SMNΔEx7 protein comprises one, two or more, all, or a combination of any of amino acid sequences SEQ ID NO:1, SEQ ID NO:2, SEQ ID NO:3, or SEQ ID NO:4.

In certain embodiments, a compound identified or validated using an assay described herein has utility in treating SMA. In one embodiment, a method for treating SMA comprises administering to a subject in need thereof an effective amount of a compound identified or validated in accordance with the methods described herein or a pharmaceutical composition thereof. In a specific embodiment, presented herein is a method for treating SMA in a subject, comprising administering to a subject in need thereof an effective amount of a compound or pharmaceutical composition thereof, wherein the compound in vitro or in cells increases the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment consists of the first 23 nucleotides from the 5' end of exon 8 of SMN; and (vi) a reporter gene coding sequence lacking a start codon, wherein the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and the nucleic acid residues of exons 6, 7, and 8 are in frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN.

A compound or a composition thereof may be used in conjunction with another therapy (e.g., a palliative therapy) for SMA. In a specific embodiment, two or more compounds may be used to treat SMA. In specific embodiments, a compound or a composition thereof is the only active ingredient administered to treat SMA.

In some embodiments, a compound that is administered to a subject produces a stabilized SMNΔEx7 protein, and the stabilized SMNΔEx7 protein has 2%, 3%, 4%, 5%, 10%, 15%, 20%, 25%, 35%, 45%, 50%, 55%, 65%, 70%, 75%, 80%, 85%, 90%, 95%, 100%, 150%, 200%, 300%, 400%, 500% or greater half-life than the half-life of naturally-occurring SMNΔEx7 protein, as assessed by an assay known to one of skill in the art, e.g., Protein Degradation in Rabbit Reticulocyte Lysate Assay; a Pulse-Chase Analysis in Cultured Cell Assay; or by an assay described by Mattis et al. (*Neuroscience Letters,* 442(1):54-8).

In another embodiment, a compound that is administered to a subject produces a stabilized SMNΔEx7 protein, and the stabilized SMNΔEx7 protein has a 1.5, 2, 3, 4, or 5 fold or greater half-life than the half-life of naturally-occurring SMNΔEx7 protein, as assessed by an assay known to one of skill in the art, e.g., Protein Degradation in Rabbit Reticulocyte Lysate Assay; a Pulse-Chase Analysis in Cultured Cell Assay; or by an assay described by Mattis et al. (*Neuroscience Letters,* 442(1):54-8).

In some embodiments, a compound that is administered to a subject produces a stabilized SMNΔEx7 protein, and the stabilized SMNΔEx7 protein has 2%, 3%, 4%, 5%, 10%, 15%, 20%, 25%, 35%, 45%, 50%, 55%, 65%, 70%, 75%, 80%, 85%, 90%, 95%, 100%, 150%, 200%, 300%, 400%, 500% or greater abundance than the abundance of naturally-occurring SMNΔEx7 protein, as assessed by an assay known to one of skill in the art, e.g., immunoassay.

In another embodiment, a compound that is administered to a subject produces a stabilized SMNΔEx7 protein, and the stabilized SMNΔEx7 protein has a 1.5, 2, 3, 4, or 5 fold or greater abundance than the abundance of naturally-occurring SMNΔEx7 protein, as assessed by an assay known to one of skill in the art, e.g., immunoassay.

The effective amount of a compound to be used depends on a number of factors, including but not limited to the type of SMA, health and age of the patient, and toxicity or side effects. Encompassed herein are methods for treating SMA for which no treatment is available. Also encompassed are methods for treating SMA as an alternative to conventional therapies.

Presented herein are methods of treating SMA in a subject in need thereof, said methods comprising administering to the subject one or more of the compounds with one or more additional agents or other therapies. In one embodiment, one or more compounds are administered to the subject in combination with a supportive therapy, a pain relief therapy, or other therapy that does not have an effect per se on SMA.

One or more compounds may be administered to a subject to treat SMA in any order. In addition, one or more compounds and one or more other therapies may be administered in any order to a subject to treat SMA.

One or more compounds and one or more additional agents can be administered sequentially or concurrently. For example, one or more compounds may be administered to a subject in combination with an agent that increases the transcription of the SMN2 gene.

In a specific embodiment, the therapeutic effect of a compound may be improved by administering it in combination with an additional agent(s) by functioning together to have an additive or synergistic effect. In another embodiment, the therapeutic effect of a compound may be improved by administering it in combination with an additional agent(s) by reducing the side effects associated with each compound and agent when taken alone.

A compound(s) and an additional agent(s) can be administered to a subject in the same pharmaceutical composition as a combination product. Alternatively, a compound(s) and an additional agent(s) can be administered concurrently to a subject in separate pharmaceutical compositions. The compound(s) and an additional agent(s) may be administered to a subject by the same or different routes of administration.

Patient Population

In some embodiments, a compound or pharmaceutical composition thereof is administered to a subject suffering from SMA. In other embodiments, a compound or pharmaceutical composition thereof is administered to a subject predisposed or susceptible to SMA. In some embodiments, a compound or pharmaceutical composition thereof is administered to a subject with Type 0 SMA. In some embodiments, a compound or pharmaceutical composition thereof is administered to a subject with Type 1 SMA. In other embodiments, a compound or pharmaceutical composition thereof is administered to a subject with Type 2 SMA. In other embodiments, a compound or pharmaceutical composition thereof is administered to a subject with Type 3 SMA. In some embodiments, a compound or pharmaceutical composition thereof is administered to a subject with Type 4 SMA.

In certain embodiments, a compound or pharmaceutical composition thereof is administered to a human that has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In some embodiments, a compound or pharmaceutical composition thereof is administered to a human infant. In other embodiments, a compound or pharmaceutical composition thereof is administered to a human toddler. In other embodiments, a compound or pharmaceutical composition thereof is administered to a human child. In other embodiments, a compound or pharmaceutical composition thereof is administered to a human adult. In yet other embodiments, a compound or pharmaceutical composition thereof is administered to an elderly human.

In some embodiments, a compound or pharmaceutical composition thereof is administered to a patient to treat the onset of SMA in a patient at risk of developing SMA. In some embodiments, a compound or pharmaceutical composition thereof is administered to a patient who is susceptible to adverse reactions to conventional therapies. In some embodiments, a compound or pharmaceutical composition thereof is administered to a patient who has proven refractory to therapies other than compounds, but are no longer on these therapies. In certain embodiments, the patients being treated in accordance with the methods described herein are patients already being treated with antibiotics, anti-virals, anti-fungals, or other biological therapy/immunotherapy. Among these patients are refractory patients, and patients who are too young for conventional therapies.

In some embodiments, the subject being administered a compound or pharmaceutical composition thereof has not received therapy prior to the administration of the compound or pharmaceutical composition thereof.

Mode of Administration

When administered to a patient, a compound is preferably administered as a component of a composition that optionally comprises a pharmaceutically acceptable carrier, excipient or diluent. The composition can be administered orally, or by any other convenient route, for example, by infusion or bolus injection, by absorption through epithelial or mucocutaneous linings (e.g., oral mucosa, rectal, and intestinal mucosa) and may be administered together with another biologically active agent. Administration can be systemic or local. Various delivery systems are known, e.g., encapsulation in liposomes, microparticles, microcapsules, and capsules, and can be used to administer the compound.

Methods of administration include but are not limited to parenteral, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of a compound into the bloodstream. In a specific embodiment, a compound is administered orally.

Dosage and Frequency of Administration

The amount of a compound that will be effective in the treatment of SMA can be determined by standard clinical techniques. In vitro or in vivo assays may optionally be employed to help identify optimal dosage ranges. The precise dose and frequency of administration to be employed will also depend, e.g., on the route of administration, the type of SMA, and the seriousness of the SMA, and should be decided according to the judgment of the practitioner and each patient's or subject's circumstances.

Exemplary doses of a compound include milligram (mg) or microgram (μg) amounts per kilogram (Kg) of subject or sample weight per day (e.g., from about 1 μg per Kg to about 500 mg per Kg per day, from about 5 μg per Kg to about 100 mg per Kg per day, or from about 10 μg per Kg to about 100 mg per Kg per day. In specific embodiments, a daily dose is at least 0.1 mg, 0.5 mg, 1.0 mg, 2.0 mg, 5.0 mg, 10 mg, 25 mg, 50 mg, 75 mg, 100 mg, 150 mg, 250 mg, 500 mg, 750 mg, or at least 1 g. In another embodiment, the dosage is a unit dose of about 0.1 mg, 1 mg, 5 mg, 10 mg, 50 mg, 100 mg, 150 mg, 200 mg, 250 mg, 300 mg, 350 mg, 400 mg, 500 mg, 550 mg, 600 mg, 650 mg, 700 mg, 750 mg, 800 mg or more. In another embodiment, the dosage is a unit dose that ranges from about 0.1 mg to about 1000 mg, 1 mg to about 1000 mg, 5 mg to about 1000 mg, about 10 mg to about 500 mg, about 150 mg to about 500 mg, about 150 mg to about 1000 mg, 250 mg to about 1000 mg, about 300 mg to about 1000 mg, or about 500 mg to about 1000 mg. In another embodiment, a subject is administered one or more doses of an effective amount of a compound or a composition, wherein the effective amount is not the same for each dose.

Combination Products

Additional agents that can be used in combination with compounds described herein or identified using the methods presented herein or in a combination product for the treatment of SMA include, but are not limited to, small molecules, synthetic drugs, peptides (including cyclic peptides), polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules. Specific examples of such agents include, but are not limited to, immunomodulatory agents (e.g., interferon), anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steriods, and non-steriodal anti-inflammatory drugs (e.g., aspirin, ibuprofen, diclofenac, and COX-2 inhibitors), pain relievers, leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), antiviral agents (e.g., nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, and AZT) and antibiotics (e.g., dactinomycin (formerly actinomycin), bleomycin, erythomycin, penicillin, mithramycin, and anthramycin (AMC)).

Any therapy which is known to be useful, or which has been used, will be used or is currently being used for the treatment of SMA can be used in combination with compounds described herein or identified using the methods presented herein. Therapeutics that can be used in combination with compounds include, but are not limited to riluzole, gabapentin, phenylbutyrate, hydroroxyurea, L aetyl carnitine, indoprofen, aminoglycosides, cardiotrophin 1, and histone deacetylase (HDAC) inhibitors such as, sodium butyrate, phenylybutyrate, valproic acid, suberoyl anilide hydrorxamic acid (see, e.g., Charlotte J. Sumner, 2006. NeuroRx, 3(2): 235-245). In certain embodiments, therapeutics that can be used in combination with compounds include, but are not limited to, a chemotherapeutic and sodium vandate. In certain embodiments, the therapeutics that can be used in combination with compounds include aclarubicin.

Antibodies

Antibody Characteristics

Encompassed herein are antibodies that specifically bind to a stabilized SMNΔEx7 protein.

In one embodiment, the antibodies specifically bind with about a 5%, 10%, 15%, 20%, 25%, 35%, 45%, 50%, 55%, 65%, 70%, 75%, 80%, 85%, 90%, 95%, 100%, 150%, 200%, 300%, 400%, 500% or greater $K_a$ to a stabilized SMNΔEx7 protein than to naturally-occurring SMNΔEx7 protein under comparable assay conditions. In another embodiment, the antibodies specifically bind with about a 1.5, 2, 3, 4, or 5 fold or greater $K_a$ to a stabilized SMNΔEx7 protein than to naturally-occurring SMNΔEx7 protein under comparable assay conditions.

In another embodiment, the antibodies specifically bind with about a 5%, 10%, 15%, 20%, 25%, 35%, 45%, 50%, 55%, 65%, 70%, 75%, 80%, 85%, 90%, 95%, 100%, 150%, 200%, 300%, 400%, 500% or lower $K_D$ to a stabilized SMNΔEx7 protein than to naturally-occurring SMNΔEx7 protein under comparable assay conditions. In another embodiment, the antibodies specifically bind with about a 1.5, 2, 3, 4, or 5 fold or lower $K_D$ to a stabilized SMNΔEx7 protein than to naturally-occurring SMNΔEx7 protein under comparable assay conditions.

In one embodiment, the antibodies specifically bind with about a 5% to 25%, 5% to 50%, 5% to 75%, 5% to 100%, 5% to 150%, 5% to 200%, 5% to 300%, 5% to 400%, or 5% to 500% greater $K_a$ to a stabilized SMNΔEx7 protein than to naturally-occurring SMNΔEx7 protein under comparable assay conditions. In another embodiment, the antibodies specifically bind with about a 1.5 to 2, 1.5 to 3, 1.5 to 4, or 1.5 to 5 fold greater $K_a$ to a stabilized SMNΔEx7 protein than to naturally-occurring SMNΔEx7 protein under comparable assay conditions.

In another embodiment, the antibodies specifically bind with about a 5% to 25%, 5% to 50%, 5% to 75%, 5% to 100%, 5% to 150%, 5% to 200%, 5% to 300%, 5% to 400%, or 5% to 500% lower $K_D$ to a stabilized SMNΔEx7 protein than to naturally-occurring SMNΔEx7 protein under comparable assay conditions. In another embodiment, the antibodies specifically bind with about a 1.5 to 2, 1.5 to 3, 1.5 to 4, or 1.5 to 5 fold lower $K_D$ to a stabilized SMNΔEx7 protein than to naturally-occurring SMNΔEx7 protein under comparable assay conditions.

In a specific embodiment, the antibodies specifically bind to SEQ ID NO:2, SEQ ID NO:3, SEQ ID NO:4, or SEQ ID NO:5 with a higher Ka or a lower $K_D$ than to naturally-occurring SMNΔEx7 protein under comparable assay conditions. See, e.g., Blake, et al., *Analytical Biochem.,* 1999, 272:123-134, for a discussion regarding antibody specificity.

In one embodiment, the antibodies specifically bind with about a 5%, 10%, 15%, 20%, 25%, 35%, 45%, 50%, 55%, 65%, 70%, 75%, 80%, 85%, 90%, 95%, 100%, 150%, 200%, 300%, 400%, 500% or greater $K_a$ to a SEQ ID NO:2, SEQ ID NO:3, SEQ ID NO:4, or SEQ ID NO:5 than to naturally-occurring SMNΔEx7 protein under comparable assay conditions. In another embodiment, the antibodies specifically bind with about a 1.5, 2, 3, 4, or 5 fold or greater $K_a$ to SEQ ID NO:2, SEQ ID NO:3, SEQ ID NO:4, or SEQ ID NO:5 than to naturally-occurring SMNΔEx7 protein under comparable assay conditions.

In another embodiment, the antibodies specifically bind with about a 5%, 10%, 15%, 20%, 25%, 35%, 45%, 50%, 55%, 65%, 70%, 75%, 80%, 85%, 90%, 95%, 100%, 150%, 200%, 300%, 400%, 500% or lower $K_D$ to SEQ ID NO:2, SEQ ID NO:3, SEQ ID NO:4, or SEQ ID NO:5 than to naturally-occurring SMNΔEx7 protein under comparable assay conditions. In another embodiment, the antibodies specifically bind with about a 1.5, 2, 3, 4, or 5 fold or lower $K_D$ to SEQ ID NO:2, SEQ ID NO:3, SEQ ID NO:4, or SEQ ID NO:5 than to naturally-occurring SMNΔEx7 protein under comparable assay conditions.

In one embodiment, the antibodies specifically bind with about a 5%, 10%, 15%, 20%, 25%, 35%, 45%, 50%, 55%, 65%, 70%, 75%, 80%, 85%, 90%, 95%, 100%, 150%, 200%, 300%, 400%, 500% or greater $K_a$ to a stabilized SMNΔEx7 protein than to naturally-occurring SMNΔEx7 protein under comparable assay conditions as measured by surface plasmon resonance (e.g., Biacore®). In another embodiment, the antibodies specifically bind with about a 1.5, 2, 3, 4, or 5 fold or greater $K_a$ to a stabilized SMNΔEx7 protein than to naturally-occurring SMNΔEx7 protein under comparable assay conditions as measured by surface plasmon resonance (e.g., Biacore®).

In another embodiment, the antibodies specifically bind with about a 5%, 10%, 15%, 20%, 25%, 35%, 45%, 50%, 55%, 65%, 70%, 75%, 80%, 85%, 90%, 95%, 100%, 150%, 200%, 300%, 400%, 500% or lower $K_D$ to a stabilized SMNΔEx7 protein than to naturally-occurring SMNΔEx7 protein under comparable assay conditions as measured by surface plasmon resonance (e.g., Biacore®). In another embodiment, the antibodies specifically bind with about a 1.5, 2, 3, 4, or 5 fold or lower $K_D$ to a stabilized SMNΔEx7 protein than to naturally-occurring SMNΔEx7 protein under comparable assay conditions as measured by surface plasmon resonance (e.g., Biacore®).

In a specific embodiment, the antibodies specifically bind to SEQ ID NO:2, SEQ ID NO:3, SEQ ID NO:4, or SEQ ID NO:5 with a higher $K_a$ and/or a lower $K_D$ than to naturally-occurring SMNΔEx7 protein under comparable assay conditions as measured by surface plasmon resonance (e.g., Biacore®).

Encompassed herein are compositions comprising antibodies that specifically bind to a stabilized SMNΔEx7 protein. In a specific embodiment, the compositions comprise an antibody that specifically binds to a stabilized SMNΔEx7 protein and a pharmaceutically acceptable diluent, carrier, and/or excipient. The compositions encompassed herein are de signed to be appropriate for the selected mode of use, and pharmaceutically acceptable diluents, carrier, and/or excipients such as dispersing agents, buffers, surfactants, preservatives, solubilizing agents, isotonicity agents, stabilizing agents and the like are used as appropriate. In a specific embodiment, the compositions comprise antibodies that specifically bind to SEQ ID NO:2, SEQ ID NO:3, SEQ ID NO:4, or SEQ ID NO:5 with a higher $K_a$ and/or a lower $K_D$ than to naturally-occurring SMNΔEx7 protein under comparable assay conditions.

In one embodiment, the antibodies that specifically bind to a stabilized SMNΔEx7 protein are purified. As used herein, the term "purified antibody" refers to an antibody that has undergone any process which removes some contaminant from the antibody, such as a protein or nucleic acid. Antibodies can be purified according to standard procedures known in the art, including ammonium sulfate precipitation, ion exchange, affinity, reverse phase, hydrophobic interaction column chromatography, gel electrophoresis and the like.

In one embodiment, the antibodies that specifically bind to a stabilized SMNΔEx7 protein are isolated. As used herein, the term "isolated antibody" refers to an antibody that has been removed from its native environment. Isolation may include removing the antibody from a subject with or without SMA (e.g., from serum, blood, or other tissue) or removing the antibody from tissue/cell culture fluid.

Methods of Producing Antibodies

Antibodies that specifically bind to a stabilized SMNΔEx7 protein can be produced by any method known in the art for the synthesis of antibodies, in particular, by chemical synthesis or preferably, by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Ausubel et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) (1999) *Genome Analysis: A Laboratory Manual*, Cold Spring Harbor Laboratory Press.

Polyclonal antibodies that specifically bind to an antigen can be produced by various procedures well-known in the art. For example, a human antigen can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants also are well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas* 563 681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Antibody fragments may be generated by any technique known to those of skill in the art. For example, Fab and $F(ab')_2$ fragments may be produced by proteolytic cleavage of immunoglobulin molecules, using enzymes such as papain (to produce Fab fragments) or pepsin (to produce $F(ab')_2$ fragments). $F(ab')_2$ fragments contain the variable region, the light chain constant region and the CH1 domain of the heavy chain.

Further, the antibodies can also be generated using various phage display methods known in the art. Examples of phage display methods that can be used to make the antibodies described herein include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187: 9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

For some uses, it may be preferable to use human or chimeric antibodies. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For a discussion of technology for producing human antibodies and human monoclonal antibodies and protocols for producing such antibodies, see, e.g., PCT publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

A chimeric antibody is a molecule in which different portions of the antibody are derived from different immunoglobulin molecules. Methods for producing chimeric antibodies are known in the art. See, e.g., Morrison, 1985, Science 229: 1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415, which are incorporated herein by reference in their entirety.

Humanized antibodies can be produced using variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. No. 6,407,213, U.S. Pat. No. 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16): 10678-84 (1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), which is incorporated by reference herein in its entirety.

Single domain antibodies, for example, antibodies lacking the light chains, can be produced by methods well-known in the art. See Riechmann et al., 1999, J. Immunol. 231:25-38; Nuttall et al, 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301, each of which is incorporated herein by reference in its entirety.

Further, the antibodies that specifically bind to a stabilized SMNΔEx7 protein can, in turn, be utilized to generate anti-idiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8):2429-2438).

Generation of intrabodies is well-known to the skilled artisan and is described, for example, in U.S. Pat. Nos. 6,004,940; 6,072,036; 5,965,371, which are incorporated by reference in their entireties herein. Further, the construction of intrabodies is discussed in Ohage and Steipe, 1999, J. Mol. Biol. 291:1119-1128; Ohage et al., 1999, J. Mol. Biol. 291: 1129-1134; and Wirtz and Steipe, 1999, Protein Science 8:2245-2250, which references are incorporated herein by reference in their entireties. Recombinant molecular biological techniques such as those described for recombinant production of antibodies may also be used in the generation of intrabodies.

Polynucleotides Encoding an Antibody

Encompassed herein are polynucleotides comprising a nucleotide sequence encoding an antibody (modified or unmodified) that specifically binds to a stabilized SMNΔEx7 protein. The polynucleotides may be obtained, and the nucleotide sequence of the polynucleotides determined, by any method known in the art. Such a polynucleotide encoding an antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, fragments, or variants thereof, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Recombinant Expression of an Antibody

Recombinant expression of an antibody that specifically binds to a stabilized SMNΔEx7 protein requires construction of an expression vector containing a polynucleotide that encodes the antibody. Once a polynucleotide encoding an antibody molecule, heavy or light chain of an antibody, or fragment thereof (preferably, but not necessarily, containing the heavy and/or light chain variable domain) has been obtained, the vector for the production of the antibody molecule may be produced by recombinant DNA technology using techniques well-known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination.

The expression vector is transferred to a host cell by conventional techniques and the transfected cells are then cultured by conventional techniques to produce an antibody.

A variety of host-expression vector systems may be utilized to express the antibody (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody in situ.

For long-term, high-yield production of recombinant proteins, stable expression is preferred. For example, cell lines which stably express the antibody may be engineered.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention may be fused to heterologous polypeptide sequences described herein or otherwise known in the art to facilitate purification.

Antibody Conjugates and Fusion Proteins

In some embodiments, antibodies are conjugated or recombinantly fused to a diagnostic or detectable agent. The conjugated or recombinantly fused antibodies can be useful, e.g., for detecting stabilized SMNΔEx7 proteins. Such detection can be accomplished by coupling the antibody to detectable agents including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; and radioactive materials, such as, but not limited to, iodine ($^{131}I$, $^{125}I$, $^{123}I$, and $^{121}I$), carbon ($^{14}C$), sulfur ($^{35}S$), tritium ($^{3}H$), indium ($^{115}In$, $^{113}In$, $^{112}In$, and $^{111}In$), technetium ($^{99}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, $^{97}Ru$, $^{68}Ge$, $^{57}Co$, $^{65}Zn$, $^{85}Sr$, $^{32}P$, $^{153}Gd$, $^{169}Yb$, $^{51}Cr$, $^{54}Mn$, $^{75}Se$, $^{113}Sn$, and $^{117}Sn$. Techniques for coupling antibodies to detectable agents are known in the art.

Moreover, antibodies can be fused to marker sequences, such as a peptide to facilitate purification. In preferred embodiments, the marker amino acid sequence is a hexahistidine peptide, such as the tag provided in a pQE vector (QIAGEN, Inc.), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

Antibodies may also be attached to solid supports, which are particularly useful for immunoassays or purification of the target antigen (i.e., a stabilized SMNΔEx7 protein). Such solid supports include, but are not limited to, glass, cellulose, polyacrylamide, nylon, polystyrene, polyvinyl chloride or polypropylene.

Diagnostic Uses of Antibodies

Antibodies which specifically bind to a stabilized SMNΔEx7 protein can be used for diagnostic purposes to detect or monitor a stabilized SMNΔEx7 protein. In a specific embodiment, methods for the detection of stabilized SMNΔEx7 proteins comprise: (a) assaying the expression of a stabilized SMNΔEx7 protein in cells or a tissue sample using one or more antibodies that specifically bind to the stabilized SMNΔEx7 protein; and (b) comparing the level of the stabilized SMNΔEx7 protein with a control level, e.g., levels of stabilized SMNΔEx7 protein in untreated tissue/cell samples. The cell and/or tissue samples assayed may be from a patient treated with a compound, an isolated cell(s) or tissue sample treated with a compound, a cell(s) engineered to express a stabilized SMNΔEx7 protein, or cells with a mutation in SMN1. In a specific embodiment, the cell(s) or tissue samples are blood samples or fibroblasts.

In one embodiment, an assay for determining whether a compound is effective for treating SMA comprises: (a) assaying for the level of a stabilized SMNΔEx7 protein in cells or a tissue sample of an individual with SMA using one or more antibodies that specifically bind to a stabilized SMNΔEx7 protein; and (b) comparing the level of the stabilized SMNΔEx7 protein with a control level, e.g., levels of stabilized SMNΔEx7 protein in cells or a tissue sample of said individual with SMA prior to initiation of treatment with said compound.

Antibodies can be used to assay stabilized SMNΔEx7 protein levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105: 3087-3096). Other antibody-based methods useful for detecting protein gene expression include immunoassays, such as the enzyme linked immunosorbent assay (ELISA) and the radioimmunoassay (RIA). In these detection assays, the primary antibody that specifically binds to a stabilized SMNΔEx7 protein or a secondary antibody that binds to the primary antibody, is labeled. Suitable antibody assay labels are known in the art and include enzyme labels, such as, glucose oxidase; radioisotopes, such as iodine ($^{125}I$, $^{121}I$), carbon ($^{14}C$), sulfur ($^{35}S$), tritium ($^{3}H$), indium ($^{121}In$), and technetium ($^{99}Tc$); luminescent labels, such as luminol; and fluorescent labels, such as fluorescein and rhodamine, and biotin.

Kits

Described herein are kits comprising a nucleic acid construct described herein, in one or more containers, and instructions for use. In some embodiments, a kit further comprises a positive and/or negative control nucleic acid construct.

In some embodiments, a kit further comprises a positive and/or negative control agent. For example, in one embodiment, the negative control agent is DMSO or PBS. In another embodiment, the positive control is a compound of Formula (I) or a form thereof. In another embodiment, the positive control is a compound of Formula (II) or a form thereof. In another embodiment, the positive control is a compound of Formula (Ia) or a form thereof. In another embodiment, the positive control is a compound of Formula (IIa) or a form thereof.

In some embodiments, a kit further comprises components for in vitro transcription. In some embodiments, a kit further comprises a cell-free extract.

In another embodiment, a kit comprises an antibody, preferably a purified antibody, in one or more containers. In a specific embodiment, the kits contain a naturally-occurring SMNΔEx7 protein or fragment thereof as a control. In another specific embodiment, the kits comprise a control antibody which does not react with a stabilized SMNΔEx7 protein. In another specific embodiment, the kits contain a means for detecting the binding of an antibody to a stabilized SMNΔEx7 protein (e.g., the antibody may be conjugated to a detectable agent such as a fluorescent compound, an enzymatic substrate, a radioactive compound or a luminescent compound, or a second antibody which recognizes the first antibody may be conjugated to a detectable agent). In specific embodiments, the kit may include a recombinantly produced or chemically synthesized stabilized SMNΔEx7 protein or fragment thereof comprising amino acids from the C-terminus of a stabilized SMNΔEx7 protein. The stabilized SMNΔEx7 protein or fragment comprising amino acids from the C-terminus of a stabilized SMNΔEx7 protein provided in the kit may also be attached to a solid support.

Systems

Presented herein are systems comprising a kit or a component(s) of the kits presented herein and a computer program product for use in conjunction with a computer system. In such systems, the computer program product can comprise a computer readable storage medium and a computer program mechanism embedded therein. The computer program mechanism may comprise instructions for evaluating the amount or activity of a fusion protein encoded by a nucleic acid construct described herein. The computer program mechanism may comprise instructions for evaluating the amount of stabilized SMNΔEx7 protein.

EXAMPLES

Cryptic Splice Site

This example demonstrates that a cryptic splice site is created when a guanine residue is inserted after nucleotide 48 of exon 7 of SMN in a minigene construct comprising in 5' to 3' order: (i) the nucleic acid residues of exon 6 of SMN, the nucleic acid residues of intron 6 of SMN, the nucleic acid residues of exon 7 of SMN, the nucleic acid residues of intron 7 of SMN, the first 23 nucleic acid residues of exon 8 of SMN; and (ii) a reporter gene coding sequence fused in frame to the nucleic acid residues of exon 8 of SMN, wherein the reporter gene does not have a start codon. As a result of the cryptic splice site, a deletion of the last seven nucleotides of exon 7 occurs and a frameshift in the open reading frame of the reporter gene is created.

Materials and Methods

Preparation of the Minigene Constructs

DNA corresponding to a region of the SMN2 gene starting from the 5' end of exon 6 (ATAATTCCCCC) (SEQ ID NO:7) and ending at nucleic acid residue 23 of exon 8 (CAGCAC) (SEQ ID NO:8) was amplified by PCR using the following primers:

```
Forward primer:
                                    (SEQ ID No.: 9)
5'-CGCGGATCCATAATTCCCCCACCACCTC-3'

Reverse primer:
                                    (SEQ ID NO: 10)
5'-CGCGGATCCGTGCTGCTCTATGCCAGCA-3'
```

The 5' end of each primer was designed to add a BamHI site at both the 5' end of exon 6 (GGATCC) (SEQ ID NO:11) and the 3' end, after the $23^{rd}$ nucleotide, of exon 8. Using the BamHI restriction sites, the PCR fragment was cloned into a derivative of the original pcDNA 3.1/Hygro vector which was modified as disclosed in United States Patent Publication US2005/0048549.

New UTRs were added to the modified vector using the HindIII site and the BamHI site comprising a 5'deg UTR: 5'-TAGCTTCTTACCCGTACTCCACCGTTG-GCAGCACGATCGCACGTCCCACGT GAACCATTGG-TAAACCCTG-3' (SEQ ID NO:12) was cloned into the modified pcDNA3.1/Hygro vector together with a start codon upstream of the BamHI site; and a 3'deg UTR: 5'-ATCGAAAGTACAGGACTAGCCTTC-CTAGCAACCGCGGGCTGGGAGTCTGAGA CAT-CACTCAAGATATATGCTCGGTAACGTAT-GCTCTAGCCATCTAACTATTCCCT ATGTCTTATAGGG-3' (SEQ ID NO:13) was cloned into the modified pcDNA3.1/Hygro vector with a stop codon using the NotI site and the XhoI site. In addition, a luciferase gene lacking its start codon was cloned into the vector using the BamHI and NotI sites.

The resulting minigene comprises, in 5' to 3' order: the 5'-deg UTR, the start codon, six additional nucleotides forming a BamHI site, the nucleic acid residues of exon 6, the nucleic acid residues of intron 6 of SMN2, the nucleic acid residues of exon 7 of SMN2, the nucleic acid residues of intron 7 of SMN2, and the first 23 nucleic acid residues of exon 8 of SMN2, an additional six nucleotides forming a BamHI site and the luciferase gene lacking the start codon.

A single guanine residue was inserted after nucleotide 48 of exon 7 of SMN2 by site-directed mutagenesis. The minigene construct produced is referred to as SMN2-G.

To generate the SMN1 version of the minigene, the sixth nucleotide of exon 7 (a thymine residue) was changed to cytosine by site directed mutagenesis. The resulting SMN1 minigene construct is referred to as SMN1-G.

Results

SMN1 and SMN2 transcripts derived from minigenes containing exon 6 through 8 and the intervening introns recapitulate the splicing of their endogenous pre-mRNAs (Lorson, et al., 1999, *Proc. Natl. Acad. Sci. U.S.A.* 96(11):6307-6311). An SMN2-alternative splicing reporter construct which contains exons 6 to 8 and the intervening introns followed by a luciferase reporter gene was generated. Salient features of this construct are the lack of the start codon in the luciferase gene, inactivation of the termination codon (in the open reading frame that encodes the SMN protein) of exon 7 by insertion of a guanine residue after nucleic acid 48 of exon 7 and addition of a start codon (ATG) immediately upstream of exon 6.

The luciferase reporter was designed to be out of frame if exon 7 of SMN2 is removed during splicing of the pre-mRNA. In addition, the 23 nucleic acids of exon 8 are read in a different frame in the absence of exon 7, resulting in a stop codon in exon 8 in the mature mRNA transcript. Thus, the protein translated from an RNA transcript lacking exon 7 will be a truncated SMN protein lacking the luciferase portion encoded by the minigene construct. In the presence of compounds that increase the inclusion of exon 7 of SMN2 into mRNA transcribed from the SMN2 gene, more transcripts containing exon 7 were expected to be produced. In view of the teaching in Zhang, et al., 2001, *Gene Therapy,* 8:1532-1538, the presence of the additional guanine residue after nucleic acid residue 48 of exon 7 of SMN2 was expected to cause the SMN2 sequences to be in frame with the luciferase coding region in the spliced mRNA transcript containing exon 7. Thus, the resulting protein expressed from this mRNA transcript was expected to be a truncated SMN-luciferase fusion protein.

The DNA sequence of the minigene from the SMN2-G construct is provided in FIG. 1.

An SMN1 version of the SMN2 minigene construct was also generated in which the sixth nucleotide (T) of exon 7 was mutated to C to maximize the likelihood of inclusion of exon 7 into the transcript. Similar to the SMN2 minigene construct, the SMN1 minigene construct had a single guanine (SMN1-G) residue inserted after nucleic residue 48 of exon 7. The SMN1-G construct was expected to produce a truncated SMN-luciferase fusion protein because the SMN1 transcript derived from the minigene was expected to contain exon 7 and the SMN1 sequence was expected to be in frame with the luciferase coding region due to the guanine residue insert after nucleotide 48 of exon 7 of SMN1.

An increase in luciferase expression from the SMN1-G minigene construct when compared to the SMN2-G minigene construct was expected. However, the SMN1-G minigene construct did not exhibit an increase in luciferase expression when it was compared to the SMN2-G minigene construct.

In order to determine why constructs with a guanine insert yielded results different from those expected, total RNA was isolated from cells transiently transfected with the SMN1 or SMN2 versions of the minigenes. Total RNA was reverse transcribed to produce the cDNA. The cDNA was then amplified by PCR with primers specific for the minigene/reporter gene transcript. The first primer annealed to the luciferase gene and the second primer to exon 6. The PCR products were resolved on a 2% agarose gel.

RNA isolated from HEK293H cells transfected with the SMN2-G minigene construct predominately showed a band corresponding to the size of a transcript that lacks exon 7. Expression of the SMN1-G minigene construct in transiently transfected HEK293H cells resulted in the appearance of an additional band corresponding to the transcript containing exon 7. The band corresponding to the transcript containing exon 7 produced from the SMN1-G minigene construct was isolated and cloned into a pCR-blunt vector (Invitrogen). 20 clones containing the SMN1-G minigene fragment were sequenced. All of the clones lacked seven nucleotides from the inserted guanine residue to the last nucleotide of exon 7 (GTAAGGA) (SEQ ID NO:14), demonstrating that the inclusion of exon 7 for the SMN1-G version of the minigene occurred through utilization of a cryptic splice site generated by the G insertion. Indeed, the G insertion resulted in generation of a sequence element (GTAAGG) (SEQ ID NO:15) reminiscent of the 5' end of intron 7 (GTAAGT) (SEQ ID NO:16). Therefore, the spliceosome preferentially used the 5' splice site between the nucleotide residue 48 of exon 7 and the G insertion (position 49). Utilization of the cryptic splice site resulted in a frameshift of the open reading frame that starts at the ATG immediately upstream of exon 6 of SMN as well as a stop codon before the luciferase portion of the minigene. Therefore, luciferase expression was substantially reduced from the SMN1-G minigene construct when a part of exon 7 was included. Analogously, the G insertion in the SMN2-G minigene construct creates a cryptic splice site in exon 7 of SMN2. The resulting inclusion of a fragment of exon 7 of SMN2 that lacks seven nucleotides at the 3' end significantly reduces luciferase expression from the SMN2-G minigene construct.

C-Terminal Extension of SMNΔEx7

To address whether the C-terminal extension of SMNΔEx7 would increase the amount of SMNΔEx7 protein, a plasmid encoding SMNΔEx7 was constructed. Using this plasmid, a second plasmid was constructed comprising a stop codon to leucine codon mutation (TAG to TTG) followed by four amino acids (serine, serine, threonine, lysine; "SSTK"; SEQ ID NO:27) that are encoded by the SMN2 mRNA (FIG. 3). Naturally-occurring SMNΔEx7 proteins then were separated from stabilized SMNΔEx7 proteins and levels of each were compared to assess whether the SSTK (SEQ ID NO:27) extension, which mimics read-through of SMNΔEx7, results in an increase in the level of SMNΔEx7 protein.

Materials and Methods

Preparation of the Minigene Constructs

DNA corresponding to a region of the SMN2 mRNA starting from the initiation codon and ending at nucleic acid residue 27 of exon 8 (GAAATGCTGGCA<u>TAG</u>AGCAGCACTAAA; the SMN2 stop codon is underlined) (SEQ ID NO:17) was amplified by PCR using the following primers: Forward primer: 5'-CGCAGGATCCGCGATGAGCAGCGGCGGCAGTGGTGGCGGCG-3' (SEQ ID NO:18) and Reverse primer: 5'-CGCAGGATCCTTTAGTGCTGCTCTATGCCAGCATTTCCATATAATAGCC-3' (SEQ ID NO:19). The 5' end of each primer was designed to incorporate a BamHI site into both the 5' end of the open reading frame and into the 3' end of exon 8, after the 27$^{th}$ nucleotide.

Using the BamHI restriction sites, the PCR fragment was cloned into a derivative of the original pcDNA 3.1/Hygro vector which was modified as disclosed in United States Patent Publication US2005/0048549. New UTRs were added to the modified vector using the HindIII site of the pcDNA 3.1/Hygro vector and the BamHI site comprising a 5'deg UTR (5'-TAGCTTCTTACCCGTACTCCACCGTTGGCAGCACGATCGCACGTCCCACGT GAACCATTGGTAAACCCTG-3') (SEQ ID NO:20) was cloned into the modified pcDNA3.1/Hygro vector together with a start codon upstream of the BamHI site; and a 3'deg UTR (5'-ATCGAAAGTACAGGACTAGCCTTCCTAGCAACCGCGGGCTGGGAGTCTGAGA CATCACTCAAGATATATGCTCGGTAACGTATGCTCTAGCCATCTAACTATTCCCT ATGTCTTATAGGG-3') (SEQ ID NO:21) was cloned into the modified pcDNA3.1/Hygro vector with a stop codon using the NotI site and the XhoI site of the modified pcDNA3.1/Hygro vector. In addition, a luciferase gene lacking its start codon was cloned into the vector using the BamHI and NotI sites of the modified pcDNA3.1/Hygro vector.

The resulting construct comprises, in 5' to 3' order: the 5'-deg UTR, the open reading frame of SMN2 mRNA (encoding SMNΔEx7 protein), stop codon of SMN2, 12 additional nucleotides from exon 8 (AGCAGCACTAAA) (SEQ ID NO:22), an additional six nucleotides forming a BamHI site, the luciferase gene lacking the start codon, and the 3'-deg UTR. This construct produces naturally-occurring SMN-ΔEx7 protein.

An adenine residue in the stop codon of SMN2 (GCA T<u>A</u>G AGC, underlined) was replaced with a thymine residue by site-directed mutagenesis (GCA T<u>T</u>G AGC, underlined) thus replacing the stop codon with a codon encoding leucine. The following primer was used for the mutagenesis: 5'-CGCAGGATCCTTTAGTGCTGCTCAATGCCAGCATTTCCATATAATAGCC-3' (SEQ ID NO:23). This construct was further mutagenized by site-directed mutagenesis to generate a stop codon after the 27$^{th}$ nucleotide of exon 8 (GAAATGCTGGCATAGAGCAGCACTAAA<u>TGA</u>; the introduced stop codon is underlined) (SEQ ID NO:24). The following primer was used for the mutagenesis: 5'-GGCATTGAGCAGCACTAAATGATCCGAAGACGCCAAAAAC-3' (SEQ ID NO:25). The resulting construct produces the SMNΔEx7-LSSTK (SEQ ID NO:26) extended protein which mimics a 100% readthrough of the SMN2 stop codon.

The constructs were transfected into HEK293H cells using techniques known in the art. The cells harboring the constructs were incubated for three days and cellular extracts were generated and analyzed by Western blot.

Western Blot Analysis

Proteins were separated using Laemmli Buffer in denaturing conditions on a polyacrylamide gel and transferred to a nitrocellulose membrane. The membrane was incubated with Odyssey blocking buffer (Li-Cor, catalog #927-40000) for 1 hour at room temperature with gentle shaking. Primary (anti-SMN) antibody (BD Transduction Laboratories, catalog #610646) was diluted with Odyssey blocking buffer containing 0.1% Tween 20 and incubated with the blocked membrane for 1 hour at room temperature with gentle shaking, followed by two washes for 5 minutes with 1×PBS containing 0.1% Tween 20.

In light protective conditions, secondary (anti-mouse) fluorescently-labeled antibody (Molecular Probes, catalog# A21057) was diluted with Odyssey blocking buffer containing 0.1% Tween 20 and incubated with the membrane for 1 hour at room temperature with gentle shaking. The membrane was washed 3 times for 15 minutes with 1×PBS containing 0.1% Tween 20 and then was rinsed once with 1×PBS. The amount of fluorescently-labeled secondary antibody bound to the primary antibody, which in turn is bound to a band corresponding to the SMN protein, was determined using a Li-Cor Odyssey Imager. The amount of protein was quantified using Odyssey's imaging software.

Results

The stabilized SMNΔEx7 protein comprising additional C-terminal amino acids (LSSTK; SEQ ID NO:26) conferred by the mutation of the stop codon in naturally-occurring SMNΔEx7 protein results in significantly increased levels of SMNΔEx7 protein as compared to levels of SMNΔEx7 protein observed naturally-occurring SMNΔEx7 comprising the native stop codon (FIG. 4).

The present invention is not to be limited in scope by the specific embodiments described herein. Indeed, various modifications of the invention and their equivalents, in addition to those described herein will become apparent to those skilled in the art from the foregoing description and accompanying figures. Such modifications are intended to fall within the scope of the appended claims.

Various patents, patent applications, and publications are cited herein, the disclosures of which are incorporated by reference in their entirety and for all purposes.

What is claimed:

1. A method for the identification of a compound that produces a stabilized SMNΔEx7 protein comprising:

(A) contacting a compound with either a host cell containing an mRNA transcript transcribed from a nucleic acid construct, or a composition comprising a cell-free extract and an mRNA transcript transcribed from a nucleic acid construct, wherein the nucleic acid construct comprises, in 5' to 3' order:

(a) a start codon;

(b) a fragment of the nucleic acid residues of exon 8 of SMN; and (c) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and a stop codon is upstream of the reporter gene coding sequence in the mRNA transcript; and (ii) the start codon and the stop codon upstream of the reporter gene coding sequence in the mRNA transcript are in the same contiguous open reading frame;

(B) detecting the activity or amount of a fusion protein translated from the mRNA transcript, wherein an increase in the activity or amount of the fusion protein translated from the mRNA transcript in the presence of a compound when compared to:

(i) a previously determined reference range for a negative control, (ii) the activity or amount of the fusion protein translated from the mRNA transcript in the absence of the compound, or (iii) the activity or amount of the fusion protein translated from the mRNA transcript in the presence of a negative control indicates that the compound produces a stabilized SMNΔEx7 protein; and (C) contacting a compound that increases the activity or amount of the fusion protein translated from the mRNA transcript with a cell that produces SMNΔEx7 protein and assaying the ability of the compound to increase the level of stabilized SMNΔEx7 protein in the cell in the presence of the compound as compared to the level of SMNΔEx7 protein in the cell in the presence of the compound, wherein an increase in the level of stabilized SMNΔEx7 protein relative to the level of SMNΔEx7 protein indicates that a compound that produces a stabilized SMNΔEx7 protein is identified, wherein said stabilized SMNΔEx7 protein comprises the amino acid sequence of SEQ ID NO:2, SEQ ID NO:3, SEQ ID NO:4, or SEQ ID NO:5.

2. The method of claim 1, wherein the nucleic acid construct comprises a fragment of the nucleic acid residues of exon 7 of SMN downstream (3') of the start codon and upstream (5') of the fragment of the nucleic acid residues of exon 8 of SMN, and wherein the fragment of the nucleic acid residues of exon 7 of SMN comprises any number of nucleotides of exon 7 of SMN so long as in the mRNA transcript the start codon and the stop codon upstream of the reporter gene coding sequence are maintained in the same contiguous open reading frame.

3. A method for the identification of a compound that produces a stabilized SMNΔEx7 protein comprising:

(A) contacting a compound with either a host cell containing an mRNA transcript transcribed from a nucleic acid construct, or a composition comprising a cell-free extract and an mRNA transcript transcribed from a nucleic acid construct, wherein the nucleic acid construct comprises, in 5' to 3' order:

(a) a start codon;

(b) the nucleic acid residues of exon 7 of SMN, wherein any number of nucleotides are inserted after the $48^{th}$ nucleotide residue from the 5' end of exon 7 of SMN as long as the native stop codon of exon 7 of SMN is inactivated and any additional stop codon is not generated;

(c) a fragment of the nucleic acid residues of exon 8 of SMN; and (d) a reporter gene coding sequence lacking a start codon, wherein:

(i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon upstream of the reporter gene coding sequence in the region of the mRNA transcript that corresponds to the fragment of the nucleic acid residues of exon 8 of SMN; and (ii) the start codon and the stop codon upstream from the reporter gene coding sequence in the mRNA transcript are in the same contiguous open reading frame;

(B) detecting the activity or amount of a fusion protein translated from the mRNA transcript, wherein an increase in the activity or amount of the fusion protein translated from the mRNA transcript in the presence of a compound when compared to:

(i) a previously determined reference range for a negative control, (ii) the activity or amount of the fusion protein translated from the mRNA transcript in the absence of the compound, or (iii) the activity or amount of the fusion protein translated from the mRNA transcript in the presence of a negative control indicates that the compound produces a stabilized SMNΔEx7 protein; and (C) contacting a compound that increases the activity or amount of the fusion protein translated from the mRNA transcript with a cell that produces SMNΔEx7 protein and assaying the ability of the compound to increase the level of stabilized SMNΔEx7 protein in the cell in the presence of the compound as compared to the level of SMNΔEx7 protein in the cell in the presence of the compound, wherein an increase in the level of stabilized SMNΔEx7 protein relative to the level of SMNΔEx7 protein indicates that a compound that produces a stabilized SMNΔEx7 protein is identified, wherein said stabilized SMNΔEx7 protein comprises the amino acid sequence of SEQ ID NO:2, SEQ ID NO:3, SEQ ID NO:4, or SEQ ID NO:5.

4. The method of claim 3, wherein: (a) the nucleic acid construct comprises the nucleic acid residues of exon 6 of SMN or a fragment thereof downstream (3') of the start codon and upstream (5') of the nucleic acid residues of exon 7 of SMN, wherein the fragment of the nucleic acid residues of exon 6 of SMN comprises any number of nucleotides of exon 6 of SMN so long as in the mRNA transcript the start codon and the stop codon upstream of the reporter gene coding sequence are maintained in the same contiguous open reading frame; or (b) the nucleic acid construct comprises the nucleic acid residues of intron 7 of SMN or a fragment thereof downstream (3') of the nucleic acid residues of exon 7 of SMN and upstream (5') of the fragment of the nucleic acid residues of exon 8 of SMN, wherein the fragment of the nucleic acid residues of intron 7 comprises any number of nucleotides of intron 7 of SMN required for a functional, minimum intron.

5. A method for the identification of a compound that produces a stabilized SMNΔEx7 protein comprising:

(A) contacting a compound with either a host cell containing an mRNA transcript transcribed from a nucleic acid construct, or a composition comprising a cell-free extract and an mRNA transcript transcribed from a nucleic acid construct, in 5' to 3' order:

(a) a start codon;

(b) the nucleic acid residues of exon 7 of SMN, wherein a single guanine residue is inserted after the $48^{th}$ nucleotide residue from the 5' end of exon 7 of SMN;

(c) the nucleic acid residues of intron 7 of SMN or a fragment thereof, wherein the fragment of the nucleic acid residues of intron 7 comprises any number of nucleotides of intron 7 of SMN required for a functional, minimum intron;

(d) a fragment of the nucleic acid residues of exon 8 of SMN; and (e) a reporter gene coding sequence lacking a start codon, wherein:

(i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; and (ii) the production of the mRNA transcript generates a stop codon upstream from the reporter gene coding sequence in the region of the mRNA transcript that corresponds to the fragment of the nucleic acid residues of exon 8 of SMN; and (iii) the start codon and the stop codon upstream from the reporter gene coding sequence in the mRNA transcript are in the same contiguous open reading frame;

(B) detecting the activity or amount of a fusion protein translated from the mRNA transcript, wherein an increase in the activity or amount of the fusion protein translated from the mRNA transcript in the presence of a compound when compared to:

(i) a previously determined reference range for a negative control, (ii) the activity or amount of the fusion protein translated from the mRNA transcript in the absence of the compound, or (iii) the activity or amount of the fusion protein translated from the mRNA transcript in the presence of a negative control indicates that the compound produces a stabilized SMNΔEx7 protein; and (C) contacting a compound that increases the activity or amount of the fusion protein translated from the mRNA transcript with a cell that produces SMNΔEx7 protein and assaying the ability of the compound to increase the level of stabilized SMNΔEx7 protein in the cell in the presence of the compound as compared to the level of SMNΔEx7 protein in the cell in the presence of the compound, wherein an increase in the level of stabilized SMNΔEx7 protein relative to the level of SMNΔEx7 protein indicates that a compound that produces a stabilized SMNΔEx7 protein is identified, wherein said stabilized SMNΔEx7 protein comprises the amino acid sequence of SEQ ID NO:2, SEQ ID NO:3, SEQ ID NO:4, or SEQ ID NO:5.

6. The method of claim 5, wherein the nucleic acid construct comprises the nucleic acid residues of exon 6 of SMN or a fragment thereof downstream (3') to the start codon and upstream (5') of the nucleic acid residues of exon 7 of SMN, wherein the fragment of the nucleic acid residues of exon 6 of SMN comprises any number of nucleotides of exon 6 of SMN so long as in the mRNA transcript the start codon and the stop codon upstream of the reporter gene coding sequence are maintained in the same contiguous open reading frame.

7. A method for the identification of a compound that produces a stabilized SMNΔEx7 protein comprising:

(A) contacting a compound with either a host cell containing an mRNA transcript transcribed from a nucleic acid construct, or a composition comprising a cell-free extract and an mRNA transcript transcribed from a nucleic acid construct, in 5' to 3' order:

(a) a start codon;

(b) a minimum of one nucleotide;

(c) a fragment of the nucleic acid residues of exon 7 of SMN, wherein (i) the fragment of the nucleic acid residues of exon 7 of SMN comprises a minimum of the first six nucleotides from the 3' end of exon 7 of SMN and wherein a single guanine residue is inserted into the fragment of the nucleic acid residues of exon 7 of SMN at the location that corresponds to the location in exon 7 of SMN that is after the $48^{th}$ nucleotide from the 5' end of exon 7 of SMN or (ii) the fragment of the nucleic acid residues of exon 7 of SMN consists of the first six nucleotides from the 3' end of exon 7 of SMN and wherein a single guanine residue is inserted upstream (5') of the fragment of the nucleic acid residues of exon 7 of SMN;

(d) the nucleic acid residues of intron 7 of SMN or a fragment thereof, wherein the fragment of the nucleic acid residues of intron 7 of SMN comprises any number of nucleotides of intron 7 required for a functional, minimum intron;

(e) a fragment of the nucleic acid residues of exon 8 of SMN; and (f) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; and (ii) the production of the mRNA transcript generates a stop codon upstream from the reporter gene coding sequence in the region of the mRNA transcript that corresponds to the fragment of the nucleic acid residues of exon 8 of SMN; and (iii) the start codon and the stop codon upstream from the reporter gene coding sequence in the mRNA transcript are in the same contiguous open reading frame;

(B) detecting the activity or amount of a fusion protein translated from the mRNA transcript, wherein an increase in the activity or amount of the fusion protein translated from the mRNA transcript in the presence of a compound when compared to:

(i) a previously determined reference range for a negative control, (ii) the activity or amount of the fusion protein translated from the mRNA transcript in the absence of the compound, or (iii) the activity or amount of the fusion protein translated from the mRNA transcript in the presence of a negative control indicates that the compound produces a stabilized SMNΔEx7 protein; and (C) contacting a compound that increases the activity or amount of the fusion protein translated from the mRNA transcript with a cell that produces SMNΔEx7 protein and assaying the ability of the compound to increase the level of stabilized SMNΔEx7 protein in the cell in the presence of the compound as compared to the level of SMNΔEx7 protein in the cell in the presence of the compound, wherein an increase in the level of stabilized SMNΔEx7 protein relative to the level of SMNΔEx7 protein indicates that a compound that produces a stabilized SMNΔEx7 protein is identified, wherein said stabilized SMNΔEx7 protein comprises the amino acid sequence of SEQ ID NO:2, SEQ ID NO:3, SEQ ID NO:4, or SEQ ID NO:5.

8. The method of claim 7, wherein the nucleic acid construct comprises the nucleic acid residues of exon 6 of SMN or a fragment thereof downstream (3') to the start codon and upstream (5') of the nucleic acid residues of exon 7 of SMN, wherein the fragment of the nucleic acid residues of exon 6 of SMN comprises any number of nucleotides of exon 6 of SMN so long as in the mRNA transcript the start codon and the stop codon upstream of the reporter gene coding sequence are maintained in the same contiguous open reading frame.

9. The method of claim 8, wherein the nucleic acid construct comprises the nucleic acid residues of intron 6 of SMN or a fragment thereof downstream (3') of the nucleic acid residues of exon 6 of SMN or a fragment thereof and upstream (5') of the nucleic acid residues of exon 7 of SMN, wherein the fragment of the nucleic acid residues of intron 6 of SMN comprises any number of nucleotides of intron 6 of SMN required for a functional, minimum intron.

* * * * *

SEQUENCE LISTING

```
<160> NUMBER OF SEQ ID NOS: 25

<210> SEQ ID NO 1
<211> LENGTH: 282
<212> TYPE: PRT
<213> ORGANISM: Homo sapiens

<400> SEQUENCE: 1

Met Ala Met Ser Ser Gly Gly Ser Gly Gly Gly Val Pro Glu Gln Glu
 1               5                  10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
        35                  40                  45

Ser Phe Lys His Ala Leu Lys Asn Gly Asp Ile Cys Glu Thr Ser Gly
    50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
            100                 105                 110

Ile Ala Ser Ile Asp Phe Lys Arg Glu Thr Cys Val Val Val Tyr Thr
        115                 120                 125

Gly Tyr Gly Asn Arg Glu Glu Gln Asn Leu Ser Asp Leu Leu Ser Pro
    130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
            180                 185                 190

Phe Leu Pro Pro Pro Pro Pro Met Pro Gly Pro Arg Leu Gly Pro Gly
```

```
        195                 200                 205

Lys Pro Gly Leu Lys Phe Asn Gly Pro Pro Pro Pro Pro Pro Pro Pro
    210                 215                 220

Pro Pro His Leu Leu Ser Cys Trp Leu Pro Pro Phe Pro Ser Gly Pro
225                 230                 235                 240

Pro Ile Ile Pro Pro Pro Pro Pro Ile Cys Pro Asp Ser Leu Asp Asp
                245                 250                 255

Ala Asp Ala Leu Gly Ser Met Leu Ile Ser Trp Tyr Met Ser Gly Tyr
            260                 265                 270

His Thr Gly Tyr Tyr Met Glu Met Leu Ala
        275                 280


<210> SEQ ID NO 2
<211> LENGTH: 285
<212> TYPE: PRT
<213> ORGANISM: Artificial Sequence
<220> FEATURE:
<223> OTHER INFORMATION: Stabilized SMNAEx7 protein produced by +2
      frameshift

<400> SEQUENCE: 2

Met Ala Met Ser Ser Gly Gly Ser Gly Gly Gly Val Pro Glu Gln Glu
 1               5                  10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
        35                  40                  45

Ser Phe Lys His Ala Leu Lys Asn Gly Asp Ile Cys Glu Thr Ser Gly
    50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
            100                 105                 110

Ile Ala Ser Ile Asp Phe Lys Arg Glu Thr Cys Val Val Val Tyr Thr
        115                 120                 125

Gly Tyr Gly Asn Arg Glu Glu Gln Asn Leu Ser Asp Leu Leu Ser Pro
    130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
            180                 185                 190

Phe Leu Pro Pro Pro Pro Pro Met Pro Gly Pro Arg Leu Gly Pro Gly
        195                 200                 205

Lys Pro Gly Leu Lys Phe Asn Gly Pro Pro Pro Pro Pro Pro Pro Pro
    210                 215                 220

Pro Pro His Leu Leu Ser Cys Trp Leu Pro Pro Phe Pro Ser Gly Pro
225                 230                 235                 240

Pro Ile Ile Pro Pro Pro Pro Pro Ile Cys Pro Asp Ser Leu Asp Asp
                245                 250                 255

Ala Asp Ala Leu Gly Ser Met Leu Ile Ser Trp Tyr Met Ser Gly Tyr
            260                 265                 270
```

```
His Thr Gly Tyr Tyr Met Glu Met Leu Ala Glu Gln His
        275                280                285


<210> SEQ ID NO 3
<211> LENGTH: 286
<212> TYPE: PRT
<213> ORGANISM: Artificial Sequence
<220> FEATURE:
<223> OTHER INFORMATION: Stabilized SMNAEx7 protein produced by -1
      frameshift

<400> SEQUENCE: 3

Met Ala Met Ser Ser Gly Gly Ser Gly Gly Gly Val Pro Glu Gln Glu
 1               5                  10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
        35                  40                  45

Ser Phe Lys His Ala Leu Lys Asn Gly Asp Ile Cys Glu Thr Ser Gly
    50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
            100                 105                 110

Ile Ala Ser Ile Asp Phe Lys Arg Glu Thr Cys Val Val Val Tyr Thr
        115                 120                 125

Gly Tyr Gly Asn Arg Glu Glu Gln Asn Leu Ser Asp Leu Leu Ser Pro
    130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
            180                 185                 190

Phe Leu Pro Pro Pro Pro Pro Met Pro Gly Pro Arg Leu Gly Pro Gly
        195                 200                 205

Lys Pro Gly Leu Lys Phe Asn Gly Pro Pro Pro Pro Pro Pro Pro Pro
    210                 215                 220

Pro Pro His Leu Leu Ser Cys Trp Leu Pro Pro Phe Pro Ser Gly Pro
225                 230                 235                 240

Pro Ile Ile Pro Pro Pro Pro Pro Ile Cys Pro Asp Ser Leu Asp Asp
                245                 250                 255

Ala Asp Ala Leu Gly Ser Met Leu Ile Ser Trp Tyr Met Ser Gly Tyr
            260                 265                 270

His Thr Gly Tyr Tyr Met Glu Met Leu Ala Ile Glu Gln His
        275                 280                 285


<210> SEQ ID NO 4
<211> LENGTH: 305
<212> TYPE: PRT
<213> ORGANISM: Artificial Sequence
<220> FEATURE:
<223> OTHER INFORMATION: Stabilized SMNAEx7 protein produced by +1
      frameshift

<400> SEQUENCE: 4
```

```
Met Ala Met Ser Ser Gly Gly Ser Gly Gly Gly Val Pro Glu Gln Glu
 1               5                  10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
        35                  40                  45

Ser Phe Lys His Ala Leu Lys Asn Gly Asp Ile Cys Glu Thr Ser Gly
    50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
            100                 105                 110

Ile Ala Ser Ile Asp Phe Lys Arg Glu Thr Cys Val Val Val Tyr Thr
        115                 120                 125

Gly Tyr Gly Asn Arg Glu Glu Gln Asn Leu Ser Asp Leu Leu Ser Pro
    130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
            180                 185                 190

Phe Leu Pro Pro Pro Pro Pro Met Pro Gly Pro Arg Leu Gly Pro Gly
        195                 200                 205

Lys Pro Gly Leu Lys Phe Asn Gly Pro Pro Pro Pro Pro Pro Pro Pro
    210                 215                 220

Pro Pro His Leu Leu Ser Cys Trp Leu Pro Pro Phe Pro Ser Gly Pro
225                 230                 235                 240

Pro Ile Ile Pro Pro Pro Pro Pro Ile Cys Pro Asp Ser Leu Asp Asp
                245                 250                 255

Ala Asp Ala Leu Gly Ser Met Leu Ile Ser Trp Tyr Met Ser Gly Tyr
            260                 265                 270

His Thr Gly Tyr Tyr Met Glu Met Leu Ala Arg Ala Ala Leu Asn Asp
        275                 280                 285

Thr Thr Lys Glu Thr Ile Arg Gln Ile Trp Asn Val Lys Arg Tyr Arg
    290                 295                 300

Arg
305
```

<210> SEQ ID NO 5
<211> LENGTH: 306
<212> TYPE: PRT
<213> ORGANISM: Artificial Sequence
<220> FEATURE:
<223> OTHER INFORMATION: Stabilized SMNAEx7 protein produced by -2 frameshift

<400> SEQUENCE: 5

```
Met Ala Met Ser Ser Gly Gly Ser Gly Gly Gly Val Pro Glu Gln Glu
 1               5                  10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
        35                  40                  45
```

```
Ser Phe Lys His Ala Leu Lys Asn Gly Asp Ile Cys Glu Thr Ser Gly
    50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
            100                 105                 110

Ile Ala Ser Ile Asp Phe Lys Arg Glu Thr Cys Val Val Val Tyr Thr
        115                 120                 125

Gly Tyr Gly Asn Arg Glu Glu Gln Asn Leu Ser Asp Leu Leu Ser Pro
    130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
            180                 185                 190

Phe Leu Pro Pro Pro Pro Pro Met Pro Gly Pro Arg Leu Gly Pro Gly
        195                 200                 205

Lys Pro Gly Leu Lys Phe Asn Gly Pro Pro Pro Pro Pro Pro Pro Pro
    210                 215                 220

Pro Pro His Leu Leu Ser Cys Trp Leu Pro Pro Phe Pro Ser Gly Pro
225                 230                 235                 240

Pro Ile Ile Pro Pro Pro Pro Pro Ile Cys Pro Asp Ser Leu Asp Asp
                245                 250                 255

Ala Asp Ala Leu Gly Ser Met Leu Ile Ser Trp Tyr Met Ser Gly Tyr
            260                 265                 270

His Thr Gly Tyr Tyr Met Glu Met Leu Ala His Arg Ala Ala Leu Asn
        275                 280                 285

Asp Thr Thr Lys Glu Thr Ile Arg Gln Ile Trp Asn Val Lys Arg Tyr
    290                 295                 300

Arg Arg
305
```

```
<210> SEQ ID NO 6
<211> LENGTH: 8266
<212> TYPE: DNA
<213> ORGANISM: Artificial Sequence
<220> FEATURE:
<223> OTHER INFORMATION: DNA sequence of the minigene from the SMN-G
      minigene construct

<400> SEQUENCE: 6

tagcttctta cccgtactcc accgttggca gcacgatcgc acgtcccacg tgaaccattg      60

gtaaaccctg atgggatcca taattccccc accacctccc atatgtccag attctcttga     120

tgatgctgat gctttgggaa gtatgttaat ttcatggtac atgagtggct atcatactgg     180

ctattatatg gtaagtaatc actcagcatc ttttcctgac aatttttttg tagttatgtg     240

actttgtttt gtaaatttat aaaatactac ttgcttctct ctttatatta ctaaaaaata     300

aaaataaaaa aatacaactg tctgaggctt aaattactct tgcattgtcc ctaagtataa     360

ttttagttaa ttttaaaaag ctttcatgct attgttagat tattttgatt atacactttt     420

gaattgaaat tatacttttt ctaaataatg ttttaatctc tgatttgaaa ttgattgtag     480
```

```
ggaatggaaa agatgggata atttttcata aatgaaaaat gaaattcttt tttttttttt    540
tttttttttg agacggagtc ttgctctgtt gcccaggctg gagtgcaatg gcgtgatctt    600
ggctcacagc aagctctgcc tcctggattc acgccattct cctgcctcag cctcagaggt    660
agctgggact acaggtgcct gccaccacgc ctgtctaatt ttttgtattt ttttgtaaag    720
acagggtttc actgtgttag ccaggatggt ctcaatctcc tgaccccgtg atccacccgc    780
ctcggccttc caagagaaat gaaatttttt taatgcacaa agatctgggg taatgtgtac    840
cacattgaac cttggggagt atggcttcaa acttgtcact ttatacgtta gtctcctacg    900
gacatgttct attgtatttt agtcagaaca tttaaaatta ttttatttta ttttattttt    960
tttttttttt tgagacggag tctcgctctg tcacccaggc tggagtacag tggcgcagtc   1020
tcggctcact gcaagctccg cctcccgggt tcacgccatt ctcctgcctc agcctctccg   1080
agtagctggg actacaggcg cccgccacca cgcccggcta attttttttt atttttagta   1140
gagacggggt ttcaccgtgg tctcgatctc ctgacctcgt gatccacccg cctcggcctc   1200
ccaaagtgct gggattacaa gcgtgagcca ccgcgcccgg cctaaaatta tttttaaaag   1260
taagctcttg tgccctgcta aaattatgat gtgatattgt aggcacttgt atttttagta   1320
aattaatata gaagaaacaa ctgacttaaa ggtgtatgtt tttaaatgta tcatctgtgt   1380
gtgcccccat taatattctt atttaaaagt taaggccaga catggtggct tacaactgta   1440
atcccaacag tttgtgaggc cgaggcaggc agatcacttg aggtcaggag tttgagacca   1500
gcctggccaa catgatgaaa ccttgtctct actaaaaata ccaaaaaaaa tttagccagg   1560
catggtggca catgcctgta atccgagcta cttgggaggc tgtggcagga aaattgcttt   1620
aatctgggag gcagaggttg cagtgagttg agattgtgcc actgcactcc acccttggtg   1680
acagagtgag attccatctc aaaaaaagaa aaaggcctgg cacggtggct cacacctata   1740
atcccagtac tttgggaggt agaggcaggt ggatcacttg aggttaggag ttcaggacca   1800
gcctggccaa catggtgact actccatttc tactaaatac acaaaactta gcccagtggc   1860
gggcagttgt aatcccagct acttgagagg ttgaggcagg agaatcactt gaacctggga   1920
ggcagaggtt gcagtgagcc gagatcacac cgctgcactc tagcctggcc aacagagtga   1980
gaatttgcgg agggaaaaaa aagtcacgct tcagttgttg tagtataacc ttggtatatt   2040
gtatgtatca tgaattcctc attttaatga ccaaaaagta ataaatcaac agcttgtaat   2100
ttgttttgag atcagttatc tgactgtaac actgtaggct tttgtgtttt ttaaattatg   2160
aaatatttga aaaaaataca taatgtatat ataaagtatt ggtataattt atgttctaaa   2220
taactttctt gagaaataat tcacatggtg tgcagtttac ctttgaaagt atacaagttg   2280
gctgggcaca atggctcacg cctgtaatcc cagcactttg ggaggccagg gcaggtggat   2340
cacgaggtca ggagatcgag accatcctgg ctaacatggt gaaaccccgt ctctactaaa   2400
agtacaaaaa caaattagcc gggcatgttg gcgggcacct tttgtcccag ctgctcggga   2460
ggctgaggca ggagagtggc gtgaacccag gaggtggagc ttgcagtgag ccgagattgt   2520
gccagtgcac tccagcctgg gcgacagagc gagactctgt ctcaaaaaat aaaataaaaa   2580
agaaagtata caagtcagtg gttttggttt tcagttatgc aaccatcact acaatttaag   2640
aacattttca tcaccccaaa aagaaaccct gttaccttca ttttccccag ccctaggcag   2700
tcagtacact ttctgtctct atgaatttgt ctattttaga tattatatat aaacggaatt   2760
atacgatatg tggtcttttg tgtctggctt ctttcactta gcatgctatt ttcaagattc   2820
atccatgctg tagaatgcac cagtactgca ttccttctta ttgctgaata ttctgttgtt   2880
```

```
tggttatatc acattttatc cattcatcag ttcatggaca tttaggttgt ttttattttt   2940

gggctataat gaataatgtt gctatgaaca ttcgtttgtg ttctttttgt ttttttggtt   3000

ttttgggttt tttttgtttt gtttttgttt ttgagacagt cttgctctgt ctcctaagct   3060

ggagtgcagt ggcatgatct tggcttactg caagctctgc ctcccgggtt cacaccattc   3120

tcctgcctca gcccgacaag tagctgggac tacaggcgtg tgccaccatg cacggctaat   3180

tttttgtatt tttagtagag atggggtttc accgtgttag ccaggatggt ctcgatctcc   3240

tgacctcgtg atctgcctgc ctaggcctcc caaagtgctg ggattacagg cgtgagccac   3300

tgcacctggc cttaagtgtt tttaatacgt cattgcctta agctaacaat tcttaacctt   3360

tgttctactg aagccacgtg gttgagatag gctctgagtc tagcttttaa cctctatctt   3420

tttgtcttag aaatctaagc agaatgcaaa tgactaagaa taatgttgtt gaaataacat   3480

aaaataggtt ataactttga tactcattag taacaaatct ttcaatacat cttacggtct   3540

gttaggtgta gattagtaat gaagtgggaa gccactgcaa gctagtatac atgtagggaa   3600

agatagaaag cattgaagcc agaagagaga cagaggacat ttgggctaga tctgacaaga   3660

aaaacaaatg ttttagtatt aatttttgac tttaaatttt tttttttattt agtgaatact   3720

ggtgtttaat ggtctcattt taataagtat gacacaggta gtttaaggtc atatatttta   3780

tttgatgaaa ataaggtata ggccgggcac ggtggctcac acctgtaatc ccagcacttt   3840

gggaggccga ggcaggcgga tcacctgagg tcgggagtta gagactagcc tcaacatgga   3900

gaaaccccgt ctctactaaa aaaaatacaa aattaggcgg gcgtggtggt gcatgcctgt   3960

aatcccagct actcaggagg ctgaggcagg agaattgctt gaacctggga ggtggaggtt   4020

gcggtgagcc gagatcacct cattgcactc cagcctgggc aacaagagca aaactccatc   4080

tcaaaaaaaa aaaaataagg tataagcggg ctcaggaaca tcattggaca tactgaaaga   4140

agaaaaatca gctgggcgca gtggctcacg ccggtaatcc caacactttg ggaggccaag   4200

gcaggcgaat cacctgaagt cgggagttcc agatcagcct gaccaacatg gagaaaccct   4260

gtctctacta aaaatacaaa actagccggg catggtggcg catgcctgta atcccagcta   4320

cttgggaggc tgaggcagga gaattgcttg aaccgagaag gcggaggttg cggtgagcca   4380

agattgcacc attgcactcc agcctgggca acaagagcga aactccgtct caaaaaaaaa   4440

aggaagaaaa atattttttt aaattaatta gtttatttat tttttaagat ggagttttgc   4500

cctgtcaccc aggctggggt gcaatggtgc aatctcggct cactgcaacc tccgcctcct   4560

gggttcaagt gattctcctg cctcagcttc ccgagtagct gtgattacag ccatatgcca   4620

ccacgcccag ccagttttgt gttttgtttt gtttttttgtt tttttttttt gagagggtgt   4680

cttgctctgt cccccaagct ggagtgcagc ggcgcgatct tggctcactg caagctctgc   4740

ctcccaggtt cacaccattc tcttgcctca gcctcccgag tagctgggac tacaggtgcc   4800

cgccaccaca cccggctaat ttttttgtgt ttttagtaga gatggggttt cactgtgtta   4860

gccaggatgg tctcgatctc ctgacctttt gatccacccg cctcagcctc cccaagtgct   4920

gggattatag gcgtgagcca ctgtgcccgg cctagtcttg tatttttagt agagtcggga   4980

tttctccatg ttggtcaggc tgttctccaa atccgacctc aggtgatccg cccgccttgg   5040

cctccaaaag tgcaaggcaa ggcattacag gcatgagcca ctgtgaccgg caatgttttt   5100

aaatttttta catttaaatt ttattttttta gagaccaggt ctcactctat tgctcaggct   5160

ggagtgcaag ggcacattca cagctcactg cagccttgac ctccagggct caagcagtcc   5220
```

-continued

```
tctcacctca gtttcccgag tagctgggac tacagtgata atgccactgc acctggctaa   5280
tttttatttt tatttattta ttttttttg agacagagtc ttgctctgtc acccaggctg    5340
gagtgcagtg gtgtaaatct cagctcactg cagcctccgc ctcctgggtt caagtgattc   5400
tcctgcctca acctcccaag tagctgggat tagaggtccc caccaccatg cctggctaat   5460
tttttgtact ttcagtagaa acggggtttt gccatgttgg ccaggctgtt ctcgaactcc   5520
tgagctcagg tgatccaact gtctcggcct cccaaagtgc tgggattaca ggcgtgagcc   5580
actgtgccta gcctgagcca ccacgccggc ctaattttta aattttttgt agagacaggg   5640
tctcattatg ttgcccaggg tggtgtcaag ctccaggtct caagtgatcc ccctacctcc   5700
gcctcccaaa gttgtgggat tgtaggcatg agccactgca agaaaacctt aactgcagcc   5760
taataattgt tttctttggg ataactttta aagtacatta aaagactatc aacttaattt   5820
ctgatcatat tttgttgaat aaaataagta aaatgtcttg tgaaacaaaa tgctttttaa   5880
catccatata aagctatcta tatatagcta tctatatcta tatagctatt tttttaact    5940
tcctttattt tccttacagg gttttagaca aaatcaaaaa gaaggaaggt gctcacattc   6000
cttaaatgta aggagtaagt ctgccagcat tatgaaagtg aatcttactt ttgtaaaact   6060
ttatggtttg tggaaaacaa atgtttttga acatttaaaa agttcagatg ttagaaagtt   6120
gaaaggttaa tgtaaaacaa tcaatattaa agaattttga tgccaaaact attagataaa   6180
aggttaatct acatccctac tagaattctc atacttaact ggttggttgt gtggaagaaa   6240
catactttca caataaagag ctttaggata tgatgccatt ttatatcact agtaggcaga   6300
ccagcagact ttttttattt gtgatatggg ataacctagg catactgcac tgtacactct   6360
gacatatgaa gtgctctagt caagtttaac tggtgtccac agaggacatg gtttaactgg   6420
aattcgtcaa gcctctggtt ctaatttctc atttgcagga aatgctggca tagagcagca   6480
cggatccgaa gacgccaaaa acataaagaa aggcccggcg ccattctatc ctctagagga   6540
tggaaccgct ggagagcaac tgcataaggc tatgaagaga tacgccctgg ttcctggaac   6600
aattgctttt acagatgcac atatcgaggt gaacatcacg tacgcggaat acttcgaaat   6660
gtccgttcgg ttggcagaag ctatgaaacg atatgggctg aatacaaatc acagaatcgt   6720
cgtatgcagt gaaaactctc ttcaattctt tatgccggtg ttgggcgcgt tatttatcgg   6780
agttgcagtt gcgcccgcga acgacattta taatgaacgt gaattgctca acagtatgaa   6840
catttcgcag cctaccgtag tgtttgtttc caaaaagggg ttgcaaaaaa ttttgaacgt   6900
gcaaaaaaaa ttaccaataa tccagaaaat tattatcatg gattctaaaa cggattacca   6960
gggatttcag tcgatgtaca cgttcgtcac atctcatcta cctcccggtt ttaatgaata   7020
cgattttgta ccagagtcct ttgatcgtga caaaacaatt gcactgataa tgaattcctc   7080
tggatctact gggttaccta agggtgtggc ccttccgcat agaactgcct gcgtcagatt   7140
ctcgcatgcc agagatccta tttttggcaa tcaaatcatt ccggatactg cgattttaag   7200
tgttgttcca ttccatcacg gttttggaat gtttactaca ctcggatatt tgatatgtgg   7260
atttcgagtc gtcttaatgt atagatttga agaagagctg tttttacgat cccttcagga   7320
ttacaaaatt caaagtgcgt tgctagtacc aaccctattt tcattcttcg ccaaaagcac   7380
tctgattgac aaatacgatt tatctaattt acacgaaatt gcttctgggg gcgcacctct   7440
ttcgaaagaa gtcggggaag cggttgcaaa acgcttccat cttccaggga tacgacaagg   7500
atatgggctc actgagacta catcagctat tctgattaca cccgaggggg atgataaacc   7560
gggcgcggtc ggtaaagttg ttccattttt tgaagcgaag gttgtggatc tggataccgg   7620
```

```
gaaaacgctg ggcgttaatc agagaggcga attatgtgtc agaggaccta tgattatgtc   7680

cggttatgta aacaatccgg aagcgaccaa cgccttgatt gacaaggatg gatggctaca   7740

ttctggagac atagcttact gggacgaaga cgaacacttc ttcatagttg accgcttgaa   7800

gtctttaatt aaatacaaag gatatcaggt ggcccccgct gaattggaat cgatattgtt   7860

acaacacccc aacatcttcg acgcgggcgt ggcaggtctt cccgacgatg acgccggtga   7920

acttcccgcc gccgttgttg ttttggagca cggaaagacg atgacggaaa aagagatcgt   7980

ggattacgtc gccagtcaag taacaaccgc gaaaaagttg cgcggaggag ttgtgtttgt   8040

ggacgaagta ccgaaaggtc ttaccggaaa actcgacgca agaaaaatca gagagatcct   8100

cataaaggcc aagaagggcg gaaagtccaa attgcgcggc cgctaaatcg aaagtacagg   8160

actagccttc ctagcaaccg cgggctggga gtctgagaca tcactcaaga tatatgctcg   8220

gtaacgtatg ctctagccat ctaactattc cctatgtctt ataggg                  8266
```

<210> SEQ ID NO 7
<211> LENGTH: 11
<212> TYPE: DNA
<213> ORGANISM: Artificial Sequence
<220> FEATURE:
<223> OTHER INFORMATION: DNA corresponding to a region of the SMN2 gene starting from the 5' end of exon 6

<400> SEQUENCE: 7

```
ataattcccc c                                                          11
```

<210> SEQ ID NO 8
<211> LENGTH: 6
<212> TYPE: DNA
<213> ORGANISM: Artificial Sequence
<220> FEATURE:
<223> OTHER INFORMATION: DNA corresponding to a region of the SMN2 gene ending at nucleic acid residue 23 of exon 8

<400> SEQUENCE: 8

```
cagcac                                                                 6
```

<210> SEQ ID NO 9
<211> LENGTH: 28
<212> TYPE: DNA
<213> ORGANISM: Artificial Sequence
<220> FEATURE:
<223> OTHER INFORMATION: Forward Primer used to generate DNA corresponding to a region of the SMN2 gene

<400> SEQUENCE: 9

```
cgcggatcca taattccccc accacctc                                        28
```

<210> SEQ ID NO 10
<211> LENGTH: 28
<212> TYPE: DNA
<213> ORGANISM: Artificial Sequence
<220> FEATURE:
<223> OTHER INFORMATION: Reverse Primer used to generate DNA corresponding to a region of the SMN2 gene

<400> SEQUENCE: 10

```
cgcggatccg tgctgctcta tgccagca                                        28
```

<210> SEQ ID NO 11
<211> LENGTH: 6
<212> TYPE: DNA

```
<213> ORGANISM: Artificial Sequence
<220> FEATURE:
<223> OTHER INFORMATION: 5 prime end of each primer at 5 prime end of
      exon 6 where a BamHI site was added

<400> SEQUENCE: 11

ggatcc                                                                   6


<210> SEQ ID NO 12
<211> LENGTH: 70
<212> TYPE: DNA
<213> ORGANISM: Artificial Sequence
<220> FEATURE:
<223> OTHER INFORMATION: 5 prime deg UTR added to the modified vector
      using the HindIII site and the BamHI site

<400> SEQUENCE: 12

tagcttctta cccgtactcc accgttggca gcacgatcgc acgtcccacg tgaaccattg       60

gtaaaccctg                                                              70


<210> SEQ ID NO 13
<211> LENGTH: 120
<212> TYPE: DNA
<213> ORGANISM: Artificial Sequence
<220> FEATURE:
<223> OTHER INFORMATION: 3 prime deg UTR added to the modified vector
      using the HindIII site and the BamHI site

<400> SEQUENCE: 13

atcgaaagta caggactagc cttcctagca accgcgggct gggagtctga gacatcactc       60

aagatatatg ctcggtaacg tatgctctag ccatctaact attccctatg tcttataggg      120


<210> SEQ ID NO 14
<211> LENGTH: 7
<212> TYPE: DNA
<213> ORGANISM: Artificial Sequence
<220> FEATURE:
<223> OTHER INFORMATION: Seven nucleotides from the inserted guanine
      residue to the last nucleotide of exon 7 missing
      in the clones containing the SMN1-G minigene
      fragment

<400> SEQUENCE: 14

gtaagga                                                                  7


<210> SEQ ID NO 15
<211> LENGTH: 6
<212> TYPE: DNA
<213> ORGANISM: Artificial Sequence
<220> FEATURE:
<223> OTHER INFORMATION: Sequence element generated  through the
      G-insertion in the SMN1-G version of the minigene

<400> SEQUENCE: 15

gtaagg                                                                   6


<210> SEQ ID NO 16
<211> LENGTH: 6
<212> TYPE: DNA
<213> ORGANISM: Artificial Sequence
<220> FEATURE:
<223> OTHER INFORMATION: 5' end of intron 7 of the SMN1-G version of the
      minigene

<400> SEQUENCE: 16

gtaagt                                                                   6
```

<210> SEQ ID NO 17
<211> LENGTH: 27
<212> TYPE: DNA
<213> ORGANISM: Artificial Sequence
<220> FEATURE:
<223> OTHER INFORMATION: DNA corresponding to a region of the SMN2 mRNA starting from the initiation codon and ending at nucleic acid residue 27 of exon 8

<400> SEQUENCE: 17
gaaatgctgg catagagcag cactaaa 27

<210> SEQ ID NO 18
<211> LENGTH: 41
<212> TYPE: DNA
<213> ORGANISM: Artificial Sequence
<220> FEATURE:
<223> OTHER INFORMATION: Forward primer used to amplify DNA of the SMN2 mRNA starting from the initiation codon and ending at nucleic acid residue 27 of exon 8

<400> SEQUENCE: 18
cgcaggatcc gcgatgagca gcggcggcag tggtggcggc g 41

<210> SEQ ID NO 19
<211> LENGTH: 49
<212> TYPE: DNA
<213> ORGANISM: Artificial Sequence
<220> FEATURE:
<223> OTHER INFORMATION: Reverse primer used to amplify DNA of the SMN2 mRNA starting from the initiation codon and ending at nucleic acid residue 27 of exon 8

<400> SEQUENCE: 19
cgcaggatcc tttagtgctg ctctatgcca gcatttccat ataatagcc 49

<210> SEQ ID NO 20
<211> LENGTH: 70
<212> TYPE: DNA
<213> ORGANISM: Artificial Sequence
<220> FEATURE:
<223> OTHER INFORMATION: 5 prime deg UTR added to the modified vector using the HindIII site of the pcDNA 3.1/Hygro vector and the BamHI

<400> SEQUENCE: 20
tagcttctta cccgtactcc accgttggca gcacgatcgc acgtcccacg tgaaccattg 60
gtaaaccctg 70

<210> SEQ ID NO 21
<211> LENGTH: 120
<212> TYPE: DNA
<213> ORGANISM: Artificial Sequence
<220> FEATURE:
<223> OTHER INFORMATION: 3 prime deg UTR added to the modified vector using pcDNA3.1/Hygro vector together with a start codon upstream of the BamHI site

<400> SEQUENCE: 21
atcgaaagta caggactagc cttcctagca accgcgggct gggagtctga gacatcactc 60
aagatatatg ctcggtaacg tatgctctag ccatctaact attccctatg tcttataggg 120

<210> SEQ ID NO 22
<211> LENGTH: 12
<212> TYPE: DNA

-continued

```
<213> ORGANISM: Artificial Sequence
<220> FEATURE:
<223> OTHER INFORMATION: 5 prime to 3 prime construct containing 12
      additional nucleotides from exon 8

<400> SEQUENCE: 22

agcagcacta aa                                                          12


<210> SEQ ID NO 23
<211> LENGTH: 49
<212> TYPE: DNA
<213> ORGANISM: Artificial Sequence
<220> FEATURE:
<223> OTHER INFORMATION: Primer used in site-directed mutagenesis to
      replace an adenine reside in the stop codon of
      SMN2 with a thymine residue

<400> SEQUENCE: 23

cgcaggatcc tttagtgctg ctcaatgcca gcatttccat ataatagcc                  49


<210> SEQ ID NO 24
<211> LENGTH: 30
<212> TYPE: DNA
<213> ORGANISM: Artificial Sequence
<220> FEATURE:
<223> OTHER INFORMATION: Stop codon after the 27th nucleotide of exon 8
      generated by site-directed mutagenesis

<400> SEQUENCE: 24

gaaatgctgg catagagcag cactaaatga                                       30


<210> SEQ ID NO 25
<211> LENGTH: 40
<212> TYPE: DNA
<213> ORGANISM: Artificial Sequence
<220> FEATURE:
<223> OTHER INFORMATION: Primer used in site-directed mutagenesis to
      generate the stop codon after the 27th nucleotide
      of exon 8

<400> SEQUENCE: 25

ggcattgagc agcactaaat gatccgaaga cgccaaaaac                            40
```